US011780853B2

United States Patent
Li et al.

(10) Patent No.: US 11,780,853 B2
(45) Date of Patent: *Oct. 10, 2023

(54) SUBSTITUTED N-PYRIMIDIN-4-YL-3-AMIN-OPYRROLO[3,4-C]PYRAZOLES AS PROTEIN KINASE C INHIBITORS

(71) Applicant: PFIZER INC., New York, NY (US)

(72) Inventors: Hui Li, Carlsbad, CA (US); Seiji Nukui, San Diego, CA (US); Stephanie Anne Scales, San Diego, CA (US); Min Teng, San Diego, CA (US); Chunfeng Yin, San Diego, CA (US)

(73) Assignee: PFIZER INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/539,948

(22) Filed: Dec. 1, 2021

(65) Prior Publication Data

US 2022/0089613 A1    Mar. 24, 2022

Related U.S. Application Data

(63) Continuation of application No. 16/387,369, filed on Apr. 17, 2019, now Pat. No. 11,220,518, which is a continuation of application No. 15/376,279, filed on Dec. 12, 2016, now Pat. No. 10,316,045, which is a continuation of application No. 14/506,470, filed on Oct. 3, 2014, now Pat. No. 9,518,060, which is a continuation of application No. 13/450,388, filed on Apr. 18, 2012, now Pat. No. 8,877,761, which is a continuation of application No. 12/523,965, filed as application No. PCT/IB2008/000297 on Feb. 4, 2008, now Pat. No. 8,183,255.

(60) Provisional application No. 61/020,965, filed on Jan. 14, 2008, provisional application No. 60/989,086, filed on Nov. 19, 2007, provisional application No. 60/888,749, filed on Feb. 7, 2007.

(51) Int. Cl.
   A61K 31/4162    (2006.01)
   C07D 487/04    (2006.01)
   C07D 519/00    (2006.01)

(52) U.S. Cl.
   CPC ......... C07D 519/00 (2013.01); C07D 487/04 (2013.01)

(58) Field of Classification Search
   CPC ..................... A61K 31/4162; C07D 487/04
   USPC ........................................ 514/405; 548/360.5
   See application file for complete search history.

(56) References Cited

U.S. PATENT DOCUMENTS

| | | | |
|---|---|---|---|
| 8,183,255 B2 | 5/2012 | Li et al. | |
| 8,877,761 B2 | 11/2014 | Li et al. | |
| 9,518,060 B2 | 12/2016 | Li et al. | |
| 10,316,045 B2 | 6/2019 | Li et al. | |
| 11,220,518 B2 | 1/2022 | Li et al. | |
| 2003/0171357 A1 | 9/2003 | Fancelli et al. | |
| 2010/0130501 A1 | 5/2010 | Li et al. | |

FOREIGN PATENT DOCUMENTS

| | | |
|---|---|---|
| WO | WO-0212242 A2 | 2/2002 |
| WO | WO-2004056827 A2 | 7/2004 |
| WO | WO-2006072831 A1 | 7/2006 |
| WO | WO-2008096260 A1 | 8/2008 |

OTHER PUBLICATIONS

Ahmad et al. Expression of the Antisense cDNA for Protein Kinase Cα Attenuates Resistance in Doxorubicin-Resistant MCF-7 Breast Carcinoma Cells. Molecular Pharmacology 43:858-862 (1993).
Akinaga et al. Antitumor Activity of UCN-01, a Selective Inhibitor of Protein Kinase C, in Murine and Human Tumor Models. Cancer Research 51:4888-4892 (1991).
Bastyr et al. Increased Platelet Protein Kinase C-β(PKC-β) in IDDM. Diabetes 304(Suppl. 1)-42:97A (1993).

(Continued)

*Primary Examiner* — Douglas M Willis

(74) *Attorney, Agent, or Firm* — WILSON SONSINI GOODRICH & ROSATI

(57) ABSTRACT

The present invention relates to protein kinase C beta II inhibiting compounds of Formula (A):

(A)

wherein A, B, $R^1$, $R^2$, $R^3$, $R^4$, $R^5$, $R^6$, $R^7$, $R^8$, $R^9$, and $R^{10}$ are as defined herein. The invention further relates to pharmaceutical compositions comprising the compounds of Formula (A), or pharmaceutically acceptable salts thereof, and methods for treating a disease or disorder selected from the group consisting of Alzheimer's disease, cancer, a cardiovascular disease, a central nervous system disorder, depression, a dermatological disease, diabetes mellitus, a complication arising from diabetes mellitus, a disease in which the liver is a target organ inflammation, an inflammatory disorder, ischemia, and a viral disease.

15 Claims, No Drawings

(56) References Cited

OTHER PUBLICATIONS

Bilder et al. Phorbol-12, 13-Dibutyrate-Induced Vasoconstriction in Vivo: Characterization of Response in Genetic Hypertension. The Journal of Pharmacology and Experimental Therapeutics 252(2):526-530 (1990).
Bollag et al. Effects of the Selective Protein Kinase C Inhibitor, Ro 31-7549, on the Proliferation of Cultured Mouse Epidermal Keratinocytes. The Journal of Investigative Dermatology 100(3):240-246 (1993).
Braz et al. PKC-α Regulates Cardiac Contractility and Propensity Toward Heart Failure. Nature Medicine 10(3):248-254 (2004).
Chen et al. Diacylglycerol-Protein Kinase C Signalling in Skeletal Muscle: A Possible Link to Insulin Resistance. Transactions of the Association of American Physicians 104:206-212 (1991).
Chin et al. Overexpression of Protein Kinase C Isoenzymes α, β1, γ, and & in Cells Overexpressing the Insulin Receptor. The Journal of Biological Chemistry 268(9):6338-6347 (1993).
Craven et al. Protein Kinase C Is Activated in Glomeruli from Streptozotocin Diabetic Rats. The Journal of Clinical Investigation, Inc. 83:1667-1675 (1989).
Dorwald. Side Reactions In Organic Synthesis: A Guide to Successful Synthesis Design. Weinheim: WILEY-VCH Verlag GmbH & Co. KGaA. 2005. Preface.
Graff et al. The Protein Kinase Cβ-Selective Inhibitor, Enzastaurin (LY317615.HCl), Suppresses Signaling Through the AKT Pathway, Induces Apoptosis, and Suppresses Growth of Human Colon Cancer and Glioblastoma Xenografts. Cancer Research 65(16):7462-7469 (2005).
Hackman et al. Translation of Research Evidence From Animals to Humans. JAMA 296(14):1731-1732 (2006).
Hara et al. Staurosporine, a Novel Protein Kinase C Inhibitor, Prevents Postischemic Neuronal Damage in the Gerbil and Rat. Journal of Cerebral Blood Flow and Metabolism 10:646-653 (1990).
Hegemann et al. Effects of Tiflucarbine as a Dual Protein Kinase C/calmodulin Antagonist on Proliferation of Human Keratinocytes and Release of Reactive Oxygen Species from Human Leukocytes. Archives of Dermatological Research 283:456-460 (1991).
Horn et al. Decreased Protein Kinase C Activity in Psoriatic Versus Normal Epidermis. The Society for Investigative Dermatology, Inc. 88(2):220-222 (1987).
Hsieh et al. Human Vitamin D Receptor is Selectively Phosphorylated by Protein Kinase C on Serine 51, a Residue Crucial to its Trans-Activation Function. PNAS USA. 88:9315-9319 (1991).
Hsieh et al. Phosphorylation of the Human Vitamin D Receptor by Protein Kinase C. The Journal of Biological Chemistry 268(20):15118-15126 (1993).
Huang. The Mechanism of Protein Kinase C Activation. Trends in Neurosciences 12(11):425-432 (1989).
Inoguchi et al. Preferential Elevation of Protein Kinase C Isoform βII and Diacylglycerol Levels in the Aorta and Heart of Diabetic Rats: Differential Reversibility to Glycemic Control by Islet Cell Transplantation. PNAS USA 89:11059-11063 (1992).
Jordan. Tamoxifen: A Most Unlikely Pioneering Medicine. Nature Reviews: Drug Discovery. 2:205-213 (2003).
Karasik et al. Increased Protein Kinase C Activity is Linked to Reduced Insulin Receptor Autophosphorylation in Liver of Starved Rats. The Journal of Biological Chemistry 265(18):10226-10231 (1990).
Kobayashi et al. Platelet-Activating Factor Modulates Microvascular Transport by Stimulation of Protein Kinase C. The American Physiological Society 266:H1214-H1220 (1994).
Lee et al. Activation of Protein Kinase C by Elevation of Glucose Concentration: Proposal for a Mechanism in the Development of Diabetic Vascular Complications. PNAS USA 86:5141-5145 (1989).
Lee et al. Differential Regulation of Protein Kinase C and (Na,K)-Adenosine Triphosphatase Activities by Elevated Glucose Levels in Retinal Capillary Endothelial Cells. The Journal of Clinical Investigation 83:90-94 (1989).

Matsumoto et al. Staurosporine, a Protein Kinase C Inhibitor Interferes with Proliferation of Arterial Smooth Muscle Cells. Biochemical and Biophysical Research Communications 158(1):105-109 (1989).
Menne at al. Diminished Loss of Proteoglycans and Lack of Albuminuria in Protein Kinase C-α-Deficient Diabetic Mice. Diabetes 53:2101-2109 (2004).
Meyer et al. A Derivative of Staurosporine (CGP 41 251) Shows Selectivity for Protein Kinase C Inhibition and In Vitro Anti-Proliferative As Well As In Vivo Anti-Tumor Activity. International Journal of Cancer 43:851-856 (1989).
Morrison. Kinetics of the Reversible Inhibition of Enzyme-Catalysed Reactions by Tight-Binding Inhibitors. Biochimica et Biophysics Acta 185:269-286 (1969).
Muid et al. A Novel Conformationally Restricted Protein Kinase C Inhibitor, Ro 31-8425, Inhibits Human Neutrophil Superoxide Generation by Soluble, Particulate and Post-receptor Stimuli. Federation of European Biochemical Societies 293(1,2):169-172 (1991).
Mulqueen et al. Oral, Anti-inflammatory Activity of a Potent, Selective. Protein Kinase C Inhibitor. Agents Actions 37:85-89 (1992).
Murray et al. Protein Kinase C Isotypes in Human Erythroleukemia (K562) Cell Proliferation and Differentiation. The Journal of Biological Chemistry 268(21):15847-15853(1993).
Partovian et al. Regulation of Protein Kinase B/Akt Activity and Ser473 Phosphorylation by Protein Kinase Cα in Endothelial Cells. Cellular Signalling 16:951-957 (2004).
Patani et al. Bioisosterism: A Rational Approach in Drug Design. Chemical Reviews 96:3147-3176 (1996).
PCT/IB2008/000297 International Preliminary Report on Patentability dated Aug. 11, 2009.
PCT/IB2008/000297 International Search Report dated Jun. 23, 2008.
Raynaud et al. Protein Kinase C Activity in Normal and Psoriatic Cells: Cultures of Fibroblasts and Lymphocytes. British Journal of Dermatology 124:542-546 (1991).
Rotenberg et al. Protein Kinase C in Neoplastic Cells. Biochemical and Molecular Aspects of Selected Cancers 1:25-73 (1991).
Shibata et al. Neuroprotective Effect of Protein Kinase C Inhibitors on Oxygen/Glucose Free-Induced Decreases in 2-Deoxyglucose Uptake and CA1 Field Potentials in Rat Hippocampal Slices. Brain Research 594:290-294 (1992).
Shimohama et al. Assessment of Protein Kinase C Isozymes by Two-site Enzyme Immunoassay in Human Brains and Changes in Alzheimer's Disease. Neurology 43:1407-1413 (1993).
Sonoki et al. Protein at the Time in the Left Cardiac Ventricle Relaxation Obstacle, The Role of Kinase C*. Kokyu to Jukan 137(6):668-674 (1989) (English Abstract).
Tesfamariam et al. Elevated Glucose Impairs Endothelium-dependent Relaxation by Activating Protein Kinase C. The American Journal of Clinical Investigation 87:1643-1648 (1991).
Toullec et al. The Bisindolylmaleimide Gf 109203X Is a Potent and Selective Inhibitor of Protein Kinase C*. The Journal of Biological Chemistry. 266(24):15771-15781 (1991).
Towemy et al. The Effect of New Potent Selective Inhibitors of Protein Kinase C on the Neutrophil Respiratory Burst. Biochemical and Biophysical Research Communications 171(3):1087-1092 (1990).
U.S. Appl. No. 12/523,965 Office Action dated Oct. 12, 2011.
U.S. Appl. No. 13/450,388 Office Action dated Feb. 25, 2013.
U.S. Appl. No. 13/450,388 Office Action dated Oct. 10, 2012.
U.S. Appl. No. 13/450,388 Office Action dated Oct. 29, 2013.
U.S. Appl. No. 14/506,470 Office Action dated Dec. 7, 2015.
U.S. Appl. No. 14/506,470 Office Action dated May 11, 2015.
U.S. Appl. No. 15/376,279 Office Action dated Jan. 29, 2018.
U.S. Appl. No. 15/376,279 Office Action dated Jul. 23, 2018.
U.S. Appl. No. 15/376,279 Office Action dated Sep. 22, 2017.
U.S. Appl. No. 16/387,369 Office Action dated Apr. 7, 2020.
U.S. Appl. No. 16/387,369 Office Action dated May 13, 2021.
U.S. Appl. No. 16/387,369 Office Action dated Oct. 16, 2020.
Vinik. The Protein Kinase C-β Inhibitor, Ruboxistaurin, for the Treatment of Diabetic Microvascular Complications. Expert Opinion Investigative Drugs 14(12):1547-1559 (2005).

(56) References Cited

OTHER PUBLICATIONS

Way et al. Protein Kinase C and the Development of Diabetic Vascular Complications. Diabetic Medicine 18:945-959 (2001).

SUBSTITUTED N-PYRIMIDIN-4-YL-3-AMINOPYRROLO[3,4-C]PYRAZOLES AS PROTEIN KINASE C INHIBITORS

This application is a continuation of U.S. patent application Ser. No. 16/387,369, filed Apr. 17, 2019; which is a continuation of U.S. patent application Ser. No. 15/376,279, filed Dec. 12, 2016, now U.S. Pat. No. 10,316,045, issued Jun. 11, 2019; which is a continuation of U.S. patent application Ser. No. 14/506,470, filed Oct. 3, 2014, now U.S. Pat. No. 9,518,060, issued Dec. 13, 2016; which is a continuation of U.S. patent application Ser. No. 13/450,388, filed Apr. 18, 2012, now U.S. Pat. No. 8,877,761, issued Nov. 4, 2014; which is a continuation of U.S. patent application Ser. No. 12/523,965, filed Dec. 18, 2009, now U.S. Pat. No. 8,183,255, issued May 22, 2012; which is a U.S. National Stage of International Patent Application No. PCT/IB08/00297, filed Feb. 4, 2008; which claims the benefit of U.S. Provisional Application No. 61/020,965, filed Jan. 14, 2008; U.S. Provisional Application No. 60/989,086, filed Nov. 19, 2007; and U.S. Provisional Application No. 60/888,749, filed Feb. 7, 2007, the contents of which are hereby incorporated by reference in their entireties.

FIELD OF THE INVENTION

The present invention relates to novel compounds, to pharmaceutical compositions comprising the compounds, as well as to the use of the compounds in medicine and for the preparation of a medicament which acts on the human protein kinase C enzyme, and in particular the beta II isoform (pkcβII).

BACKGROUND OF THE INVENTION

Protein kinase C (PKC) is a superfamily of lipid-activated Ser/Thr kinases involved in multiple signal transduction pathways. There are thirteen PKC-isoforms that have been identified and are classified according to their regulation by cellular signaling molecules such as diacylglycerol, phospholipids, and calcium. The protein kinase C isozymes, alpha, beta (two splice variants PKCBI and PKCBII) and gamma, require membrane phospholipids, calcium and diacylglycerolphorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipids for their activation.

The tissue-specific expression and activation of PKC-isoforms suggests that individual PKC-isoforms might be potential therapeutic targets. For diabetes, activation of PKC-beta has been demonstrated in tissues of diabetic animals and has been implicated in the development of microvascular abnormalities related to the hyperglycemic state. Genetic polymorphisms have been identified in the 5'-flanking upstream region of the PKCB gene in Japanese patients with type II diabetes. This PKCB genetic variation was associated with a significant increase in the susceptibility to develop diabetic vascular complications and macrovascular diseases such as coronary heart disease.

In a large case-control study at the Joslin Diabetes Center, additional polymorphisms were identified in the PKCB promoter region that had an association with type I diabetes mellitus (duration<24 years) and a greater risk for development of diabetic nephropathy. Administration of PKCB inhibitors such as ruboxistaurin mesylate (LY333531, Lilly) in diabetic animal models, was shown to prevent or ameliorate the hemodynamic changes and vascular damage associated with diabetic nephropathy, diabetic peripheral neuropathy, and diabetic retinopathy. Way, K. J. et al, Diabet. Med. 18: 945-959 (2001); Vinik, A., Expert Opin. Investig. Drugs 14: 1547-1559 (2005). Together with additional data from phase II and phase III clinical studies of ruboxistaurin mesylate for treatment of diabetes and diabetic microvascular complications, there is a building body of evidence to support the rationale that PKCβ can function as a molecular target for diabetic complications and for the development of selective-PKCβ inhibitors as potential therapeutic agents.

The compounds of the present invention are protein kinase C beta II inhibitors, and are therefore believed to be useful in the treatment of conditions associated with diabetes mellitius and its complications, cancer, ischemia, inflammation, central nervous system disorders, cardiovascular disease and dermatological disease.

SUMMARY OF THE INVENTION

The present invention is directed to a compound or pharmaceutically acceptable salt of Formula A,

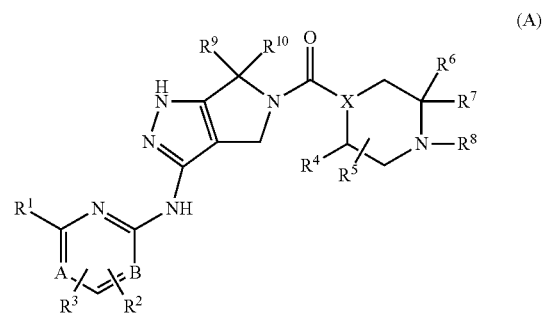

(A)

wherein

X is C—$R^{11}$ or N, wherein $R^{11}$ is H, halo, OH, $C_1$-$C_3$alkyl, $CF_3$, or CN;

A and B are independently C or N;

$R^1$, $R^2$ and $R^3$ are each independently selected from H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; wherein $R^2$ and $R^3$ may together optionally cyclize to form a saturated or unsaturated 3-7 membered heterocyclyl fused to the 6-membered N-containing heteroaryl to which they are attached; and wherein any of the said alkyl, alkenyl, alkynyl, $R^a$, $R^b$, $R^c$, $R^d$, $R^e$, $C_3$-$C_{12}$ cycloalkyl, phenyl or 3-15 membered heterocyclyl, may independently be further optionally substituted by 0-3 $R^{12}$ groups;

$R^4$ and $R^5$ are each independently selected from H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups, $R^6$ and $R^7$ are each independently H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; wherein $R^6$ and $R^7$ may together optionally cyclize to form a $C_3$-$C_7$ cycloalkyl and wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups;

$R^8$ is H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —($(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl are independently optionally further substituted by 1-3 groups selected from —F, $C_1$-$C_3$ alkyl, $C_1$-$C_3$ perfluoroalkyl, hydroxyl, $C_1$-$C_6$alkoxyl, or oxo;

$R^9$ and $R^{10}$ are each independently $C_1$-$C_2$ alkyl or can together cyclize to form a cyclopropyl or cyclobutyl;

each $R^{12}$ is independently H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl, are independently optionally further substituted by 1-3 groups selected from —F, $C_1$-$C_3$ alkyl, $C_1$-$C_3$ perfluoroalkyl, hydroxyl, $C_1$-$C_6$alkoxyl or oxo;

each $R^a$, $R^b$ and $R^c$ is independently selected from H, $C_1$-$C_8$ alkyl, $C_2$-$C_8$ alkenyl, —$(R^d)_m$—($C_3$-$C_8$ cycloalkyl), —$(R^d)_m$—($C_3$-$C_8$ cycloalkenyl), $C_2$-$C_8$ alkynyl, —$(R^d)_m$-phenyl, or —$(R^d)_m$-(3-7 membered heterocyclyl), and each $R^a$, $R^b$ and $R^c$ is independently optionally further substituted by 1-3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may together optionally form a 3-7 membered heterocyclyl, which may optionally be further substituted by 0-3 groups selected from halide, hydroxyl, —CN, $C_1$-$C_6$ alkyl, $C_1$-$C_6$ perfluoroalkyl, $C_1$-$C_6$ alkoxyl or $C_1$-$C_6$ alkylamino;

each $R^d$ and $R^e$ is independently-($C_1$-$C_3$ alkylene)-, —($C_2$-$C_5$ alkenylene)-, or —($C_2$-$C_5$ alkynylene)-;

and each m is independently 0 or 1;

with the proviso that when X is N, $R^6$ and $R^7$ are not both H, and that when X is C—$R^{11}$, $R^6$ and $R^7$ are both H.

In one embodiment of the invention, $R^9$ and $R^{10}$ are both methyl.

In another embodiment of the invention, X is N and $R^6$ and $R^7$ are each independently H or $C_1$-$C_6$alkyl but are not both H.

In one embodiment of the invention, A is N and B is C. In an alternative embodiment, A is C and B is N.

In another embodiment of the invention, $R^6$ and $R^7$ are both methyl. In an alternative embodiment, $R^6$ is H and $R^7$ is methyl.

In one embodiment of the invention, $R^4$ is $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; wherein the said $R^a$, $R^b$, $R^c$, $R^d$, $R^e$, $C_3$-$C_{12}$ cycloalkyl, aryl, 3-15 membered heterocyclyl, are independently optionally further substituted by 0-3 $R^{12}$ groups.

In a further embodiment of the invention, $R^4$ is methyl.

In another embodiment of the invention, $R^1$ is $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S (O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; wherein the said —R$^a$, R$^b$, R$^c$, R$^d$, R$^e$, C$_3$-C$_{12}$ cycloalkyl, aryl, the said 3-15 membered heterocyclyl, are independently optionally further substituted by 0-3 R$^{12}$ groups.

In a further embodiment of the invention, R$^1$ is —(R$^d$)$_m$—OR$^a$, C$_1$-C$_8$ alkyl, or —(R$^d$)$_m$—NR$^a$R$^b$. In another further embodiment of the invention, R$^8$ is R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—OR$^a$, or —(R$^d$)$_m$—NR$^a$R$^b$.

In another embodiment of the invention, each R$^d$ and R$^e$ is independently an —(C$_1$-C$_3$ alkylene).

The present invention is further directed to a compound or pharmaceutically acceptable salt of Formula B,

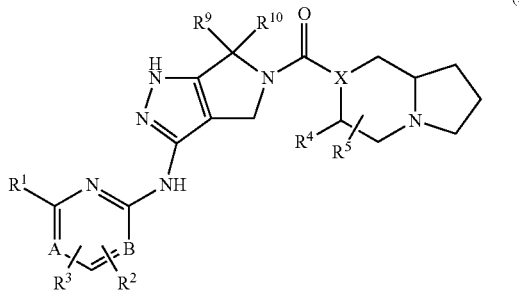

(B)

wherein

X is C—R$^{11}$ or N, wherein R$^{11}$ is H, halo, OH, C$_1$-C$_3$alkyl, CF$_3$, or CN;

A and B are independently C or N;

R$^1$ is R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^a$, R$^b$, R$^c$, R$^d$, R$^e$, C$_3$-C$_{12}$ cycloalkyl, phenyl or 3-15 membered heterocyclyl, may independently be further optionally substituted by 0-3 R$^{12}$ groups;

R$^2$ and R$^3$ are each independently selected from H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^e$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; wherein R$^2$ and R$^3$ may together optionally cyclize to form a saturated or unsaturated 3-7 membered heterocyclyl fused to the 6-membered N-containing heteroaryl to which they are attached; and wherein any of the said alkyl, alkenyl, alkynyl, R$^a$, R$^b$, R$^c$, R$^d$, R$^e$, C$_3$-C$_{12}$ cycloalkyl, phenyl or 3-15 membered heterocyclyl, may independently be further optionally substituted by 0-3 R$^{12}$ groups;

R$^4$ and R$^5$ are each independently selected from H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —((R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^a$, R$^b$, R$^c$, R$^d$, R$^e$, C$_3$-C$_{12}$ cycloalkyl, phenyl, or 3-15 membered heterocyclyl are independently optionally further substituted by 1-3 groups selected from —F, C$_1$-C$_3$ alkyl, C$_1$-C$_3$ perfluoroalkyl, hydroxyl, C$_1$-C$_6$alkoxyl, or oxo;

R$^9$ and R$^{10}$ are each independently C$_1$-C$_2$ alkyl or can together cyclize to form a cyclopropyl or cyclobutyl;

each R$^{12}$ is independently H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^a$, R$^b$, R$^c$, R$^d$, R$^e$, C$_3$-C$_{12}$ cycloalkyl, phenyl, or 3-15 membered heterocyclyl, are independently optionally further substituted by 1-3 groups selected from —F, $C_1$-$C_3$ alkyl, $C_1$-$C_3$ perfluoroalkyl, hydroxyl, $C_1$-$C_6$alkoxyl or oxo;

each $R^a$, $R^b$ and $R^c$ is independently selected from H, $C_1$-$C_8$ alkyl, $C_2$-$C_8$ alkenyl, —$(R^d)_m$—($C_3$-$C_8$ cycloalkyl), —$(R^d)_m$—($C_3$-$C_8$ cycloalkenyl), $C_2$-$C_8$ alkynyl, —$(R^d)_m$-phenyl, or —$(R^d)_m$-(3-7 membered heterocyclyl), and each $R^a$, $R^b$ and $R^c$ is independently optionally further substituted by 1-3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may together optionally form a 3-7 membered heterocyclyl, which may optionally be further substituted by 0-3 groups selected from halide, hydroxyl, —CN, $C_1$-$C_6$ alkyl, $C_1$-$C_6$ perfluoroalkyl, $C_1$-$C_6$ alkoxyl or $C_1$-$C_6$ alkylamino;

each $R^d$ and $R^e$ is independently-($C_1$-$C_3$ alkylene)-, —($C_2$-$C_5$ alkenylene)-, or —($C_2$-$C_5$ alkynylene)-;

and each m is independently 0 or 1.

In one embodiment of the invention of Formula (B), A is N and B is C.

In a further embodiment of Formula (B), wherein $R^9$ and $R^{10}$ are both methyl.

In another embodiment of Formula (B), $R^4$ is —$(R^d)_m$—$OR^a$, $C_1$-$C_8$ alkyl, $C_2$-$C_8$ alkenyl or $C_2$-$C_8$ alkynyl. In a further embodiment, $R^4$ is methyl.

In another embodiment of Formula (B), $R^1$ is —$(R^d)_m$—$OR^a$, $C_1$-$C_8$ alkyl, or —$(R^d)_m$—$NR^aR^b$.

In another embodiment of Formula (B), each $R^d$ and $R^e$ is independently an —($C_1$-$C_3$ alkylene)-.

The present invention is directed to compounds or pharmaceutically acceptable salts selected from the group consisting of:

N4-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$,$N^2$-dimethylpyrimidine-2,4-diamine, N2-cyclopropyl-N4-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-methylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-isopropylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-$N^2$-ethylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-$N^2$,$N^2$-dimethylpyrimidine-2,4-diamine, 5-{[(8S)-6,8-dimethyl-6,9-diazaspiro[4.5]dec-9-yl]carbonyl}-N-(5-fluoro-2-methylpyrimidin-4-yl)-6,6-dimethyl-1,4,5,6-tetrahydropyrrolo[3,4-c]pyrazol-3-amine, $N^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-$N^2$-ethyl-5-fluoropyrim idine-2,4-diamine, $N^4$-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, $N^2$-ethyl-5-fluoro-$N^4$-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine acetate salt, $N^4$-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-$N^2$-ethyl-5-fluoropyrimidine-2,4-diamine, 4-[(6,6-dimethyl-5-{[(2S,5R)-2,4,5-trimethylpiperazin-1-yl]carbonyl}-1,4,5,6-tetrahydropyrrolo[3,4-c]pyrazol-3-yl)amino]pyrimidine-2-carbonitrile, N-(2-ethyl-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-(2-ethyl-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amin, 2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, N-(5-fluoro-2-methylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-(5-fluoro-2-propylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-(5-fluoro-2-isopropylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-(3-fluoro-6-methylpyridin-2-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, 5-{[(3S,8aS)-3,8a-dimethylhexahydropyrrolo[1,2-a]pyrazin-2(1H)-yl]carbonyl}-N-(3-fluoro-6-methylpyridin-2-yl)-6,6-dimethyl-1,4,5,6-tetrahydropyrrolo[3,4-c]pyrazol-3-amine, N-(3-fluoro-6-methylpyridin-2-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine, N-(3-fluoro-6-methylpyridin-2-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-[5-fluoro-2-(methoxymethyl)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-N-(4-methoxypyrimidin-2-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-(4-methylpyrimidin-2-yl)-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-6,6-dimethyl-N-(4-methylpyrimidin-2-yl)-1,4,5,6-tetrahydropyrrolo[3,4-c]pyrazol-3-amine, N-(2-ethoxy-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, N-(2-ethoxy-5-fluoropyrimidin-4-yl)-6,6-dimethyl-5-{[4-ethyl(2S,5R)-2,5-dimethylpiperazin-1-yl]carbonyl}-1,4,5,6-tetrahydropyrrolo[3,4-c]pyrazol-3-amine, N-(2-ethoxy-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-(2-ethoxy-5-fluoropyrimidin-4-yl)-5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-amine, N-(2-ethoxy-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-[(4-fluoro-1-methylpiperidin-4-yl)carbonyl]-N-[5-fluoro-2-(2,2,2-trifluoroethoxy)pyrimidin-4-yl]-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine, 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

The present invention is further directed to a pharmaceutical composition comprising an effective amount of a compound according to any of the preceding claims, or a pharmaceutically acceptable salt thereof, and a pharmaceutically acceptable carrier.

The present invention is further directed to a method of treating diabetes mellitus and its complications, cancer, ischemia, inflammation, central nervous system disorders, cardiovascular disease, Alzheimer's disease and dermatological disase pression, virus diseases, inflammatory disorders, or diseases in which the liver is a target organ, the method comprising administering to a mammal an effective amount of a compound according to any of the preceding claims, or a pharmaceutically acceptable salt thereof.

The present invention is further directed to a method of treating diabetic mellitus and its complications, the method comprising administering to a mammal an effective amount of a compound according to any of the preceding claims. In a further embodiment of this invention, the complications comprise diabetic retinopathy (including macular edema), nephropathy and neuropathy.

Definitions

As used herein, the terms "comprising" and "including" are used in their open, non-limiting sense. As used herein, the terms "$C_1$-$C_8$" or "$C_2$-$C_8$" and so forth, refer to moieties having 1 to 8 or 2 to 8 carbon atoms, respectively.

The term "alkyl", as used herein, unless otherwise indicated, includes saturated monovalent hydrocarbon radicals having straight or branched moieties. Exemplary alkyl moieties have carbon atoms in the range of 1 to 8 carbon atoms, 1 to 6 carbon atoms or 1 to 4 carbon atoms.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxyl", as used herein, unless otherwise indicated, includes O-alkyl groups wherein alkyl is as defined above.

The term "hydroxyl", as used herein, unless otherwise indicated, includes —OH.

The term "amino", as used herein, unless otherwise indicated, is intended to include the —$NH_2$ radical, and any substitutions of the N atom.

The terms "halogen" and "halo", as used herein, unless otherwise indicated, represent chlorine, fluorine, bromine or iodine.

The term "trifluoromethyl", as used herein, unless otherwise indicated, is meant to represent a —$CF_3$ group.

The term "perfluoroalkyl", as used herein, is meant to represent an alkyl group in which all hydrogens attached to the carbons have been replaced by fluorine, such as $CF_3$, $CF_2$—$CF_3$, $C(CF_2)(CF_2)$ and so on.

The term "trifluoromethoxy", as used herein, unless otherwise indicated, is meant to represent a —$OCF_3$ group.

The term "cyano", as used herein, unless otherwise indicated, is meant to represent a —CN group.

The term "$CH_2Cl_2$", as used herein, unless otherwise indicated, is meant to represent dichloromethane.

The term "$C_3$-$C_{12}$ cycloalkyl" or "$C_5$-$C_8$ cycloalkyl", as used herein, unless otherwise indicated, refers to a non-aromatic, saturated or partially saturated, monocyclic or fused, spiro or unfused bicyclic or tricyclic hydrocarbon referred to herein containing a total of from 3 to 12 carbon atoms, or 5-8 ring carbon atoms, respectively. Exemplary cycloalkyls include rings having from 3-10 carbon atoms, such as cyclopropyl, cyclobutyl, cyclopentyl, cyclohexyl, cycloheptyl, and adamantyl. Illustrative examples of cycloalkyl are derived from, but not limited to, the following:

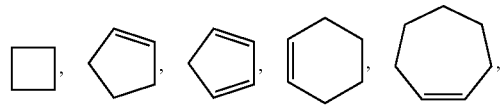

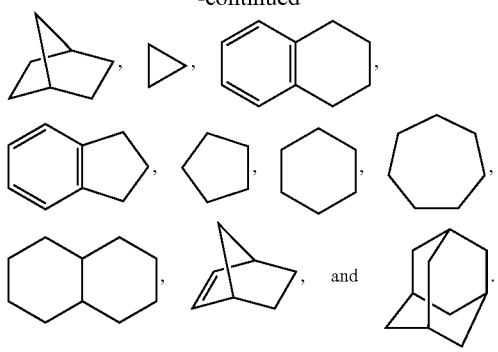

The term "aryl", as used herein, unless otherwise indicated, includes an organic radical derived from an aromatic hydrocarbon by removal of one hydrogen, such as phenyl or naphthyl.

The term "(3-15)-membered heterocycyl", "(3-7)-membered heterocyclyl", "(6-10)-membered heterocyclyl", or "(4 to 10)-membered heterocyclyl", as used herein, unless otherwise indicated, includes aromatic and non-aromatic heterocyclic groups containing one to four heteroatoms each selected from O, S and N, wherein each heterocyclic group has from 3-15, 3-7, 6-10, or 4 to 10 atoms, respectively, in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3 membered heterocyclic group is aziridine, an example of a 4 membered heterocyclic group is azetidinyl (derived from azetidine). An example of a 5 membered heterocyclic group is thiazolyl, an example of a 7 membered ring is azepinyl, and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Heterocycles include monocyclic and polycyclic aromatic ring structures, with "(5-12)-membered heteroaryls" referring to those that are heterocycles having 5 to 12 atoms in their ring system(s). Examples of "(5-12)-membered heteroaryls" are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The above-mentioned heterocyclic groups may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other Illustrative examples of 4 to 10 membered heterocyclic are derived from, but not limited to, the following:

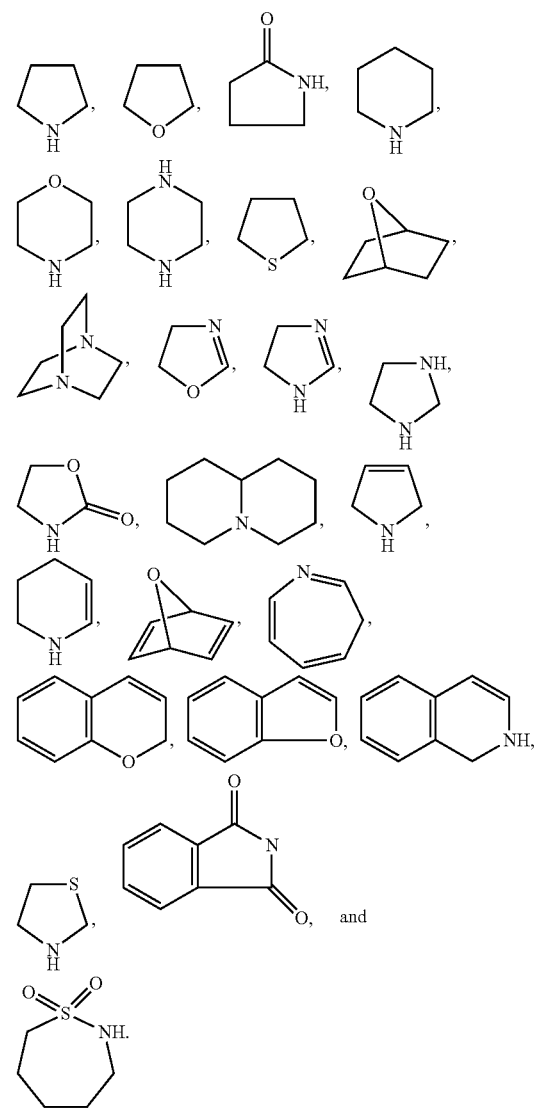

The term "(12-15)-membered heterocyclyl", as used herein, unless otherwise indicated, includes aromatic and non-aromatic heterocyclic groups that are in a partially fused or spirocyclic configuration and which contain at least one N and optionally additional 1 to 5 heteroatoms each selected from O, S and N, wherein the heterocyclic group has from 12 to 15 atoms, respectively, in its system, and with the proviso that any ring of said group does not contain two adjacent O or S atoms. The heterocyclic groups include tricyclic fused ring and spirocyclic systems. An example of a 13-membered tricyclic heterocyclic group is 3,4-dihydropyrazino[1,2-a]benzimidazole and an example of a 15-membered spirocyclic heterocyclic group is 3,4-dihydro-1'H-spirochromene.

Unless otherwise indicated, the term "oxo" refers to =O.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO (dimethylsulfoxide), ethyl acetate, acetic acid, or ethanolamine.

The phrase "pharmaceutically acceptable salt(s)", as used herein, unless otherwise indicated, includes salts of acidic or basic groups which may be present in the compounds of formula (A) or formula (B). The compounds of formula (A) or formula (B) that are basic in nature are capable of forming a wide variety of salts with various inorganic and organic acids. The acids that may be used to prepare pharmaceutically acceptable acid addition salts of such basic compounds of formula (A) or formula (B) are those that form non-toxic acid addition salts, ie, salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The phrase "therapeutically effective amount", as used herein, refers to that amount of drug or pharmaceutical agent that will elicit the biological or medical response of a tissue, system, animal, or human that is being sought by a researcher, veterinarian, medical doctor or other.

The term "substituted" means that the specified group or moiety bears one or more substituents. The term "unsubstituted" means that the specified group bears no substituents. The term "optionally substituted" means that the specified group is unsubstituted or substituted by one or more substituents.

In accordance with convention, in some structural formula herein, the carbon atoms and their bound hydrogen atoms are not explicitly depicted e.g., ╱ represents a methyl group, ╱╲ represents an ethyl group,

represents a cyclopentyl group, etc. Moreover, the depiction of any cylic group (aryl, heterocyclic or cycloalkyl) with a bond that is not directly attached to a ring atom, e.g.,

indicates that the point of attachment may be on any available ring atom of the cyclic group.

Certain compounds of formula (A) or formula (B) may have asymmetric centers and therefore exist in different enantiomeric forms. All optical isomers and stereoisomers of the compounds of formula (A) or formula (B), and mixtures thereof, are considered to be within the scope of the invention. With respect to the compounds of formula (A) or formula (B), the invention includes the use of a racemate, one or more enantiomeric forms, one or more diastereomeric forms, or mixtures thereof. The compounds of formula (A) or formula (B) may also exist as tautomers. This invention relates to the use of all such tautomers and mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein.

The subject invention also includes isotopically-labelled compounds, which are identical to those recited in formula (A) or formula (B), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$ $^{35}S$, $^{18}F$, and $^{36}Cl$, respectively. Compounds of the present invention and pharmaceutically acceptable salts or solvates of said compounds which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula (A) or formula (B) of this invention thereof can generally be prepared by carrying out the procedures disclosed in the Schemes and/or in the Examples below, by substituting a readily available isotopically labeled reagent for a non-isotopically labeled reagent.

The term "mmol", as used herein, unless otherwise indicated, is intended to mean millimole. The term "equiv", as used herein, unless otherwise indicated, is intended to mean equivalent. The term "mL", as used herein, unless otherwise indicated, is intended to mean milliliter. The term "U", as used herein, unless otherwise indicated, is intended to mean units. The term "mm" as used herein, unless otherwise indicated, is intended to mean millimeter. The term "g", as used herein, unless otherwise indicated, is intended to mean gram. The term "kg", as used herein, unless otherwise indicated, is intended to mean kilogram. The term "h", as used herein, unless otherwise indicated, is intended to mean hour. The term "min", as used herein, unless otherwise indicated, is intended to mean minute. The term "μL", as used herein, unless otherwise indicated, is intended to mean microliter. The term "μM", as used herein, unless otherwise indicated, is intended to mean micromolar. The term "μm", as used herein, unless otherwise indicated, is intended to mean micrometer. The term "M", as used herein, unless otherwise indicated, is intended to mean molar. The term "N", as used herein, unless otherwise indicated, is intended to mean normal. The term "nm", as used herein, unless otherwise indicated, is intended to mean nanometer. The term "nM", as used herein, unless otherwise indicated, is intended to mean nanoMolar. The term "amu", as used herein, unless otherwise indicated, is intended to mean atomic mass unit. The term "° C.", as used herein, unless otherwise indicated, is intended to mean Celsius. The term "m/z", as used herein, unless otherwise indicated, is intended to mean, mass/charge ratio. The term "wt/wt", as used herein, unless otherwise indicated, is intended to mean weight/weight. The term "v/v", as used herein, unless otherwise indicated, is intended to mean volume/volume. The term "mL/min", as used herein, unless otherwise indicated, is intended to mean milliliter/minute. The term "UV", as used herein, unless otherwise indicated, is intended to mean ultraviolet. The term "APCI-MS", as used herein, unless otherwise indicated, is intended to mean atmospheric pressure chemical ionization mass spectroscopy. The term "HPLC", as used herein, unless otherwise indicated, is intended to mean high performance liquid chromatograph. The chromatography was performed at a temperature of about 20° C., unless otherwise indicated. The term "LC", as used herein, unless otherwise indicated, is intended to mean liquid chromatograph. The term "LCMS", as used herein, unless otherwise indicated, is intended to mean liquid chromatography mass spectroscopy. The term "TLC", as used herein, unless otherwise indicated, is intended to mean thin layer chromatography. The term "SFC", as used herein, unless otherwise indicated, is intended to mean supercritical fluid chromatography. The term "sat" as used herein, unless otherwise indicated, is intended to mean saturated. The term "aq" as used herein, is intended to mean aqueous. The term "ELSD" as used herein, unless otherwise indicated, is intended to mean evaporative light scattering detection. The term "MS", as used herein, unless otherwise indicated, is intended to mean mass spectroscopy. The term "HRMS (ESI)", as used herein, unless otherwise indicated, is intended to mean high-resolution mass spectrometry (electrospray ionization). The term "Anal.", as used herein, unless otherwise indicated, is intended to mean analytical. The term "Calcd", as used herein, unless otherwise indicated, is intended to mean calculated. The term "N/A", as used herein, unless otherwise indicated, is intended to mean not tested. The term "RT", as used herein, unless otherwise indicated, is intended to mean room temperature. The term "Mth.", as used herein, unless otherwise indicated, is intended to mean Method. The term "Celite®", as used herein, unless otherwise indicated, is intended to mean a white solid diatomite filter agent commercially available from World Minerals located in Los Angeles, Calif. USA. The term "Eg.", as used herein, unless otherwise indicated, is intended to mean example.

Terms such as —$(CR^3R^4)_t$ or —$(CR^{10}R^{11})_v$, for example, are used, $R^3$, $R^4$, $R^{10}$ and $R^{11}$ may vary with each iteration of t or v above 1. For instance, where t or v is 2 the terms-$(CR^3R^4)_v$ or —$(CR^{10}R^{11})_t$ may equal-$CH_2CH_2$—, or —$CH(CH_3)C(CH_2CH_3)(CH_2CH_2CH_3)$—, or any number of similar moieties falling within the scope of the definitions of $R^3$, $R^4$, $R^{10}$ and $R^{11}$.

The term "$K_i$", as used herein, unless otherwise indicated, is intended to mean values of enzyme inhibition constant.

The term "$K_i$ app", as used herein, unless otherwise indicated, is intended to mean $K_i$ apparent. The term "$IC_{50}$", as used herein, unless otherwise indicated, is intended to mean concentrations required for at least 50% enzyme inhibition.

Other aspects, advantages, and features of the invention will become apparent from the detailed description below.

DETAILED DESCRIPTION AND EMBODIMENTS OF THE INVENTION

The following reaction Schemes illustrate the preparation of the compounds of the present invention. Unless otherwise indicated, $R^1$ through $R^{12}$ and $R^a$ through $R^e$ in the reaction schemes and the discussion that follows are as defined above.

DETAILED DESCRIPTION

Compounds of formulas I-III can be made following the synthetic routes in Scheme 1 and Scheme 2. In Scheme 1 and Scheme 2 and the descriptions following, "BOC", "Boc" or "boc" means N-tert-butoxycarbonyl, DCM means $CH_2Cl_2$, DIPEA (also known as Hunig's base) means diisopropyl ethyl amine, DMA means dimethyl amine, "DMF" means dimethyl formamide, "DMSO" means dimethylsulfoxide, Et means-$CH_2CH_3$, "MTBE" means methyl t-butyl ether, NMP means 1-methyl-2-pyrrolidinone, TEA means triethyl amine, TFA means trifluoro acetic acid, THF means tetrahydrofuran. While schemes 1 and 2 and the description refer to compound I, schemes 1 and 2 and the description are equally applicable to compounds II and III.

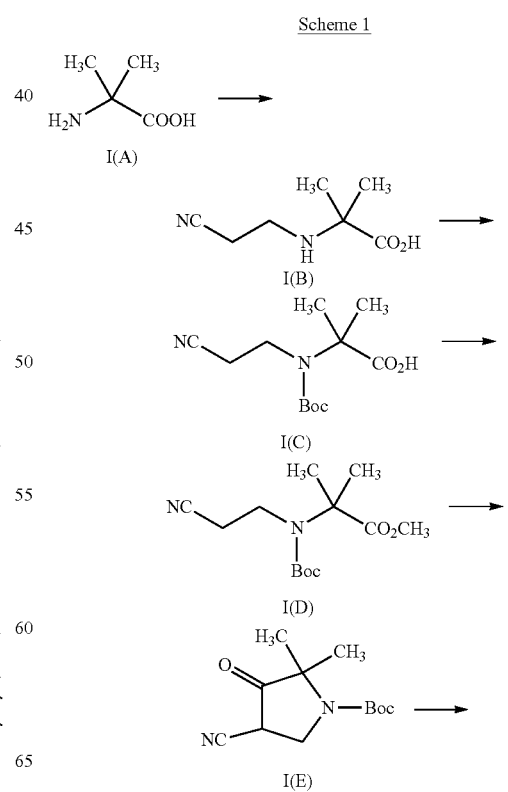

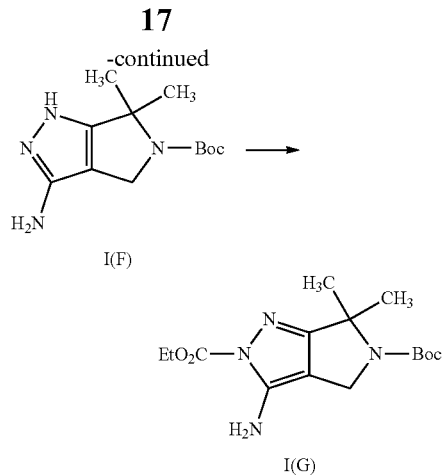

Scheme 1 illustrates the synthesis of the intermediate I(A) used to make compounds of formula I. The amino group of the substituted amino acid I(A) is alkylated to give compound I(B). This can typically be done by treating compound I(A) with an alkylating agent in the presence of a base. An activated electrophilic double bond moiety is a commonly used alkylating reagent. A typical reaction condition of alkylating I(A) with an activated electrophilic double bond moiety is to treat I(A) with the activated double bond moiety in the presence of a strong base. Subsequent aqueous work up affords compound I(B). The amino group of compound I(B) is then protected with a boc group to give compound I(C). This can typically be done by treating compound I(B) with Boc agent in the presence of a base. A typical condition is to treat compound I(B) with $(Boc)_2O$ in the presence of $Me_4NOH$ in MeCN as a solvent. The carboxylic acid group of compound I(C) is then converted into a methyl ester of compound I(D). A typical condition of converting the carboxylic acid group into the methyl ester group is to treat I(C) with methyl iodide in DMF in the presence of a base. Compound I(D) then undergoes an intramolecular aldol condensation to give compound I(E). This can typically be done by treating compound I(D) with a strong base in an aprotic solvent. A typical condition is to treat compound I(D) with t-BuOK in toluene. Subsequent aqueous workup gives compound I(E). Compound I(E) then undergoes a 2+3 cyclization with a hydrazine moiety to form compound I(F). A typical condition of the cyclization is to reflux compound I(E) with hydrazine and acetic acid in EtOH. The free base pyrazole nitrogen of compound I(F) is then acylated to give compound I(G). A typical condition of the acylation is to treat compound I(F) with chloro ethyl carbonate in THF.

More detailed synthetic conditions to compound I(G) of Scheme 1 can be found in U.S. Patent Application Publication No. 2003/0171357 and PCT Publication WO 02/12242, the disclosures of which are incorporated herein by reference.

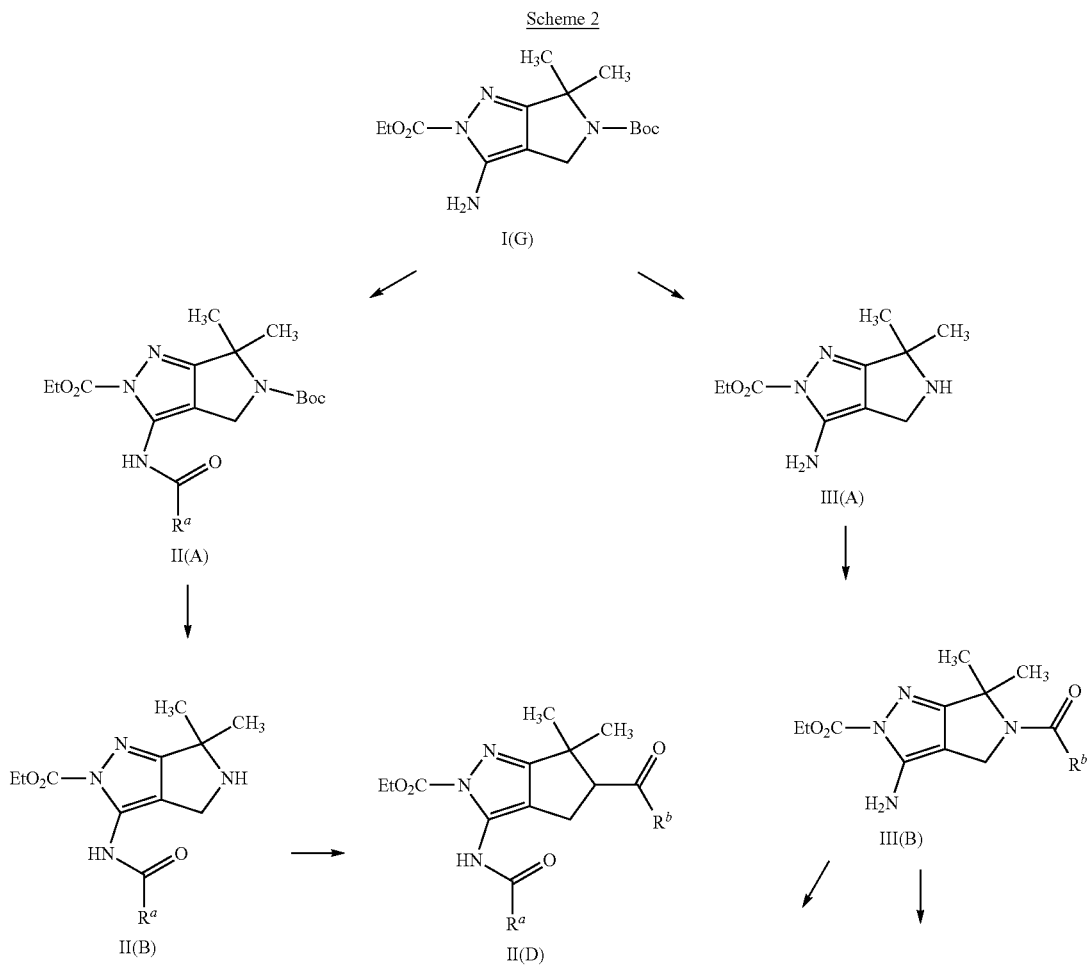

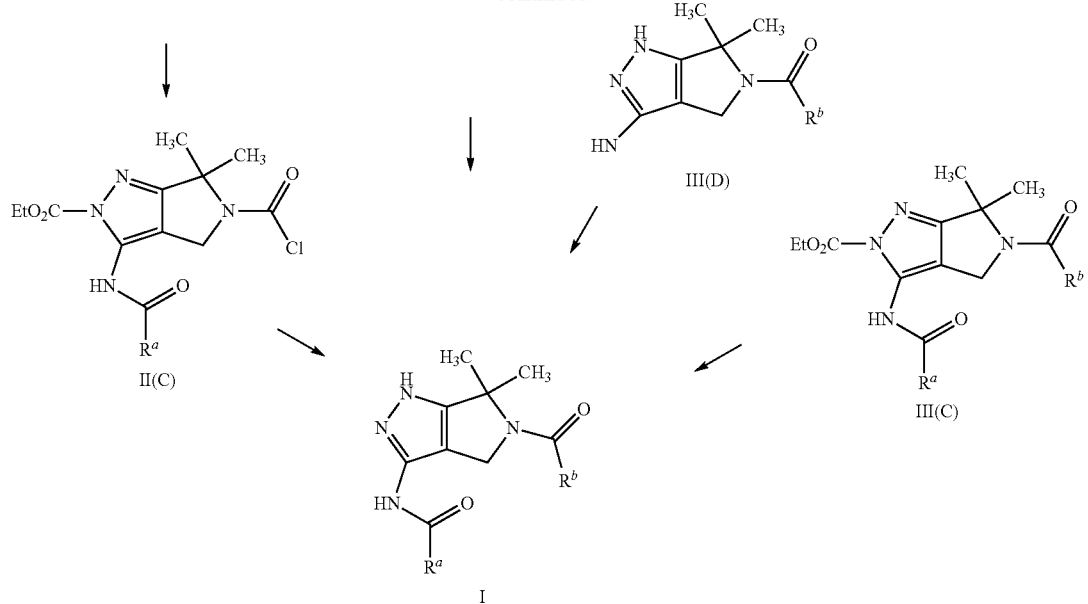

Scheme 2 illustrates two routes through which compounds of formula I can be made from intermediate I(G). In the first route of Scheme 2, compound I(G) undergoes a nucleophilic reaction with an R<sup>a</sup> electrophile moiety. This nucleophilic reaction can be an acylation, alkylation, sulfonylation, reductive amination or one of many other reactions that an amine functionality carries out. A typical acylation reaction condition is to treat compound I(G) with an acylating agent such as R<sup>a</sup>—COCl, in the presence of a base such as 2 equivalents of DIPEA, in a solvent such as dichloromethane. The reaction mixture is stirred at between 0° C. and room temperature for 12 hours. Subsequent aqueous workup gives compound II(A). The Boc group on the pyrrole nitrogen of compound II(A) is then removed to give compound II(B). This can typically be done by treating II(A) with a strong acid. A typical reaction condition is to treat compound II(A) with 4N HCl in dioxane and DCM. Subsequent aqueous workup affords compound II(B). The pyrrole NH of compound II(B) is then coverted to the chloroformate II(C). This can typically be done using phosgene, triphosgene, or some equivalent. A typical reaction condition is to treat II(B) with 2 equivalents of triphosgene in DCM at 0° C. for four hours. Subsequent mild basic workup with saturated NaHCO₃ and purification gives compound II(C). Compound II(C) is then treated with an R<sup>a</sup> nucleophile moiety. The nucleophile can be an alcohol, amine or one of any other functionalities that can react with the electrophile II(C). A typical reaction involves treating II(C) with a nucleophile such as 1.5 equivalents of an alcohol in the presence of 2 equivalents of base such as K₂CO₃ in a solvent such as DME. The reaction is heated to 80° C. for eight hours and the solvent removed. Alternatively, II(C) can be treated with 1.5 equivalents of an amine in the presence of 1 equivalent of base such as DIPEA in a solvent such as THF. Subsequent work up in a protic solvent such as methanol in the presence of base such as TEA followed by purification give compound of formula I.

Alternatively, compound II(B) can then undergoes a nucleophilic reaction with an (COR<sup>b</sup>) electrophile to give compound II(D). The nucleophilic reaction carried out for this transformation can be an alkylation, acylation, sulfonylation, reductive amination. An acylation reaction of II(B) to give II(D) is carried out by treating compound II(B) with an acylating reagent in the presence of base. A typical reaction condition is to mix compound II(B) with excess of base, such as DIPEA in DCM and adding the resulting solution to an isocyanate at 0° C. The reaction in stirred for 2 hours and subsequent aqueous workup gives compound II(D). The ethyl ester protecting group on the pyrazole nitrogen of compound II(D) is removed to give compound of formula I. This can typically be done by treating compound II(D) with a base. A typical reaction condition is to reflux compound II(D) in dioxane and DCM in the presence of 2-3 equivalents of LiGH. Subsequent aqueous workup affords compound of formula I.

In the second route of Scheme 2, the Boc group on the pyrrole nitrogen is removed to give compound III(A). The reaction can typically be carried out by treating compound I(G) with a strong acid. A typical reaction condition is to treat compound I(G) with 4N HCl in dioxane and DCM. Subsequent aqueous workup affords compound III(A). Compound III(A) can then undergo a nucleophilic reaction with an (COR<sup>b</sup>) electrophile to give compound III(B). Because the —NH₂ group attached to the pyrazole in compound III(A) is less reactive than the pyrrole nitrogen of III(A), the transformation of III(A) to III(B) can be carried out without protecting the pyrazole —NH₂ group of compound III(A). The nucleophilic reaction carried out for this transformation can be an alkylation, acylation, sulfonylation, reductive amination. Relative mild reaction conditions are preferred to achieve the reaction selectivity. An acylation reaction of III(A) to give III(B) is carried out by treating compound III(A) with an acylating reagent in the presence of base. A typical reaction condition is to mix compound III(A) with excess of base, such as DIPEA in DCM and adding the resulting solution to an isocyanate at 0° C. The reaction mixture is held at 0° C. for about two hours and subsequent aqueous workup gives compound III(B).

Compound III(B) then undergoes a nucleophilic reaction with an $R^a$ electrophile moiety. This nucleophilic reaction can be an acylation, alkylation, sulfonylation, reductive amination or one of many other reactions that an amine functionality carries out. A typical acylation reaction condition is to treat compound III(B) with an acylating agent such as $R^a$—NCO in the presence of a base such as 2 equivalents of DIPEA in a solvent such as dichloromethane for 2 hours. Alternatively, III(B) can be treated with an acylating agent such as $R^a$—COOR, where R is an activating group such as p-nitrophenyl, in the presence of a base such as 2 equivalents of DIPEA, in a solvent such as 1,2-dichloroethane. Subsequent aqueous workup gives compound III(C). The ethyl ester protecting group on the pyrazole nitrogen of compound III(C) is removed typically with a base to give the free base compound I. A typical reaction condition is to mix compound III(C) with TEA in a protic solvent such as methanol followed by purification to give compound of formula I.

Alternatively, the ethyl ester protecting group on the pyrazole nitrogen of compound III(B) is removed to give the free base compound III(D). This can typically be done by treating compound III(B) with a base. A typical reaction condition is to reflux compound III(B) in dioxane and DCM in the presence of 2-3 equivalents of LiOH. Subsequent aqueous workup affords compound III(D). Compound III(D) then undergoes a nucleophilic reaction with an $R^a$ electrophile moiety. This nucleophilic reaction can be an acylation, alkylation, sulfonylation, reductive amination or one of many other reactions that an amine functionality carries out. A typical acylation reaction condition is to treating compound III(D) with an acylating agent such as $R^a$—COCl, in the presence of a base such as 2 equivalents of DIPEA in a solvent such as dichloromethane. The reaction mixture is stirred for four hours and subsequent aqueous workup and purification gives compound of formula I.

Any of the above compounds of formula (A) and (B) as defined above can be converted into another analogous compound by standard chemical manipulations. All starting materials, regents, and solvents are commercially available and are known to those of skill in the art unless otherwise stated. These chemical manipulations are known to those skilled in the art and include (a) removal of a protecting group by methods outlined in T. W. Greene and P. G. M. Wuts, *Protective Groups in Organic Synthesis*, 2nd Ed., John Wiley and Sons, New York, 1991; (b) displacement of a leaving group (halide, mesylate, tosylate, etc) with a primary or secondary amine, thiol or alcohol to form a secondary or tertiary amine, thioether or ether, respectively; (c) treatment of primary and secondary amines with an isocyanate, acid chloride (or other activated carboxylic acid derivative), alkyl/aryl chloroformate or sulfonyl chloride to provide the corresponding urea, amide, carbamate or sulfonamide; (d) reductive amination of a primary or secondary amine using an aldehyde.

The compounds of the present invention may have asymmetric carbon atoms. Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formula (A) or formula (B) that are basic in nature are capable of forming a wide variety of different salts with various inorganic and organic acids. Although such salts must be pharmaceutically acceptable for administration to animals, it is often desirable in practice to initially isolate the compound of formula (A) or formula (B) from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula (A) or formula (B) that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula (A) or formula (B). Such non-toxic base salts include those derived from such pharmacologically acceptable cations as sodium, potassium, calcium, and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are inhibitors of protein kinase C and preferably selectively inhibit beta-1, beta-2 and optionally alpha isozymes of protein kinase C. With respect to the beta-2 isozyme in particular, the compounds of the present invention have Ki values of less than 100 nM.

As an inhibitor of protein kinase C the compounds are useful in the treatment of conditions in which protein kinase C has demonstrated a role in the pathology. Conditions recognized in the art include: diabetes mellitus and its complications, cancer, ischemia, inflammation, central nervous system disorders, cardiovascular disease, Alzheimer's disease and dermatological disease.

Protein kinase C has been linked to several different aspects of diabetes. Excessive activity of protein kinase C has been linked to insulin signaling defects and therefore to the insulin resistance seen in Type II diabetes. Karasik, A. et al. *J. Biol. Chem.* 265: 10226-10231 (1990); Chen, K. S. et al. *Trans. Assoc. Am. Physicians* 104: 206-212 (1991); Chin, J. E. et al *J. Biol. Chem.* 268: 6338-6347 (1993). In addition, studies have demonstrated a marked increase in protein kinase C activity in tissues known to be susceptible to diabetic complications when exposed to hyperglycemic conditions. Lee, T. S. et al., *J. Clin. Invest.* 83: 90-94 (1989); Lee, T. S. et al. *Proc. Natl. Acad. Sci USA* 86: 5141-5145 (1989); Craven, P. A. and DeRubertis, F. R. *J. Clin. Invest.* 83: 1667-1675 (1989); Wolf, B. A. *J. Clin. Invest.* 87: 1643-1648 (1991).

Protein kinase C activity has long been associated with cell growth, tumor promotion and cancer. Rotenberg, S. A. and Weinstein, I. B. *Biochem. Mol. Aspects Sel. Cancer* 1: 25-73 (1991). Ahamd et al., *Molecular Pharmacology:* 43, 858-862 (1993). It is known that inhibitors of protein kinase C inhibitors are effective in preventing tumor growth in animals. Meyer, T. et al. *Int. J. Cancer* 43: 851-856 (1989); Akinagaka, S. et al. *Cancer Res.* 51: 4888-4892 (1991). More recently, the protein kinase Cβ inhibitor, Enzastauring (LY317615.HCl) was shown to have a direct tumor effect by inducement of apoptosis and suppression of proliferating cultured tumor cell, in particular on human glioblastoma and colon carcinoma. Graff et al, *Cancer Res.* 16: 7462-7469 (2005). The compounds of the present invention also act as multidrug reversal (MDR) agents making them effective compounds when administered in conjunction with other chemotherapeutic agents.

Protein kinase C inhibitors have been shown to block inflammatory responses such as neutrophil oxidative burst, CD3 down-regulation in T-lymphocytes, and phorbol-induced paw edema. Towemy, B. et al. *Biochem. Biophys. Res. Commun.* 171: 1087-1092 (199)); Mulqueen, M. J. et al. *Agents Actions* 37: 85-89 (1992). Accordingly, as inhibitors of PKC, the present compounds are useful in treating inflammation.

Protein kinase C activity plays a central role in the functioning of the central nervous system. Huang, K. P. *Trends Neurosci.* 12: 425-432 (1989). In addition, protein kinase C inhibitors have been shown to prevent the damage seen in focal and central ischemic brain injury and brain edema. Hara, H. et al. *J. Cereb. Blood Flow Metab.* 10: 646-653(1990); Shibata, S. et al. *Brain Res.* 594: 290-294 (1992). Protein kinase C has also been determined to be implicated in Alzheimer's disease. Shimohama, S. et al. *Neurology* 43: 1407-1413 (1993). Accordingly, the compounds of the present invention are useful in treating Alzheimer's disease and ischemic brain injury.

Protein kinase C activity also plays an important role in cardiovascular disease. Increased protein kinase C activity in the vasculature has been shown to cause increased vasoconstriction and hypertension. A known protein kinase C inhibitor prevented this increase. Bilder, G. E. et al. *J. Pharmacol. Exp. Ter.* 252: 526-430 (1990). Because protein kinase C inhibitors demonstrate inhibition of the neutrophil oxidative burst, protein kinase C inhibitors are also useful in treating cardiovascular ischemia and improving cardiac function following ischemia. Muid, R. E. et al. *FEBS Lett.* 293: 169-172 (1990); Sonoki, H. et al. *Kokyu-To Junkan* 37: 669-674 (1989). The role of protein kinase C in platelet function has also been investigated and as shown elevated protein kinase C levels being correlated with increased response to agonists. Bastyr III, E. J. and Lu, *J. Diabetes* 42: (Suppl. 1) 97A (1993). PKC has been implicated in the biochemical pathway in the platelet-activity factor modulation of microvascular permeability. Kobayashi et al., *Amer. Pius. Soc.* H1214-H1220 (1994). Potent protein kinase C inhibitors have been demonstrated to affect agonist-induced aggregation in platelets. Toullec, D. et al. *J. Biol. Chem.* 266: 15771-15781 (1991). Protein kinase C inhibitors also block agonist-induced smooth muscle cell proliferation. Matsumoto, H. and Sasaki, Y. *Biochem. Biophys, Res. Commun.* 158: 105-109 (1989). Therefore, the present compounds are useful in treating cardiovascular disease, atherosclerosis and restenosis.

Abnormal activity of protein kinase C has also been linked to dermatological disorders such as psoriasis. Horn, F. et al. *J. Invest. Dermatol.* 88: 220-222 (1987); Raynaud, F. and Evain-Brion, D. *Br. J. Dermatol.* 124: 542-546 (1991). Psoriasis is characterized by abnormal proliferation of keratinocytes. Known protein kinase C inhibitors have been shown to inhibit keratinocyte proliferation in a manner that parallels their potency as PKC inhibitors. Hegemann, L. et al. *Aarch. Dermatol. Res.* 283: 456-460 (1991); Bollag, W. B. et al. *J. Invest. Dermatol.* 100: 240-246 (1993). Accordingly, PKC inhibitors are useful in treating psoriasis.

The compounds of the invention are also isozyme-selective. The compounds preferentially inhibit protein kinase C beta-1 and beta-2 isozyme and optionally the alpha isozyme, over the remaining protein kinase C isozymes, i.e., gamma, delta, epsilon, zeta nad eta. Accordingly, compounds of the present invention inhibit beta-1 and beta-2 isozymes of protein kinase C, and optionally the alpha isozyme at much lower concentrations with minimal inhibition of the other PKC isozymes.

The compounds of the present invention are particularly useful in treating those disease states in which protein kinase C isozyme beta-1, beta-2, and optionally alpha, are associated. For example, the elevated blood glucose levels found in diabetes leads to an isozyme-specific elevation of the beta-2 isozyme in vascular tissues. *Proc. Natl Acad. Sci. USA* 89: 11059-11065 (1992). A diabetes-linked elevation of the beta isozyme in human platelets has been correlated with their altered response to agonists. Bastyr III, E. J. and Lu, *J. Diabetes* 42: (Suppl 1) 97A (1993). The human vitamin D receptor has been shown to be selectively phosphorylated by protein kinase C beta. This phosphorylation has been linked to alterations in the functioning of the receptor. Hsieh et al, *Proc. Natl. Acad. Sci. USA* 88: 931509319 (1991); Hsieh et al. *J. Biol. Chem.* 268: 15118-15126 (1993). In addition, recent work has shown that the beta-2 isozyme is responsible for erythroleukemia cell proliferation while the alpha isozyme is involved in megakaryocyte differentiation in these same cells. Murray et al., *J. Biol. Chem.* 268: 15847-15853 (1993).

In addition to the beta-1 and beta-2 isozymes discussed above, the protein kinase C alpha isozyme has been shown to have potential in the treatment of nephropathy: a PKC-alpha knockout mouse having STZ-induced diabetes showed improved nephropathy. Menne et al, *Diabetes* 53: 2101-2109 (2005). PKC alpha was implicated in heart contractility, Braz et al. *Nature Medicine* 10: 248-254 (2004); and also in the regulation of Akt activation and eNOS phosphorylation in endothelial cells. Partovian & Simons, *Cellular Signalling* 16: 951-957 (2004).

Assay

Protein Kinase C beta 2 (PKCpII) catalyzes the production of ADP from ATP that accompanies the phosphoryl transfer to the PKC Pseudosubstrate peptide (A→S, RFARKGSLRQKNV). This transfer is coupled to the oxidation of β-NADH through the activities of Pyruvate Kinase (PK) and Lactate Dehydrogenase (LDH). β-NADH conversion to NAD+ is monitored by the decrease in absorbance at 340 nm (e=6.22 $cm^{-1}$ $mM^{-1}$) using a Molecular Devices SPECTRA max PLUS spectrophotometer.

A typical assay was carried out on a 96-well, clear microtiter plate in a Molecular Devices spectrophotometer for 20 minutes at 30° C. in 0.1 mL of assay buffer containing 50 mM HEPES, pH 7.4, 5 nM PKC, 23 units of pyruvate kinase, 33 units of lactate dehydrogenase, 0.15 mM peptide, 0.1 mM ATP, 1 mM DTT, 4 mM PEP, 8 mM MgCl2, 0.3 mM NADH, 60 mM CaCl$_2$), 10 mg/mL PS, 50 ng/mL PMA, 7.5% DMSO and from about 10,000 nM to 0.169 nM compound inhibitor. Stock solutions of 3-sn-phosphatidyl-L-serine (PS) and phorbol-12-myristate-13-acetate (PMA) were sonicated for 30 seconds just prior to addition to assay buffer and assays were initiated by the addition of 100 µM ATP.

Steady-state kinetic parameters for the bi-bi kinase reaction were determined at saturating phospho-acceptor peptide substrate concentration (0.15 mM) by fitting initial velocity data to the Michaelis-Menten equation, $$v=V_{max}[S]/(K_M+[S])$$

where v is the measured initial velocity, $V_{max}$ is the maximal enzyme velocity, [S] is the ATP substrate concentration, and $K_M$ is the Michealis constant for ATP. Enzyme turnover values ($k_{cat}$) were calculated according to $k_{cat}=V_{max}[E]$, where [E] is the total enzyme concentration. Enzyme inhibition constants (apparent $K_i$ values) were determined by fitting initial velocities at variable inhibitor concentrations to a model for ATP competitive inhibition based on the Morrison equation). Morrison, J. F., *Biochim. Biophys Acta* 185: 269-286 (1969).

Pharmaceutical Compositions/Formulations, Dosaging and Modes of Administration

Methods of preparing various pharmaceutical compositions with a specific amount of active compound are known, or will be apparent, to those skilled in this art. In addition, those of ordinary skill in the art are familiar with formulation and administration techniques. Such topics would be discussed, e.g. in Goodman and Gilman's *The Pharmaceutical Basis of Therapeutics*, current ed., Pergamon Press; and *Remington's Pharmaceutical Sciences*, current ed., Mack Publishing, Co., Easton, Pa. These techniques can be employed in appropriate aspects and embodiments of the methods and compositions described herein. The following examples are provided for illustrative purposes only and are not meant to serve as limitations of the present invention.

The compounds of formula (A) and (B) may be provided in suitable topical, oral and parenteral pharmaceutical formulations for use in the treatment of PKCpII mediated diseases. The compounds of the present invention may be administered orally as tablets or capsules, as oily or aqueous suspensions, lozenges, troches, powders, granules, emulsions, syrups or elixirs. The compositions for oral use may include one or more agents for flavoring, sweetening, coloring and preserving in order to produce pharmaceutically elegant and palatable preparations. Tablets may contain pharmaceutically acceptable excipients as an aid in the manufacture of such tablets. As is conventional in the art these tablets may be coated with a pharmaceutically acceptable enteric coating, such as glyceryl monostearate or glyceryl distearate, to delay disintegration and absorption in the gastrointestinal tract to provide a sustained action over a longer period.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain active ingredients in admixture with excipients suitable for the manufacture of an aqueous suspension. Such excipients may be a suspending agent, such as sodium carboxymethyl cellulose, methyl cellulose, hydroxypropylmethyl cellulose, sodium alginate, polyvinylpyrrolidone, gum tragacanth and gum acacia; a dispersing or wetting agent that may be a naturally occurring phosphatide such as lecithin, a condensation product of ethylene oxide and a long chain fatty acid, for example polyoxyethylene stearate, a condensation product of ethylene oxide and a long chain aliphatic alcohol such as heptadecaethylenoxycetanol, a condensation product of ethylene oxide and a partial ester derived from a fatty acid and hexitol such as polyoxyethylene sorbitol monooleate or a fatty acid hexitol anhydrides such as polyoxyethylene sorbitan monooleate.

The pharmaceutical compositions may be in the form of a sterile injectable aqueous or oleagenous suspension. This suspension may be formulated according to know methods using those suitable dispersing or wetting agents and suspending agents that have been mentioned above. The sterile injectable preparation may also be formulated as a suspension in a non toxic perenterally-acceptable diluent or solvent, for example as a solution in 1,3-butanediol. Among the acceptable vehicles and solvents that may be employed are water, Ringers solution and isotonic sodium chloride solution. For this purpose any bland fixed oil may be employed including synthetic mono- or diglycerides. In addition fatty acids such as oleic acid find use in the preparation of injectables.

The compounds of formula (A) and (B) may also be administered in the form of suppositories for rectal administration of the drug. These compositions can be prepared by mixing the drug with a suitable non-irritating excipient that is solid at about 25 Celsius but liquid at rectal temperature and will therefore melt in the rectum to release the drug. Such materials include cocoa butter and other glycerides.

For topical use preparations, for example, creams, ointments, jellies solutions, or suspensions, containing the compounds of the present invention are employed.

The compounds of formula (A) and (B) may also be administered in the form of liposome delivery systems such as small unilamellar vesicles, large unilamellar vesicles and multimellar vesicles. Liposomes can be formed from a variety of phospholipides, such as cholesterol, stearylamine or phosphatidylcholines.

Dosage levels of the compounds of the present invention are of the order of about 0.5 mg/kg body weight to about 100 mg/kg body weight. A preferred dosage rate is between about 30 mg/kg body weight to about 100 mg/kg body weight. It will be understood, however, that the specific dose level for any particular patient will depend upon a number of factors including the activity of the particular compound being administered, the age, body weight, general health, sex, diet, time of administration, route of administration, rate of excretion, drug combination and the severity of the particular disease undergoing therapy. To enhance the therapeutic activity of the present compounds they may be administered concomitantly with other orally active antidiabetic compounds such as the sulfonylureas, for example, tolbutamide and the like.

For administration to the eye, a compound of the present invention is delivered in a pharmaceutically acceptable ophthalmic vehicle such that the compound is maintained in contact with the ocular surface for a sufficient time period to allow the compound to penetrate the cornea and/or sclera and internal regions of the eye, including, for example, the anterior chamber, posterior chamber, vitreous body, aqueous humor, vitreous humor, cornea, iris/ciliary body, lens, choroid/retina and sclera. The pharmaceutically acceptable ophthalmic vehicle may be an ointment, vegetable oil, or an encapsulating material. A compound of the invention may also be injected directly into the vitreous humor or aqueous humor.

Further, a compound may be also be administered by well known, acceptable methods, such as subtenon and/or subconjuctival injections. As is well known in the ophthalmic art, the macula is comprised primarily of retinal cones and is the region of maximum visual acuity in the retina. A Tenon's capsule or Tenon's membrane is disposed on the sclera. A conjunctiva covers a short area of the globe of the eye posterior to the limbus (the bulbar conjunctiva) and folds up (the upper cul-de-sac) or down (the lower cul-de-sac) to cover the inner areas of the upper eyelid and lower eyelid, respectively. The conjunctiva is disposed on top of Tenon's capsule. The sclera and Tenon's capsule define the exterior surface of the globe of the eye. For treatment of age related macular degeneration (ARMD), choroid neovascularization, retinopathies (such as diabetic retinopathy (including macular edema), retinopathy of prematurity), retinitis, uveitis, cystoid macular edema (CME), glaucoma, and other diseases or conditions of the posterior segment of the eye, it is preferable to dispose a depot of a specific quantity of an ophthalmically acceptable pharmaceutically active agent directly on the outer surface of the sclera and below Tenon's capsule. In addition, in cases of ARMD and CME it is most preferable to dispose the depot directly on the outer surface of the sclera, below Tenon's capsule, and generally above the macula.

The compounds may be formulated as a depot preparation. Such long-acting formulations may be administered by implantation (for example, subcutaneously or intramuscularly) intramuscular injection or by the above mentioned subtenon or intravitreal injection. Alternatively, the active ingredient may be in powder form for constitution with a suitable vehicle, e.g., sterile pyrogen-free water, before use.

Within particularly preferred embodiments of the invention, the compounds may be prepared for topical administration in saline (combined with any of the preservatives and antimicrobial agents commonly used in ocular preparations), and administered in eyedrop form. The solution or suspension may be prepared in its pure form and administered several times daily. Alternatively, the present compositions, prepared as described above, may also be administered directly to the cornea.

Within preferred embodiments, the composition is prepared with a muco-adhesive polymer which binds to cornea. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The preparation of preferred compounds of the present invention is described in detail in the following examples, but the artisan will recognize that the chemical reactions described may be readily adapted to prepare a number of other compounds of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

EXAMPLES

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The structures of the compounds are confirmed by either elemental analysis or NMR, where peaks assigned to the characteristic protons in the title compound are presented where appropriate. ¹H NMR shift (5H) are given in parts per million (ppm) down field from an internal reference standard.

The invention will now be described in reference to the following examples. These examples are not to be regarded as limiting the scope of the present invention, but shall only serve in an illustrative manner. Table 1 provides a full listing of the compounds of the present invention and includes relevant H NMR data and Ki values as available.

Example A1: N4-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine

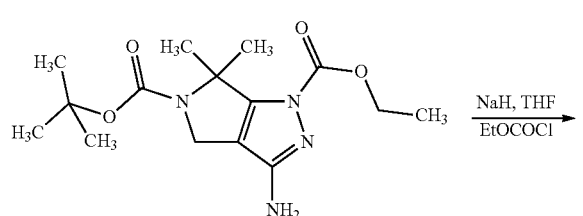

A1(i)

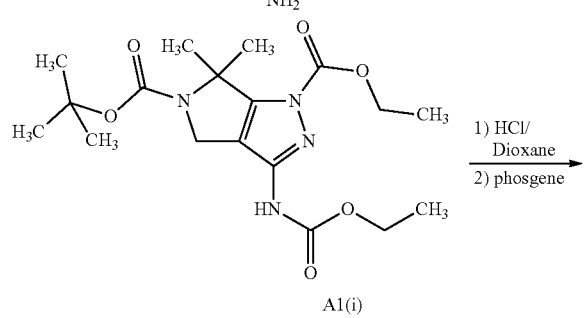

A1(ii)

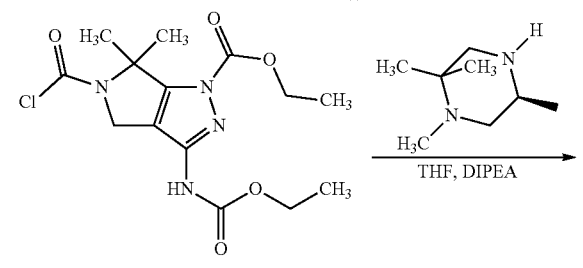

A1(iii)

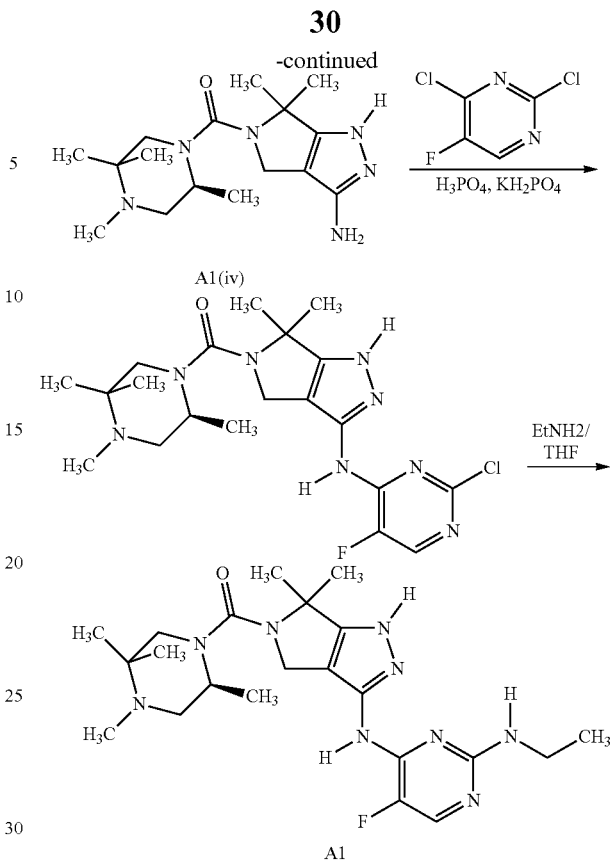

A1

Intermediate A1 (i): To a 0° C. solution of 5-tert-butyl 1-ethyl 3-amino-6,6-dimethyl-4,6-dihydropyrrolo[3,4-c]pyrazole-1,5-dicarboxylate (16.2 g, 49.9 mmol) in THF (100 mL) was added NaH (2.4 g, 59.9 mmol) in 3 portions. The reaction was stirred for 15 min in an ice bath, then ethyl chloroformate (6.5 g, 59.9 mmol) was added over 10 min. The reaction was warmed to room temperature and stirred for 16 h, then quenched with NH₄Cl (sat) and extracted with EtOAc (2×50 mL). The combined extracts were washed with brine then dried (MgSO₄) filtered and concentrated to give the desired compound A1(i) (19.8 g, 99%). Mass spectrum: Calcd for $C_{18}H_{29}N_4O_6$ (M+H): 397. Found 397.

Intermediate A1(ii): Ethyl 5-(chlorocarbonyl)-3-[(ethoxycarbonyl)amino]-6,6-dimethyl-5,6-dihydropyrrolo[3,4-c]pyrazole-1(4H)-carboxylate To a solution of A1(i) (19.8 g, 49.9 mmol) in dioxane (20 mL) was added HCl (60 mL, 4M in dioxane). The reaction was stirred at room temperature for 3 h then concentrated and dried under vacuum. The HCl salt of ethyl 3-[(ethoxycarbonyl)amino]-6,6-dimethyl-5,6-dihydropyrrolo[3,4-c]pyrazole-1(4H)-carboxylate was taken up in CH₂Cl₂ (60 mL). DIPEA (16.1 g, 125 mmol) was added and the reaction mixture was cooled in an ice bath. Phosgene (30 mL, 20% in toluene) was added slowly then the reaction was warmed to room temperature and run overnight. The reaction was concentrated then taken up in EtOAc (100 mL) and water (100 mL). The aqueous phase was extracted with EtOAc (2×25 mL) then the combined organic extracts were washed with brine, dried (MgSO₄), filtered and concentrated. The crude material was purified by silica gel column chromatography using CH₂Cl₂-2% 7N NH₃/MeOH in CH₂Cl₂ to give the title compound A1 (ii as a white solid (9.58 g, 54%). Mass spectrum: Calcd for $C_{14}H_{20}ClN_4O_5$ (M+H): 359. Found 359.

Intermediate A1(iii): Ethyl 3-[(ethoxycarbonyl)amino]-6,6-dimethyl-5-{[(2S)-2,4,5,5-tetramethylpiperazin-1-yl]carbonyl}-5,6-dihydropyrrolo[3,4-c]pyrazole-1(4H)-carboxylate To a sealed tube was added (5S)-1,2,2,5-tetramethylpiperazine (2.8 g, 20 mmol), DIPEA (7.63 g, 59.1 mmol) and THF (40 mL) followed by A1(ii (7.1 g, 20 mmol). The tube was sealed and placed in an oil bath at 80° C. and heated for 16 h. The reaction was cooled to room temperature then concentrated and purified by silica gel column chromatography using $CH_2Cl_2$-3% (7N $NH_3$/MeOH) in $CH_2Cl_2$ to give the title compound A1(i (4.62 g, 51%). Mass spectrum: Calcd for $C_{22}H_{37}N_6O_5$ (M+H): 465. Found 465.

Intermediate A1(iv): 6,6-dimethyl-5-{[(2S)-2,4,5,5-tetramethylpiperazin-1-yl]carbonyl}-1,4,5,6-tetrahydropyrrolo[3,4-c]pyrazol-3-amine To a microwave vial was added A1(iii) (4.6 g, 10 mmol), MeOH (45 mL) and LiGH (6.4 g, 40 mmol). The reaction was heated at 110° C. in the microwave for 20 min. The crude reaction mixture was concentrated and taken up in THF (75 mL). The insoluble material was filtered off and the filtrate was concentrated to give the title compound A1 (iv) (2.3 g, 72%). $^1$H NMR (300 MHz, CDCl$_3$) ppm 1.02 (s, 3H), 1.08-1.18 (m, 6H), 1.66 (s, 3H), 1.76 (s, 3H), 2.22 (s, 3H), 2.25-2.41 (m, 1H), 2.59-2.70 (m, 1H), 2.70-2.91 (m, 2H), 3.42-3.57 (m, 1H), 4.28-4.51 (m, 2H). Mass spectrum: Calcd for $C_{16}H_{29}N_6O$ (M+H): 321. Found 321.

Intermediate A1(v): N-(2-chloro-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine To a solution of A1 (iv) (1.92 g, 5.9 mmol) and 2,4-dichloro-5-fluoropyrimidine (1.0 g, 5.9 mmol) in DMSO (8 mL) was added potassium dihygrogenphosphate (0.82 g, 5.9 mmol) followed by $H_3PO_4$ (0.12 g, 1.2 mmol). The reaction was place in a 90° C. oil bath and heated for 20 h. The crude reaction was cooled to room temperature then poured into ice cold NaHCO$_3$ (30 mL) and extracted with EtOAc (2×30 mL). The combined organic extracts were washed with brine then dried (MgSO$_4$), filtered and concentrated. The crude solid was triturated with EtOAc then the filtrate was purified by silica gel column chromatography using 1%-4% 7N NH$_3$/MeOH in $CH_2Cl_2$ to provide the title compound A1(v) as a white solid (1.4 g, 53%). $^1$H NMR (300 MHz, DMSO-d$_6$) □□ ppm 0.90 (s, 3H), 1.00 (s, 3H), 1.06 (d, J=6.4 Hz, 3H), 1.58 (s, 3H), 1.69 (s, 3H), 2.08 (s, 3H), 2.14-2.25 (m, 1H), 2.55-2.64 (m, 2H), 2.73-2.89 (m, 1H), 3.38-3.51 (m, 1H), 4.51-4.72 (m, 2H), 7.95-8.45 (m, 1H), 10.68 (s, 1H), 11.81-12.75 (m, 1H). Mass spectrum: Calcd for $C_{20}H_{29}ClN_8O$ (M+H): 451. Found 451.

Example A1: N4-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine To a microwave vial was added A1(v)(200 mg, 0.44 mmol) and ethylamine (5 mL, 2M in MeOH). The vial was heated to 150° C. in the microwave for 1.5 h. The crude sample was concentrated then purified by silica gel column chromatography using 1%-4% 7N NH$_3$/MeOH in $CH_2Cl_2$ to give the desired product A1 as a yellow solid (161 mg, 79%). See Table 1 below for NMR data.

Examples A2-A9

Examples A2 through A9 were prepared using methods analogous to Example A1 above. See Table 1 below for names and NMR data Example A10: 5-{[(8S)-6,8-dimethyl-6,9-diazaspiro[4.5]dec-9-yl]carbonyl}-N-(5-fluoro-2-methylpyrimidin-4-yl)-6,6-dimethyl-1,4,5,6-tetrahydropyrrolo[3,4-c]pyrazol-3-amine

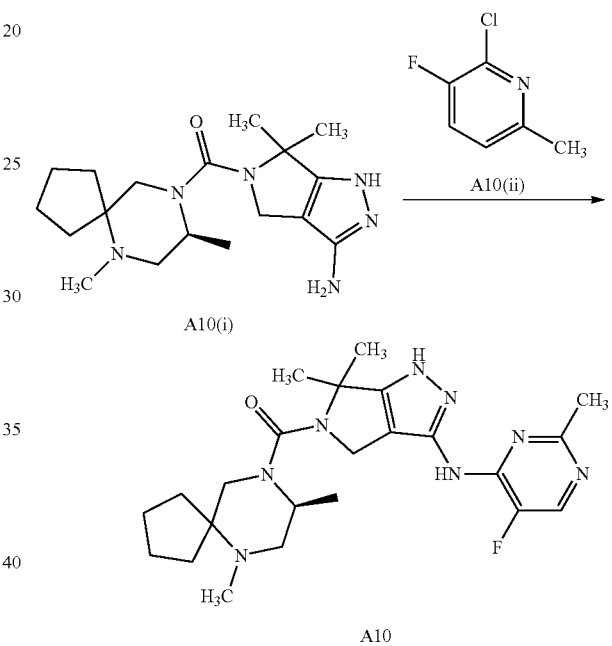

Intermediate A10(i): 5-{[(8S)-6,8-dimethyl-6,9-diazaspiro[4.5]dec-9-yl]carbonyl}-6,6-dimethyl-1,4,5,6-tetrahydropyrrolo[3,4-c]pyrazol-3-amine Using the same procedure as in the preparation of intermediate A1(iv) above, the titled intermediate was purified by flash chromatography eluting with methylene chloride containing 5% 7N NH$_3$ in methanol to a yellow solid (506 mg, 90%). For the synthesis of spiro cyclopentyl piperazine, please refer to the general synthesis of piperazines. 1H NMR (400 MHz, CHLOROFORM-d) δ ppm 1.13 (3H, d, J=6.32 Hz), 1.36-1.41 (1H, m), 1.52-1.64 (8H, m), 1.66 (3H, s), 1.77 (3H, s), 2.20-2.22 (3H, m), 2.23-2.29 (1H, m), 2.60 (1H, dd, J=11.75, 3.66 Hz), 2.78-2.89 (2H, m), 3.49 (2H, s), 3.52-3.56 (1H, m), 3.64 (1H, s), 4.33-4.44 (2H, m).

Intermediate A10(i): 4-Chloro-5-fluoro-2-methylpyrimidine

Sodium hydride (60%, 5.0 g, 125 mmol) was washed with hexane to remove the mineral oil and dried, then suspended in THF (50 mL) and cooled to 0° C. Ethyl fluoroacetate (13.30 g, 125 mmol) and ethyl formate (15.14 mL, 187 mmol) were mixed together and added to the stirring suspension. The reaction was slowly warmed to ambient temperature and stirred 3 days. The solvent was removed. A mixture of acetamidine hydrochloride (11.81 g, 125 mmol), sodium ethoxide (8.86 g, 125 mmol), and ethanol (60 mL) were added to the reaction followed by refluxing overnight. The ethanol was removed under reduced pressure. The residue was dissolved in a minimum of water and acidified to pH=6 with concentrated HCl. The crude products were then extracted by salting out from the aqueous phase and washing exhaustively with 4:1 $CHCl_3$/isopropanol. The combined organic phases were dried ($MgSO_4$) and evaporated. The crude solid was purified by silica gel chromatography eluting with 5-90% EtOAc/hexane to give a white solid (0.95 g, 6%). $R_f$=0.08 (75% EtOAc/hexane). $^1$H NMR (400 MHz, DMSO-$d_6$): δ 2.25 (d, J=1.0 Hz, 3H), 7.93 (d, J=3.8 Hz, 1H), 12.95 (br, 1H). LCMS 129. 2-Methyl-5-fluorouracil (1.04 g, 7.21 mmol) and N,N-dimethylaniline (1.80 mL) were heated in $POCl_3$ at 110° C. for 90 minutes. After cooling, the reaction was added carefully to ice. The product was extracted with diethylether. The ether layer was washed with sequentially with 2N HCl, water, and brine followed by drying ($MgSO_4$). The ether was carefully removed under reduced pressure to give a volatile liquid (0.39 g, 34%) which was used without further purification. $R_f$=0.26 (10% EtOAc/hexane). $^1$H NMR (400 MHz, DMSO-$d_6$): δ 3.91 (s, 3H), 8.79 (s, 1H).

Example A10: 5-{[(8S)-6,8-dimethyl-6,9-diazaspiro[4.5]dec-9-yl]carbonyl}-N-(5-fluoro-2-methylpyrimidin-4-yl)-6,6-dimethyl-1,4,5,6-tetrahydropyrrolo[3,4-c]pyrazol-3-amine Using the same procedure as described above for intermediate A1(v), title compound A10 was purified to a white powder (49.7 mg, 24%). See Table 1 below for NMR data.

Example A11: $N^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine

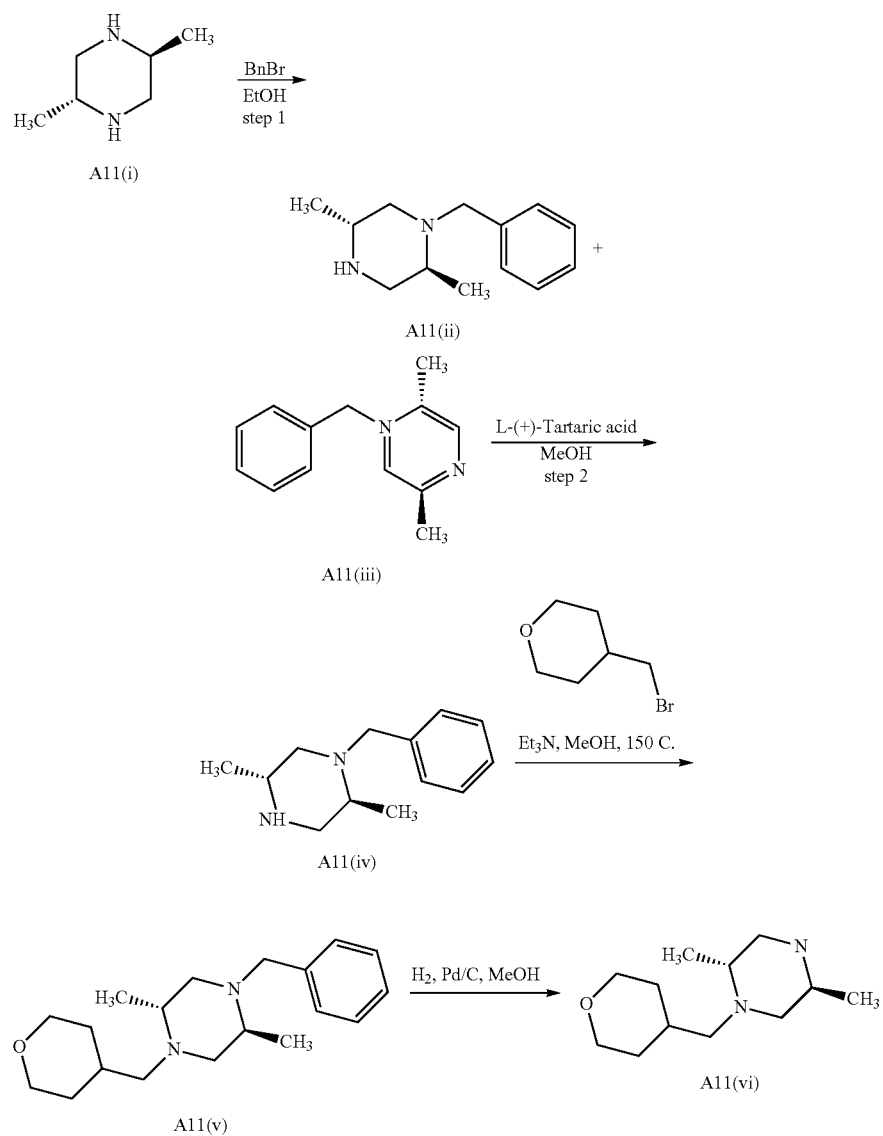

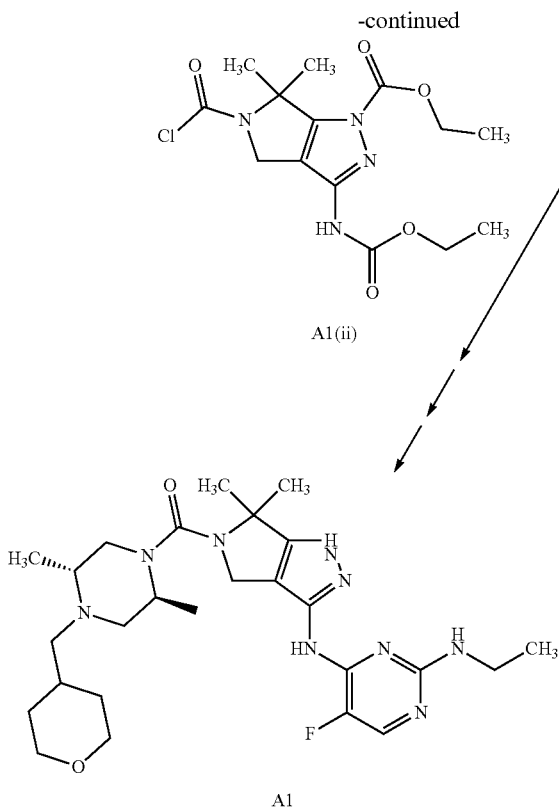

Intermediates A11(ii) and A11(iii): (2S,5R)-1-benzyl-2,5-dimethylpiperazine and A11(iii) ((2R,5S)-1-benzyl-2,5-dimethylpiperazine Compound A11(i) (800 g, 7 mol) was dissolved in 12.8 L of EtOH. A solution of benzyl bromide (1 kg, 5.8 mol) in 1.6 L of EtOH was added dropwise at room temperature. The reaction mixture was stirred at room temperature overnight. TLC (CH$_2$Cl$_2$: MeOH=10:1) showed the reaction was complete. The solvent was removed in vacuum. The residue was diluted with 32 L of water and the resulting mixture was stirred at room temperature for 30 minutes, then filtered. The filtrate was extracted with CH$_2$Cl$_2$ (8 L×3). The organic phase was dried over Na$_2$SO$_4$ and concentrated to dryness to give a mixture of compound A11(ii and A11 (iii) (800 g, 56%) as brown oil.

Intermediate A11(iv)
((2S,5R)-1-benzyl-2,5-dimethylpiperazine)

To a stirred solution of compound A11 (ii) and A11 (iii) (300 g, 1.48 mol) in MeOH (1 L) was added a solution of L-(+)-tartaric acid (444 g, 2.96 mol) in MeOH (2 L). After the mixture was stirred at room temperature for 20 minutes, then left standing at 0° C. for 24 hours. The solid formed was collected by filtration, which was re-crystallized from MeOH (2 L) to give a solid. The solid was dissolved in 1.6 L of water. The resulting mixture was basified to pH=9-10 with saturated aqueous Na$_2$CO$_3$. Then the mixture was extracted with CH$_2$Cl$_2$ (1.5 L×2). The organic phase was dried over Na$_2$SO$_4$ and concentrated to dryness to give A11 (iv) (122 g, 81%) as yellow liquid. $^1$H NMR (400 MHz, CDCl$_3$) δ 7.21-7.13 (m, 5H), 4.02 (d, 1H), 3.00 (d, 1H), 2.82-2.51 (m, 4H), 2.15 (m, 1H), 1.57 (m, 2H), 1.05 (d, 3H), 0.85 (d, 3H).

Intermediate A11(v): (2S,5R)-1-benzyl-2,5-dimethyl-4-(tetrahydro-2H-pyran-4-ylmethyl)piperazine To a microwave vial was added A11(iv) (7.50 g, 36.7 mmol), (bromomethyl)tetrahydropyran (6.57 g, 36.7 mmol), triethylamine (12.8 mL, 91.8 mmol), and MeOH (9 mL). The reaction mixture was heated to 150° C. for 2 hours in the microwave, at which time the resulting solid was triturated with MeOH, filtered, and dried to give the desired product as a white solid A11(v) (6.1 g, 55%). Mass Spectrum: Calcd for C$_{19}$H$_{31}$N$_2$O (M+H): 303. Found: 303.

Intermediate A11(vi): (2R,5S)-2,5-dimethyl-1-(tetrahydro-2H-pyran-4-ylmethyl)piperazine To a solution of A11(v) (6.10 g, 20.0 mmol) in MeOH (200 mL) was added 10% palladium on carbon (0.600 g, 0.570 mmol). The suspension was evacuated and backfilled with hydrogen (×3) and allowed to stir for 15 h under hydrogen. The suspension was filtered through celite, the filter cake washed with CH$_2$Cl$_2$, and the filtrate concentrated to give the desired product as a colorless oil A11 (vi) (4.3 g, 88%). Mass Spectrum: Calcd. for C$_{12}$H$_{25}$N$_2$O (M+H): 213. Found: 213.

Example A11: N⁴-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-N²-ethyl-5-fluoropyrimidine-2,4-diamine The title compound was prepared using methods analogous to Example A1 except that A11 (vi) was substituted in place of (5S)-1,2,2,5-tetramethylpiperazine. See Table 1 below for NMR data.

Example AA1: 5-{[(2S,5R)-4-ethyl-2,5-dimethylpiperazin-1-yl]carbonyl}-N-(5-fluoro-2-methoxypyrimidin-4-yl)-6,6-dimethyl-1,4,5,6-tetrahydropyrrolo[3,4-c]pyrazol-3-amine

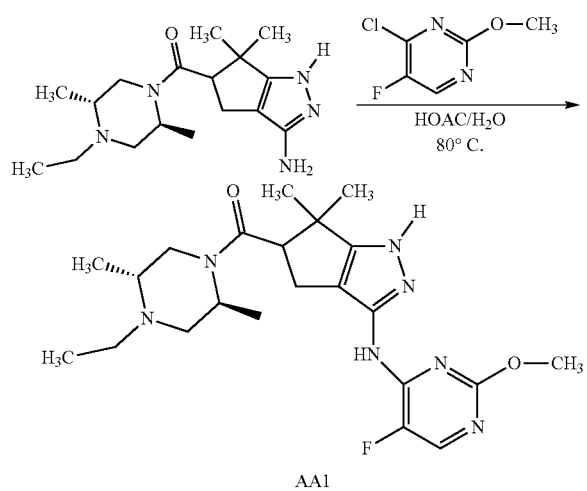

AA1

A solution of 5-{[(2S,5R)-4-ethyl-2,5-dimethylpiperazin-1-yl]carbonyl}-6,6-dimethyl-1,4,5,6-tetrahydropyrrolo[3,4-c]pyrazol-3-amine (289 mg, 0.9 mmol) and 4-chloro-5-fluoro-2-methoxypyrimidine (257 mg, 2 eq) in 5 mL of 50% acetic acid in water was heated in a microwave for 30 min at 80° C. Purification as described in Example A1 afforded the title compound AA1 as a white powder (13.1 mg, 3%). See Table 1 below for NMR data.

Examples AA2-AA5

Examples AA2 through AA5 were prepared using methods analogous to Example AM. See Table 1 below for names and NMR data.

Example B1: N²-ethyl-5-fluoro-N⁴-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine Acetate Salt

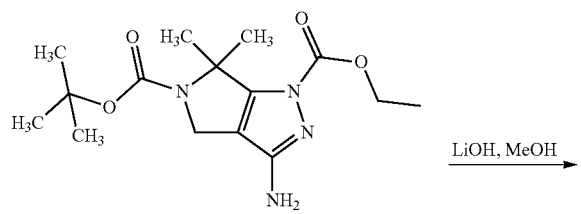

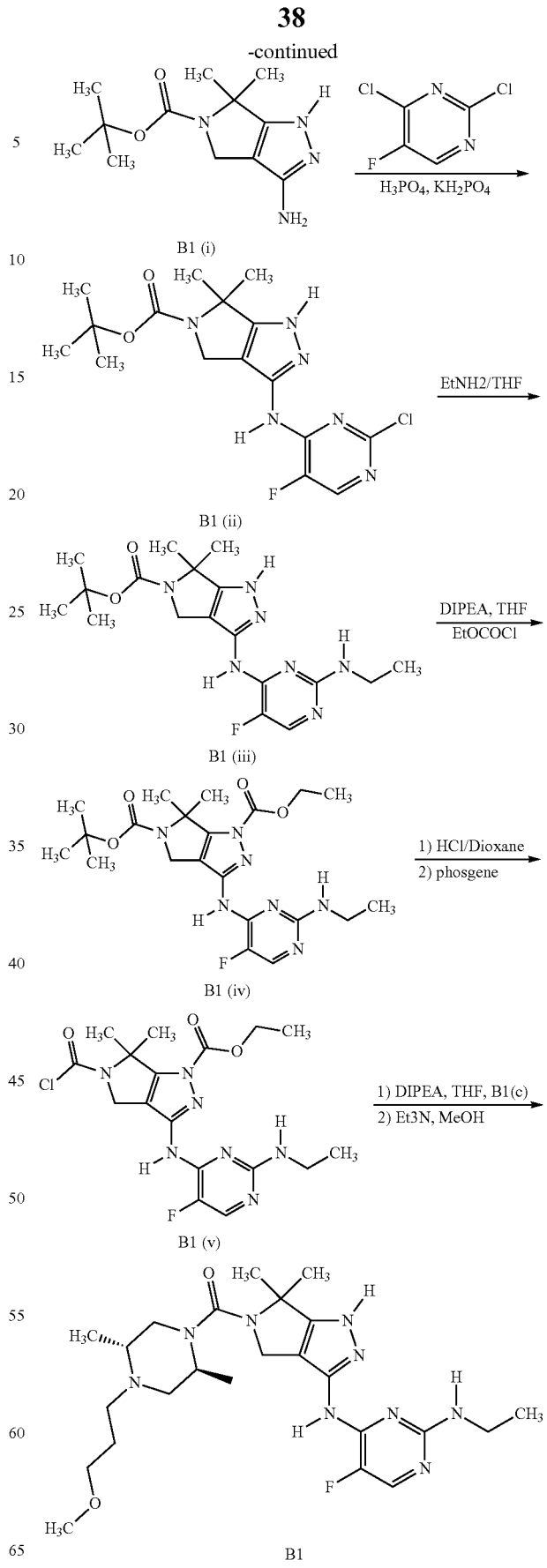

Intermediate B1(i): Tert-Butyl 3-amino-6,6-dimethyl-4,6-dihydropyrrolo[3,4-c]pyrazole-5(1H)-carboxylate To a slurry of 5-tert-butyl 1-ethyl 3-amino-6,6-dimethyl-4,6-dihydropyrrolo[3,4-c]pyrazole-1,5-dicarboxylate (25.00 g, 77.1 mmol) in MeOH (50 mL) was added LiOH (1.92 g, 77.1 mmol). The reaction was stirred at room temperature for 2 h then concentrated. The crude reaction mixture was taken up in EtOAc (50 mL) then washed with NaHCO$_3$ (20 mL) and water (20 mL). The organic layer was dried (MgSO$_4$), filtered and concentrated to give an orange solid which was triturated with ACN then filtered and rinsed with ACN (50 mL) to give the title compound B1(i) as a white solid (14.8 g, 76%). $^1$H NMR (300 MHz, DMSO-d$_6$) δ ppm 1.40-1.46 (m, 9H), 1.47-1.54 (m, 6H), 4.03-4.17 (m, 2H), 4.95 (br. s., 1H), 11.15 (s, 1H). Mass spectrum: Calcd for C$_{12}$H$_{21}$N$_4$O$_2$ (M+H): 253. Found 253.

Intermediate B1(ii): Tert-Butyl 3-[(2-chloro-5-fluoropyrimidin-4-yl)amino]-6,6-dimethyl-4,6-dihydropyrrolo[3,4-c]pyrazole-5(1H)-carboxylate To a solution of B1(i) (8.01 g, 31.7 mmol) and 2,4-dichloro-5-fluoro pyrimidine (5.30 g, 31.7 mmol) in DMSO (40 mL) was added potassium dihygrogenphosphate (4.32 g, 31.7 mmol) followed by H$_3$PO$_4$ (0.62 g, 6.4 mmol). The reaction was placed in a 95° C. oil bath and heated for 20 h. The crude reaction was cooled to room temperature then poured into ice cold NaHCO$_3$ (sat, 100 mL) followed by addition of EtOAc (75 mL). The resulting mixture was filtered to give the desired compound B1(ii) as a white solid (6.1 g, 50%). $^1$H NMR (300 MHz, DMSO-d$_6$) δ ppm 1.35-1.50 (m, 9H), 1.56-1.65 (m, 6H), 4.37-4.64 (m, 2H), 8.09-8.42 (m, 1H), 10.70 (br. s., 1H), 12.53 (br. s., 1H). Mass spectrum: Calcd for C$_{16}$H$_{21}$ClFN$_6$O$_2$ (M+H): 383. Found 383.

Intermediate B1(iii): Tert-Butyl 3-{[2-(ethylamino)-5-fluoropyrimidin-4-yl]amino}-6,6-dimethyl-4,6-dihydropyrrolo[3,4-c]pyrazole-5(1H)-carboxylate To a sealed tube was added B1(ii) (7.64 g, 20.0 mmol) and ethylamine (40.0 mL, 2M in MeOH). The sealed tube was heated in an oil bath at 150° C. for 16 h. The reaction was allowed to cool to room temperature and the resulting solid was filtered and rinsed with cold MeOH to give the title compound B1(iii) as a white solid (6.1 g, 78%). $^1$H NMR (300 MHz, DMSO-d$_6$) δ ppm 1.10 (t, J=7.2 Hz, 3H), 1.39-1.48 (m, 9H), 1.53-1.61 (m, 6H), 3.18-3.27 (m, 2H), 4.23-4.37 (m, 2H), 7.06 (br. s., 1H), 7.93 (s, 1H), 10.10 (br. s., 1H), 12.45 (br. s., 1H). Mass spectrum: Calcd for C$_{18}$H$_{27}$FN$_7$O$_2$ (M+H): 392. Found 392.

Intermediate B1(iv): 5-Tert-Butyl 1-ethyl 3-{[2-(ethylamino)-5-fluoropyrimidin-4-yl]amino}-6,6-dimethyl-4,6-dihydropyrrolo[3,4-c]pyrazole-1,5-dicarboxylate A solution of B1(iii) (5.14 g, 13.1 mmol) in THF (60 mL) and DIPEA (4.24 g, 13.1 mmol) was cooled in an ice bath then ethylchloroformate (1.42 g, 13.1 mmol) was added dropwise. The reaction mixture was slowly warmed to room temperature and stirred for 5 h, then quenched with water (50 mL) and extracted with EtOAc (2×100 mL). The combined extracts were washed with brine (50 mL) then dried (MgSO$_4$), filtered and concentrated. The crude material was purified by silica gel column chromatography using 10-40% EtOAC in CH$_2$Cl$_2$ to provide the title compound B1(iv) as a white foam (5.8 g, 95%). $^1$H NMR (300 MHz, DMSO-d$_6$) δ ppm 1.01-1.11 (m, 3H), 1.33 (t, J=7.2 Hz, 3H), 1.38-1.49 (m, 9H), 1.70-1.83 (m, 6H), 3.13-3.27 (m, 2H), 4.28-4.50 (m, 4H), 6.54-6.86 (m, 1H), 7.94 (m, 1H), 10.06-10.41 (m, 1H). Mass spectrum: Calcd for C$_{21}$H$_{31}$FN$_7$O$_4$ (M+H): 464. Found 464.

Intermediate B1(v): Ethyl 5-(chlorocarbonyl)-3-{[2-(ethylamino)-5-fluoropyrimidin-4-yl]amino}-6,6-dimethyl-5,6-dihydropyrrolo[3,4-c]pyrazole-1(4H)-carboxylate To a suspension of B1(iv) (4.43 g, 9.6 mmol) in dioxane (25 mL) was added HCl (20 mL, 4M in dioxane). The reaction was stirred at room temperature for 2 h then concentrated. To a solution of the HCl salt of ethyl 3-{[2-(ethylamino)-5-fluoropyrimidin-4-yl]amino}-6,6-dimethyl-5,6-dihydropyrrolo[3,4-c]pyrazole-1(4H)-carboxylate (1.27 g, 2.7 mmol) in CH$_2$Cl$_2$ (40 mL) was added DIPEA (1.57 g, 12.1). The reaction was cooled to −78° C. and triphosgene (0.48 g, 0.6 mmol) was added in a solution of CH$_2$Cl$_2$ (10 mL) with an addition funnel over 15 min. The reaction was quenched at −78° C. with water then warmed to room temperature. The mixture was made to pH 8-9 with NaHCO$_3$ and extracted with CH$_2$Cl$_2$ (2×15 mL). The combined extracts were washed with brine (15 mL) then dried, filtered and concentrated. The crude material was purified by silica gel column chromatography using 0-3%7N NH$_3$/MeOH in CH$_2$Cl$_2$ to give the desired compound B1 (v) as a white foam (489 mg, 36%). $^1$H NMR (300 MHz, DMSO-d$_6$) δ ppm 1.07 (t, J=7.2 Hz, 3H), 1.33 (t, J=7.2 Hz, 3H), 1.78-1.84 (m, 6H), 3.12-3.28 (m, 2H), 4.42 (q, J=7.2 Hz, 2H), 4.78 (s, 2H), 6.69-6.97 (m, 1H), 7.77-8.08 (m, 1H), 10.41 (s, 1H). Mass spectrum: Calcd for C$_{17}$H$_{22}$ClFN$_7$O$_3$ (M+H): 426. Found 426.

Preparation of Side-Chain B1(c):

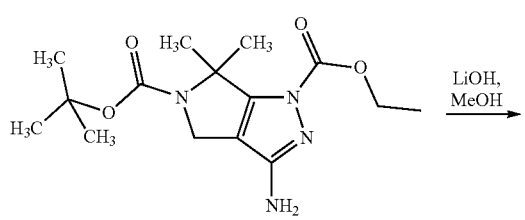

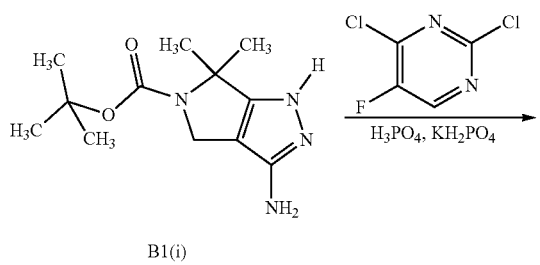

B1(i)

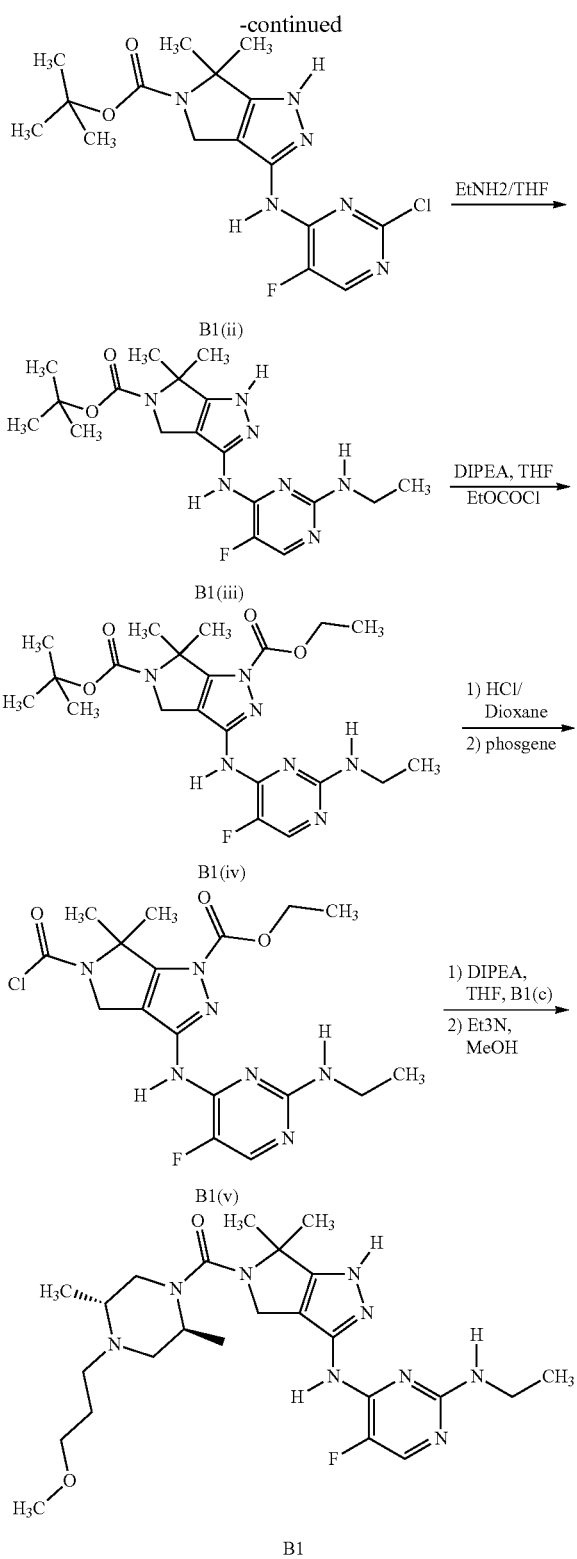

Intermediate B1 (a): (2S,5R)-1-benzyl-2,5-dimethylpiperazine

To a solution of starting material (3.00 g, 9.85 mmol) in $CH_2Cl_2$ (100 mL) was added 4 N HCl in 1,4-dioxane (20 mL). The solution was stirred for 1 hour, at which time the volatiles were removed in vacuo to yield the desired product as a white solid in quantitative yield. Mass Spectrum: Calcd for $C_{13}H_{21}N_2$ (M+H): 205. Found: 205.

Intermediate B1 (b): (2S,5R)-1-benzyl-4-(3-methoxypropyl)-2,5-dimethylpiperazine To a microwave vial was added starting material (1.60 g, 5.77 mmol), 1-bromo-3-methoxypropane (3.09 g, 20.2 mmol), triethylamine (6.03 mL, 43.3 mmol), THF (6 mL), and MeOH (6 mL). The suspension was heated at 150° C. in the microwave for 2 hours. The cooled solution was diluted with EtOAc (20 mL) and the organic layer washed with $NaHCO_3$ (sat., aq.) (3×25 mL) and brine (1×25 mL). The organic layer was dried over $MgSO_4$ and concentrated to give the desired product as brown oil (1.5 g, 92%). Mass Spectrum: Calcd for $C_{17}H_{29}N_2O$ (M+H): 277. Found: 277.

Intermediate B1 (c): (2R,5S)-1-(3-methoxypropyl)-2,5-dimethylpiperazine

To a solution of starting material (1.50 g, 5.43 mmol) in MeOH (50 mL) was added 10% palladium on carbon (0.150 g, 1.41 mmol). The suspension was evacuated and backfilled with hydrogen (×3) and allowed to stir for 15 h under hydrogen. The suspension was filtered through Celite, the filter cake washed with $CH_2Cl_2$, and the filtrate concentrated to give the desired product as a brown foam (0.83 g, 82%). Mass Spectrum: Calcd. for $C_{10}H_{23}N_2O$ (M+H): 187. Found: 187.

Example B1: $N^2$-ethyl-5-fluoro-$N^4$-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine Acetate Salt To a sealed tube was added B1(v) (393 mg, 0.92 mmol) in a solution of THF (10 mL) followed by DIPEA (537 mg, 4.2 mmol) and B1(c) (172 mg, 0.92 mmol). The reaction was placed in an 85° C. oil bath and heated for 16 h. The crude reaction was concentrated then taken up in MeOH (5 mL) and $Et_3N$ (5 mL) then stirred for an addition 16 h. Preparative HPLC using 5-50% $ACN/H_2O$ (0.1% AcOH) provided the title compound B1 as a white solid (185 mg, 36%). See Table 1 below for NMR data.

Examples B2-B5

Examples B2 to B5 were prepared using methods analogous to Example B1 above. See Table 1 below for names and NMR data.

Example B6: 4-[(6,6-dimethyl-5-{[(2S,5R)-2,4,5-trimethylpiperazin-1-yl]carbonyl}-1,4,5,6-tetrahydropyrrolo[3,4-c]pyrazol-3-yl)amino]pyrimidine-2-carbonitrile Example B6 was prepared using methods analogous to Example B1 above except that (2R, 5S)-1,2,5-trimethylpiperazine hydrochloride was substituted in place of intermediate B1 (b) and 4-chloropyrimidine-2-carbonitrile was substituted in place of 2,4-dichloro-5-fluoropyrimidine during the preparation of intermediate B1(ii). See Table 1 below for NMR data.

Example B7: N-(5-fluoro-2-morpholin-4-ylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine Example B7 was prepared using methods analogous to Example B1 above except that (2R,5S)-1,2,5-trimethylpiperazine hydrochloride was substituted in place of intermediate B1 (b) and morpholine was substituted in place of ethylamine during the preparation of intermediate B1(iii). See Table 1 below for NMR data.

Example C1: N²-ethyl-5-fluoro-N⁴-{5-[(4-fluoro-1-methylpiperidin-4-yl)carbonyl]-6,6-dimethyl-1,4,5,6-tetrahydropyrrolo[3,4-c]pyrazol-3-yl}pyrimidine-2,4-diamine

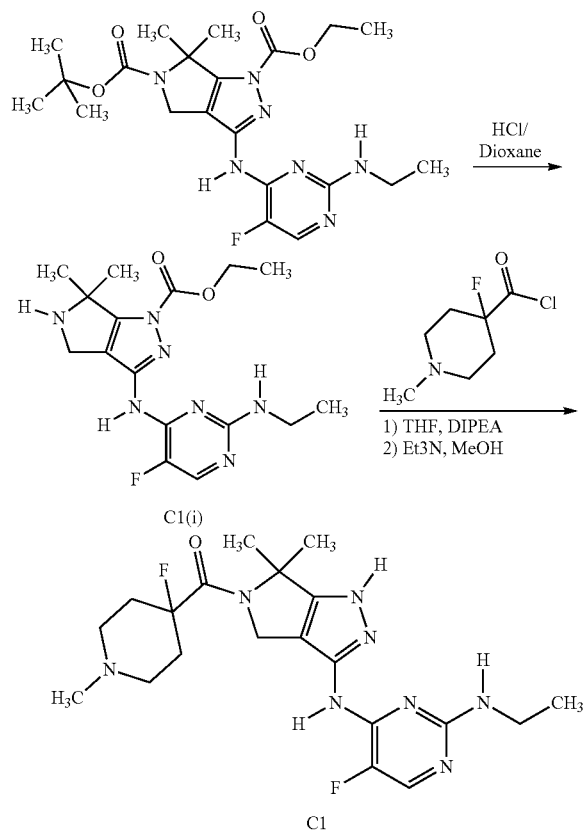

Intermediate C1(i): Ethyl 3-{[2-(ethylamino)-5-fluoropyrimidin-4-yl]amino}-6,6-dimethyl-5,6-dihydropyrrolo[3,4-c]pyrazole-1(4H)-carboxylate To a suspension of 5-tert-butyl 1-ethyl 3-{[2-(ethylamino)-5-fluoropyrimidin-4-yl]amino}-6,6-dimethyl-4,6-dihydropyrrolo[3,4-c]pyrazole-1,5-dicarboxylate (4.43 g, 9.6 mmol) in dioxane (25 mL) was added HCl (20 mL, 4M in dioxane). The reaction was stirred at room temperature for 2 h then concentrated to give the title compound C1(i) as the tri HCl salt (3.8 g, 84%). Mass spectrum: Calcd for $C_{16}H_{23}FN_7O_2$ (M+H): 364. Found 364.

Example C1: N²-ethyl-5-fluoro-N⁴-{5-[(4-fluoro-1-methylpiperidin-4-yl)carbonyl]-6,6-dimethyl-1,4,5,6-tetrahydropyrrolo[3,4-c]pyrazol-3-yl}pyrimidine-2,4-diamine To a sealed tube was added $C_1(i)$ (400 mg, 0.85 mmol) in a solution of THF (10 mL) followed by DIPEA (492 mg, 3.8 mmol) and 4-fluoro-1-methylpiperidine-4-carbonyl chloride (228 mg, 1.3 mmol). The reaction was heated in an oil bath at 80° C. for 16 h then concentrated and taken up in MeOH (3 mL) and $Et_3N$ (5 mL) and stirred for an addition 10 h. The crude reaction was concentrated then purified by silica gel column chromatography using 1-3% 7N $NH_3$/MeOH in $CH_2Cl_2$ to give the title compound $C_1$ as a yellow solid (175 mg, 47%). See Table 1 below for NMR data.

Example D1: N-(2-ethyl-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine

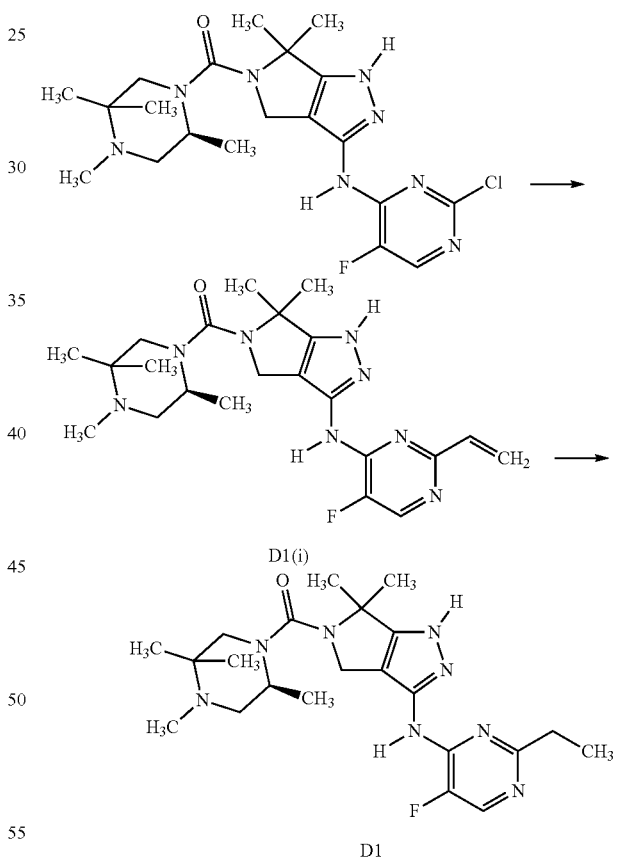

Intermediate D1(i): N-(5-fluoro-2-vinylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine To a septum capped sealed tube was added N-(2-chloro-5-fluoropyrimidin-4-yl)-6,6-dimethyl-5-{[(2S)-2,4,5,5-tetramethylpiperazin-1-yl]carbonyl}-1,4,5,tetrahydropyrrolo[3,4-c]pyrazol-3-amine (109 mg, 0.242 mmol), 4,4,5,5- tetramethyl-2-vinyl-1,3,2 dioxaborolane (122 mg, 0.725 mmol), Na$_2$CO$_3$ (77 mg, 0.73 mmol) and dichloro[1,1'-bis(diphenylphosphino)ferrocene]palladium(II) dichloromethane adduct (40 mg, 0.048 mmol) followed by DME (2.5 mL) and water (0.5 mL). The reaction mixture was purged with argon for 2 min. then placed in a preheated 100° C. oil bath and stirred for 16 h. The crude reaction was concentrated, taken up in EtOAc (15 mL) and washed with water (10 mL). The EtOAc solution was dried (MgSO$_4$), filtered and concentrated. Purification by silica gel column chromatography using 1-3% 7N NH$_3$/MeOH in CH$_2$Cl$_2$ provided the title compound D1(i) as a yellow solid (45 mg, 42%). $^1$H NMR (300 MHz, CDCl$_3$) δ ppm 0.99 (s, 3H), 1.05 (s, 3H), 1.18 (d, J=6.4 Hz, 3H), 1.72 (s, 3H), 1.83 (s, 3H), 2.19 (s, 3H), 2.25-2.36 (m, 1H), 2.63-2.75 (m, 1H), 2.76-2.95 (m, 2H), 3.52-3.73 (m, 1H), 4.57-4.81 (m, 2H), 5.65 (m, 1H), 6.40 (m, 1H), 6.76 (m, 1H), 8.13-8.31 (m, 1H), 8.53 (s, 1H). Mass spectrum: Calcd for C$_{22}$H$_{32}$FN$_8$O (M+H): 443. Found 443.

Example D1: N-(2-ethyl-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine To a nitrogen purged flask containing D1(i) (54 mg, 0.12 mmol) was added Pd/C (6.5 mg, 0.006 mmol) and MeOH (3 mL). A H2 balloon was applied and the reaction was stirred for 16 h. The crude mixture was poured over a bed of Celite and rinsed with MeOH (30 mL) then concentrated and purified by column chromatography using 1-3% 7N NH$_3$/MeOH in CH$_2$Cl$_2$ to provide the title compound D1 as a pale yellow solid (33 mg, 61%). See Table 1 below for NMR data.

Example E1: N-(2-ethyl-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine Acetate Salt

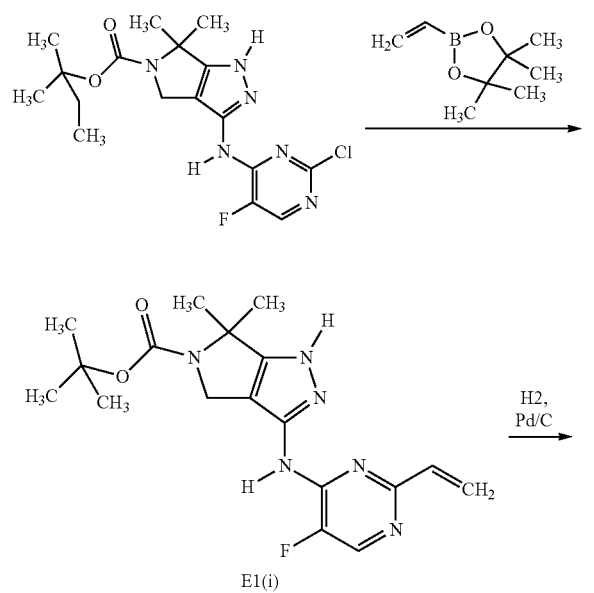

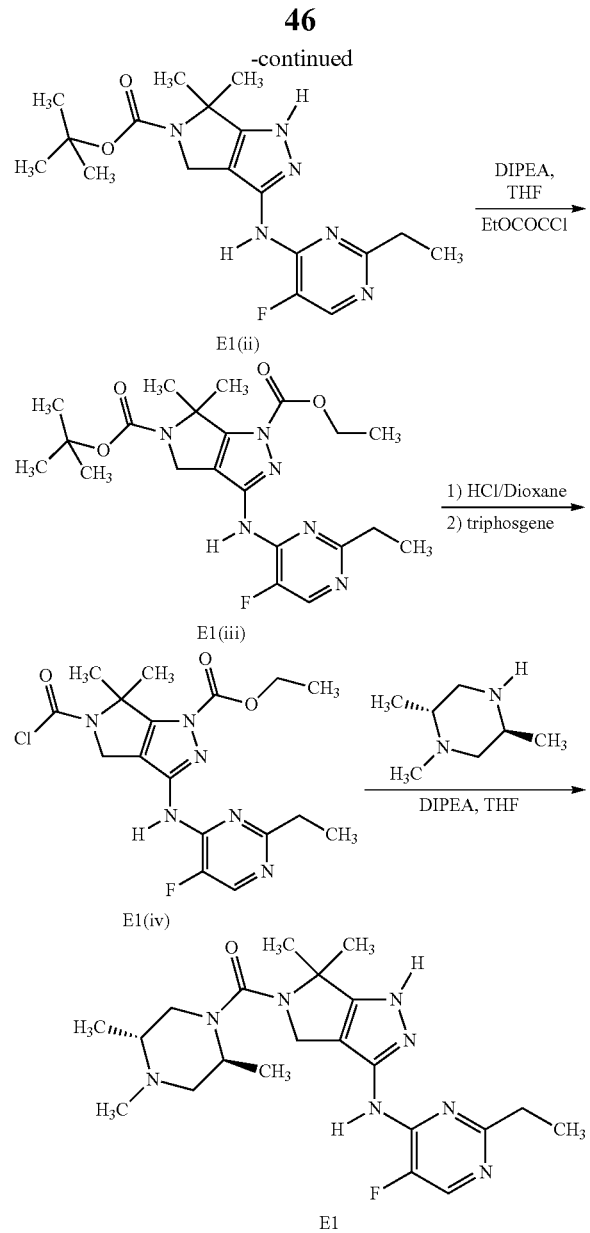

Intermediate E1(i): Tert-Butyl 3-[(5-fluoro-2-vinylpyrimidin-4-yl)amino]-6,6-dimethyl-4,6-dihydropyrrolo[3,4-c]pyrazole-5(1H)-carboxylate To a septum capped sealed tube was added tert-butyl 3-[(2-chloro-5-fluoropyrimidin-4-yl)amino]-6,6-dimethyl-4,6-dihydropyrrolo[3,4-c]pyrazole-5(1H)-carboxylate (2.00 g, 5.22 mmol), 4,4,5,5-tetramethyl-2-vinyl-1,3,2 dioxaborolane (2.41 g, 15.7 mmol), Na$_2$CO$_3$ (1.66 g, 15.7 mmol) and dichloro[1,1'-bis(diphenylphosphino)ferrocene]palladium (II) dichloromethane adduct (850 mg, 1.04 mmol) followed by DME (50 mL) and water (12 mL). The reaction mixture was purged with argon for 2 min. then placed in a preheated 100° C. oil bath and stirred for 16 h. The crude reaction was concentrated then taken up in EtOAc (100 mL) and washed with water (50 mL). The EtOAc solution was dried (MgSO$_4$), filtered and concentrated. Purification was performed by silica gel column chromatography using 1-10% 7N NH$_3$/MeOH in CH$_2$Cl$_2$ to provided the desired compound E1(i) as an orange solid (1.8 g, 91%). $^1$H NMR (300 MHz, CDCl$_3$) δ ppm 1.45-1.58 (m, 9H), 1.65-1.78 (m, 6H), 4.45-4.71 (m, 2H), 5.58-5.71 (m, 1H), 6.34-6.46 (m, 1H), 6.68-6.82 (m, 1H), 7.99 (s, 1H), 8.12-8.32 (m, 1H). Mass spectrum: Calcd for C$_{18}$H$_{24}$FN$_6$O$_2$ (M+H): 375. Found 375.

Intermediate E1 (ii): Tert-Butyl 3-[(2-ethyl-5-fluoropyrimidin-4-yl)amino]-6,6-dimethyl-4,6-dihydropyrrolo[3,4-c]pyrazole-5(1H)-carboxylate To a nitrogen purged flask containing E1(i) (1.71 g, 4.50 mmol) was added Pd/C (241 mg, 0.277 mmol) and MeOH (30 mL). A H$_2$ balloon was applied and the reaction was stirred for 16 h. The crude mixture was poured over a bed of Celite and rinsed with MeOH (75 mL) then concentrated. The dark brown solid was triturated with Et$_2$O (35 mL) to give the title compound E1(ii) as an off-white solid (1.02 g, 60%). $^1$H NMR (300 MHz, DMSO-d$_6$) δ ppm 1.21 (t, J=7.5 Hz, 3H), 1.40-1.49 (m, 9H), 1.52-1.65 (m, 6H), 2.60-2.87 (m, 2H), 4.37-4.68 (m, 2H), 8.01-8.55 (m, 1H), 9.75-10.42 (m, 1H), 11.60-12.54 (m, 1H). Mass spectrum: Calcd for C$_{18}$H$_{26}$FN$_6$O$_2$ (M+H): 377. Found 377.

Intermediate E1 (iii): 5-Tert-Butyl 1-ethyl 3-[(2-ethyl-5-fluoropyrimidin-4-yl)amino]-6,6-dimethyl-4,6-dihydropyrrolo[3,4-c]pyrazole-1,5-dicarboxylate A solution of E1(ii) (1.00 g, 2.66 mmol) in THF (40 mL) and DIPEA (858 mg, 6.64 mmol) was cooled in an ice bath. Ethyl chloroformate (317 mg, 2.92 mmol) was added and the reaction was warmed to room temperature and stirred for 16 h. The reaction was quenched with water (50 mL) and extracted with EtOAc (2×100 mL). The combined extracts were washed with brine (50 mL) then dried (MgSO4), filtered and concentrated. Purification was performed by silica gel column chromatography using 0-40% EtOAc in CH$_2$Cl$_2$ to give the title compound E1(iii) as a yellow solid (879 mg, 74%). $^1$H NMR (300 MHz, CDCl$_3$) δ ppm 1.28-1.34 (m, 3H), 1.47 (t, J=7.2 Hz, 3H), 1.50-1.56 (m, 9H), 1.79-1.90 (m, 6H), 2.75-2.87 (m, 2H), 4.45-4.56 (m, 2H), 4.74-4.77 (m, 2H), 7.65 (s, 1H), 8.06-8.31 (m, 1H). Mass spectrum: Calcd for C$_{21}$H$_{30}$FN$_6$O$_4$ (M+H): 449. Found 449.

Intermediate E1(iv): Ethyl 5-(chlorocarbonyl)-3-[(2-ethyl-5-fluoropyrimidin-4-yl)amino]-6,6-dimethyl-5,6-dihydropyrrolo[3,4-c]pyrazole-1(4H)-carboxylate To a suspension of E1(iii) (879 mg, 1.96 mmol) in dioxane (5 mL) was added HCl (10 mL, 4M in dioxane). The reaction was stirred at room temperature for 2 h then concentrated. The di HCl salt was taken up in CH$_2$Cl$_2$ (40 mL) and DIPEA (1.27 g, 9.8 mmol) was added then the reaction was cooled to −78° C. and triphosgene (0.41 g, 1.37 mmol) in a solution of CH$_2$Cl$_2$ (10 mL) was added slowly with an addition funnel over 15 min. The reaction was quenched at −78 C with water then warmed to room temperature. The mixture was made to pH 8-9 with NaHCO$_3$ and extracted with CH$_2$Cl$_2$ (2×15 mL). The combined extracts were washed with brine (15 mL) then dried, filtered and concentrated. The crude material was purified by silica gel column chromatography using 0-3%7N NH$_3$/MeOH in CH$_2$Cl$_2$ to give the title compound E1(iv) as a white solid (244 mg, 31%). $^1$H NMR (300 MHz, DMSO-d$_6$) δ ppm 1.19-1.30 (m, 3H), 1.32-1.42 (m, 3H), 1.69 (s, 6H), 2.67-2.95 (m, 2H), 4.47 (q, J=7.0 Hz, 2H), 4.66-5.51 (m, 2H), 8.27-8.76 (m, 1H), 9.73-10.36 (m, 1H). Mass spectrum: Calcd for C$_{17}$H$_{21}$ClFN$_6$O$_3$ (M+H): 411. Found 411.

Example E1: N-(2-ethyl-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine Acetate Salt To a sealed tube was added E1(iv) (200 mg, 0.487 mmol), DIPEA (283 mg, 2.19 mmol) and THF (10 mL). The tube was placed in a 90° C. oil bath and heated for 16 h. The reaction was concentrated then taken up in MeOH (5 mL) and Et$_3$N (5 mL) and stirred at room temperature for an additional 16 h. Preparative HPLC was performed using 5-50% ACN (0.1% AcOH) to give the title compound E1 as the acetate salt (61 mg, 26%). See Table 1 below for NMR data.

Examples E2 and E3

Examples E2 and E3 were prepared using methods analogous to Example E1 above. See Table 1 below for names and NMR data.

Example E4: 5-{[(2S,5R)-2,5-dimethyl-4-(3,3,3-trifluoropropyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine

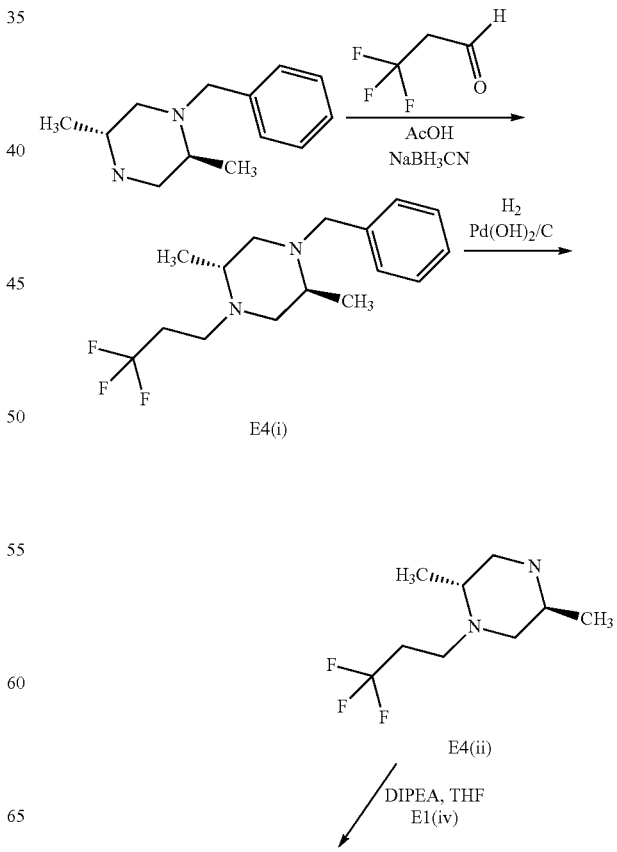

Intermediate E4(i): (2S,5R)-1-benzyl-2,5-dimethyl-4-(3,3,3-trifluoropropyl)piperazine To a solution of (2S,5R)-1-benzyl-2,5-dimethylpiperazine (2.00 g, 7.21 mmol) in THF (10 mL), MeOH (10 mL), and TEA (1.0 mL) was added 3,3,3-trifluoropropionaldehyde (1.62 g, 14.4 mmol) and AcOH (0.826 mL, 14.4 mmol) followed by sodium cyanoborohydride (0.907 g, 14.4 mmol). The reaction was allowed to stir for 2 h, at which time the reaction was quenched with water (15 mL) then made basic with NaHCO$_3$ and extracted with EtOAc. The organic layer was washed with brine, dried and concentrated in vacuo to yield a white powder (2.0 g, 90%). Mass Spectrum: Calcd for $C_{16}H_{24}N_2F_3$ (M+H): 301. Found: 301.

Intermediate E4(ii): (2R,5S)-2,5-dimethyl-1-(3,3,3-trifluoropropyl)piperazine To a solution of E4(i)(1.90 g, 6.30 mmol) in MeOH (20 mL) was added Pd(OH)$_2$ (1.00 g, 7.10 mmol). The suspension was evacuated/backfilled with hydrogen (×3) and allowed to stir for 15 h under hydrogen. The suspension was filtered through Celite, the filter cake washed with CH$_2$Cl$_2$, and the filtrate concentrated to yield a white solid (1.3 g, 96%). Mass Spectrum: Calcd for $C_9H_{18}N_2F_3$ (M+H): 211. Found: 211.

Example E4: 5-{[(2S,5R)-2,5-dimethyl-4-(3,3,3-trifluoropropyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine Example E4 was prepared using methods analogous to Example E1 above, except that intermediate E4(ii) was substituted in place of (2R,5S)-1,2,5-trimethylpiperazine hydrochloride. See Table 1 below for NMR data.

Example E5: 2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol

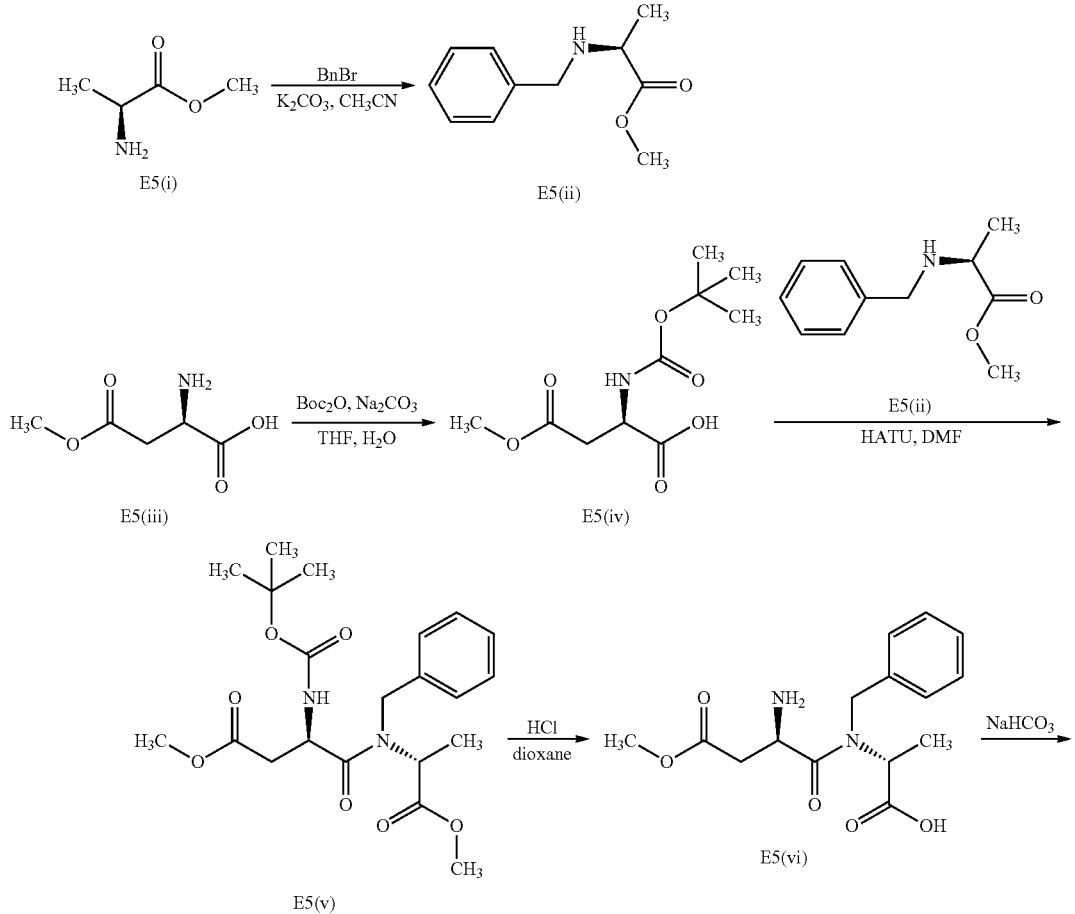

-continued
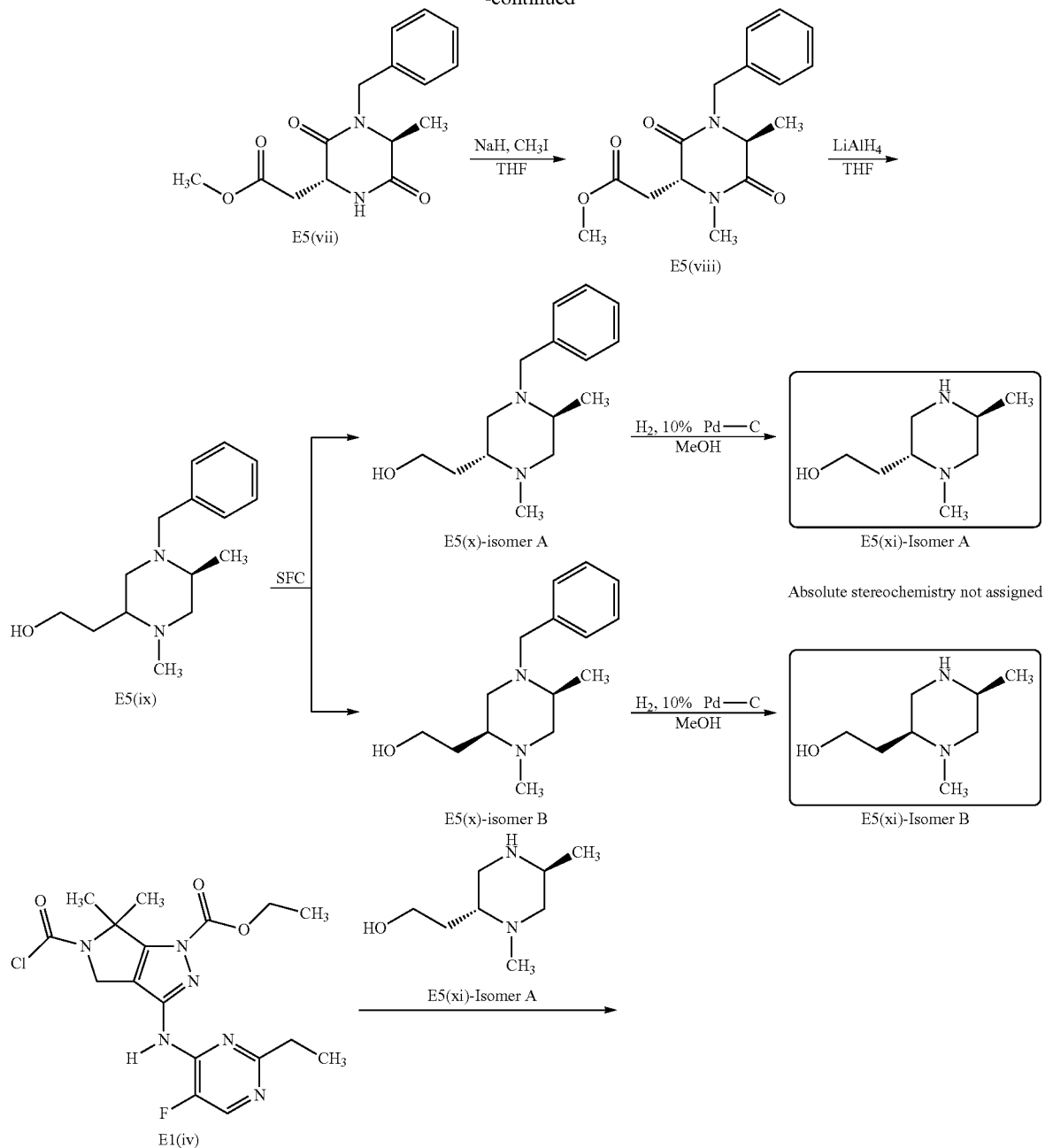
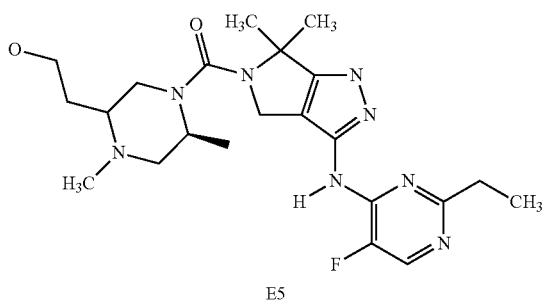

Side-Chain E5(ii) ((S)-methyl 2-(benzylamino)propanoate):

To a mixture of compound E5(i) (27.7 g, 0.2 mol) in CH$_3$CN (350 mL) at 0° was added K$_2$CO$_3$ in portion, after which BnBr (34.2 g, 0.2 mol) was added dropwise over a period of 1 hour. After addition, the mixture was stirred at room temperature for 2 hours. TLC (petrol ether/ethyl acetate=4/1) suggested that the reaction was complete. The reaction was quenched by water (500 mL), and extracted with ethyl acetate (400 mL×3). The combined organic layers were dried over Na$_2$SO$_4$. Filtration and concentration gave the crude, which was purified by column chromatography (eluted with petrol ether/ethyl acetate=50/1 to 4/1) to give compound E5(ii) (15 g, 39%) as a colourless liquid. $^1$H NMR CDCl3 1.2 (d, 3H), 1.9 (bs, 1H), 3.3 (q, 1H), 3.6 (d, 1H), 3.8 (d, 1H), 3.7 (s, 3H), 7.1-7.3 (m 5H)

Intermediate E5(iv) ((R)-2-(tert-butoxycarbonyl)-4-methoxy-4-oxobutanoic Acid)

To a stirred solution of compound E5(iii) (73.5 g, 0.5 mol) in THF (500 mL) and water (500 mL) was added Na$_2$CO$_3$ (106 g, 1 mol), followed by Boc$_2$O (120 g, 0.55 mol). Then the mixture was stirred at room temperature overnight. TLC (dichloromethane/methanol=10/1) suggested that the reaction was complete. The reaction mixture was concentrated, and the residue was dissolved in water (200 mL), extracted with ethyl acetate (500 mL×2). The aqueous layer was separated, and acidified with 1 N HCl to pH=5, extracted with ethyl acetate (500 mL×20). The combined organic layers were dried over Na$_2$SO$_4$. Filtration and concentration gave the compound E5(iv) (75 g, 61%) as an oil.
$^1$H NMR CDCl3 1.4 (s, 9H), 2.8 (dd, 1H), 3.0 (dd, 1H), 3.6 (s, 3H), 4.6 (m, 1H), 5.5 (d, 1H), 9.3 (br, 1H)

Intermediate E5(v) ((R)-methyl 4-(benzyl((R)-1-methoxy-1-oxopropan-2-yl)amino)-3-(tert-butoxycarbonyl)-4-oxobutanoate)

To a stirred solution of compound E5(iv)(117.5 g, 0.475 mol) in DMF (1.5 L) was added NMM (80.1 g, 0.792 mol), HATU (150.6 g, 0.396 mol) in turn. The mixture was stirred at 0° for 30 minutes, then compound 9 (76.5 g, 0.396 mol) was added dropwise. The solution was stirred at room temperature overnight. TLC (petrol ether/ethyl acetate=1/1) suggested that the reaction was complete. The reaction solution was poured into water (1 L), and extracted with ethyl acetate (1 L×3). The combined organic layers were washed with 1 N HCl (200 mL×2), aqueous NaHCO$_3$ (200 mL×2), brine (400 mL), dried over Na$_2$SO$_4$, and concentrated to give compound E5(v)(152 g, 91%) as an oil, which was used the next step without further purification.

Intermediate E5(vi) ((R)-2-((R)-2-amino-N-benzyl-4-methoxy-4-oxobutanamido)propanoic Acid):]

To a stirred solution of compound E5(v) (152 g, 0.362 mol) in dioxane (200 mL) was added HCl (g) in dioxane (1 L). The solution was stirred at room temperature overnight. The solution was concentrated to give compound E5(vi) (100 g, 94%) as an oil, which was used the next step without further purification.

Intermediate E5(vii) (methyl 2-((2R,5S)-4-benzyl-5-methyl-3,6-dioxopiperazin-2-yl)acetate)

Compound E5(vi) (110 g, 0.307 mol) was dissolved in dichloromethane/water (1 L/500 mL). With stirring, aq. NaHCO$_3$ was added dropwise till pH=9, then the solution was stirred at room temperature for one hour. The dichloromethane layer was separated, and the aqueous layer was extracted with dichloromethane (300 mL×2). The combined organic layers were dried over Na$_2$SO$_4$. Filtration and evaporation gave compound E5(vii) (95 g, 99%) as an oil. $^1$H NMR CDCl3 1.3-1.4 (d, 3H), 2.7-2.8 (m, 1H), 3.0-3.1 (m, 1H), 3.6 (s, 3H), 3.8 (m, 1H), 4.0 (d, 1H), 4.4 (m, 1H), 5.2 (d, 1H), 7.1-7.3 (m, 5H), 7.7 (br, 1H)

Intermediate E5(viii) (Methyl 2-((2R,5S)-4-benzyl-1,5-dimethyl-3,6-dioxopiperazin-2-yl)acetate)

To a solution of compound E5(vii) (1.45 g, 5 mmol) in THF (30 mL) was added NaH (0.24 g, 5 mmol) in portion at 0° C., The mixture was stirred for 20 minutes, then CH$_3$I (0.85 g, 6 mmol) in THF (10 ml) was added dropwise. Then the mixture was stirred at room temperature for 5 hours. TLC (petrol ether/ethyl acetate=1/1) suggested that the reaction was complete. The reaction was quenched by water (20 mL), and extracted with ethyl acetate (30 mL×2). The combined organic layers were dried over Na$_2$SO$_4$. Filtration and concentration gave the crude, which was purified by column chromatography (eluted with petrol ether/ethyl acetate=5/1) to give compound E5(viii) (0.7 g, 46%) as an oil. $^1$H NMR CDCl3 1.4 (m, 3H), 2.9 (s, 3H), 3.0-3.2 (m, 1H), 3.5-3.7 (s, 3H), 3.8-4.1 (m, 2H), 4.2-4.4 (m, 1H), 5.1-5.3 (m, 1H), 7.1-7.3 (m 5H)

Intermediate E5(ix) (2-((5S)-4-benzyl-1,5-dimethylpiperazin-2-yl)ethanol)

To a solution of compound E5(ix) (12 g, 0.04 mmol) in THF (250 mL) was added LiAlH$_4$ (7.6 g, 0.2 mol) in portion at 0° C. After addition, the reaction mixture was heated to reflux for 36 hours. TLC (dichloromethane/methanol=10/1) suggested that the reaction was complete. The reaction was quenched by water (5 mL), and the mixture was filtered, the cake was washed with ethyl acetate several times. The filtrate was washed with Na$_2$SO$_4$. Filtration and concentration gave the crude, which was purified by column chromatography (eluted with dichloromethane/methanol=100/1 to 10/1) to give racemic compound E5(ix) (8.3 g, 84%) as an oil.

Intermediate E5(x)—Isomers A and B: 2-((2R,5S)-4-benzyl-1,5-dimethylpiperazin-2-yl)ethanol and 2-((2S,5S)-4-benzyl-1,5-dimethylpiperazin-2-yl)ethanol The racemic compound E5(ix) was separated by SFC using AS-H (0.46×2.5 cm×5 µm) column with 5% MeOH (0.025% DEA) and 95% CO$_2$ as mobile phase to give compounds E5(x)—Isomer A and B (5.2 g and 1.9 g respectively). E5(x)—Isomer A: $^1$H NMR CDCl3 1.0 (d, 3H), 1.4 (m, 1H), 1.7 (m, 1H), 2.0 (m, 2H), 2.1 (m, 1H), 2.2 (s, 3H), 2.4 (m, 1H), 2.6 (dd, 1H), 2.7 (dd, 1H), 3.0 (d, 1H), 3.4 (m, 1H), 3.6 (m, 1H), 4.0 (d, 1H), 4.2 (br, 1H), 7.1-7.3 (m, 5H). E5(x)—Isomer B: $^1$H NMR CDCl3 1.0 (d, 3H), 1.6-1.8 (m, 2H), 2.2-2.7 (m, 9H), 3.2 (d, 1H), 3.4 (m, 1H), 3.6 (m, 1H), 3.8 (d, 1H), 4.8 (br, 1H), 7.1-7.3 (m, 5H).

Intermediates E5(xi)—Isomers A and B: 2-((2R,5S)-1,5-dimethylpiperazin-2-yl)ethanol and 2-((2S,5S)-1,5-dimethylpiperazin-2-yl)ethanol The mixture of compound E5(x)—Isomer A (5.2 g, 0.021 mol) and Pd/C (0.5 g) in MeOH (40 mL) or the mixture of compound E5(x)—Isomer B (1.9 g, 7.7 mmol) and Pd/C (0.2 g) in MeOH (40 mL) under 50 psi of H2 was stirred at room temperature overnight. TLC (dichloromethane/methanol=10/1) suggested that the reaction was complete. The reaction mixture was filtered and the filtrate was concentrated to give E5(xi)—Isomer A (3.1 g, 94%) as an offwhite solid or E5(xi)—Isomer B (1.2 g, 93%) as an offwhite solid. E5(xi)—Isomer A: $^1$H NMR CDCl3 1.0 (d, 3H) 1.8 (m, 1H), 2.0 (m, 1H), 2.4-3.1 (m, 9H), 3.8 (m, 2H). E5(xi)—Isomer B: $^1$H NMR CDCl3 1.0 (d, 3H), 1.5 (m, 1H), 1.8 (t, 1H), 2.0-2.3 (m, 2H), 2.4 (s, 3H), 2.7-3.0 (m, 4H), 3.7 (m, 1H), 3.9 (m, 1H).

Example E5: 2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol The title compound was prepared using a method analogous to Example E1 above except that E5(xi)—Isomer A was substituted in place of ((2R,5S)-1,2,5-trimethylpiperazine. See Table 1 below for NMR data.

Example F1: 5-[(4-fluoro-1-methylpiperidin-4-yl)carbonyl]-N-(5-fluoro-2-methylpyrimidin-4-yl)-6,6-dimethyl-1,4,5,6-tetrahydropyrrolo[3,4-c]pyrazol-3-amine

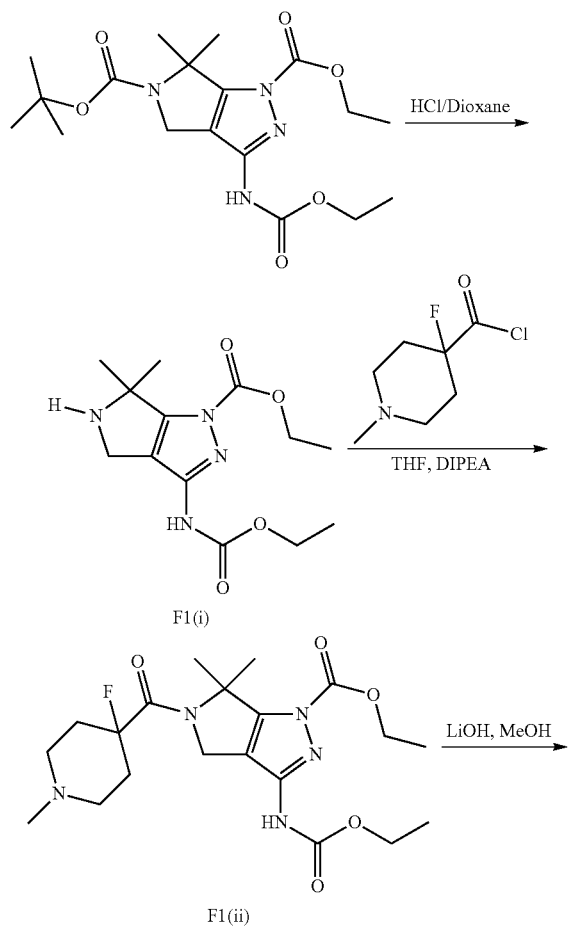

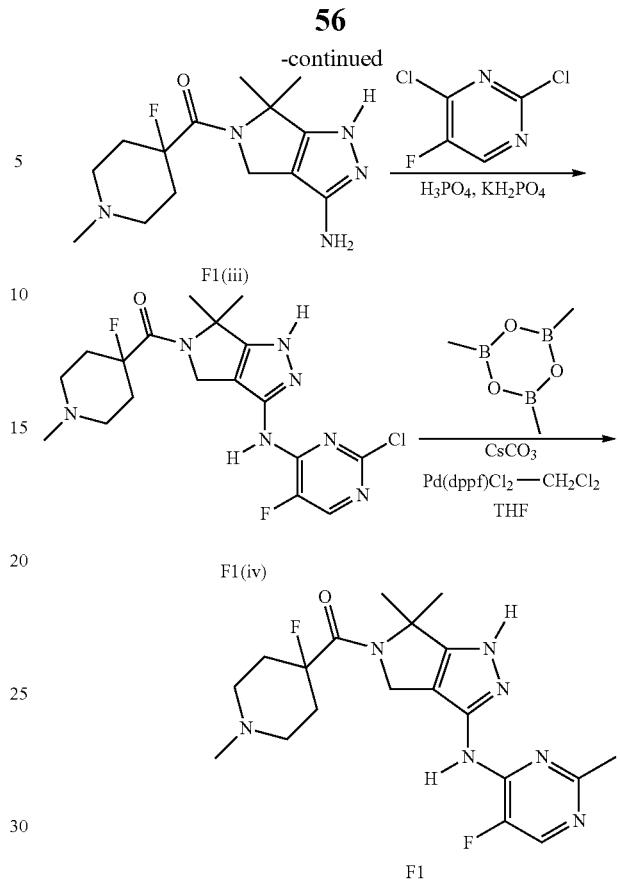

Intermediate F1(i): Ethyl 3-[(ethoxycarbonyl)amino]-6,6-dimethyl-5,6-dihydropyrrolo[3,4-c]pyrazole-1(4H)-carboxylate To a solution of 3-Ethoxycarbonylamino-6,6-dimethyl-4,6-dihydro-pyrrolo[3,4-c]pyrazole-1,5-dicarboxylic acid 5-tert-butyl ester 1-ethyl ester (5.69 g, 14.4 mmol) in CH$_2$Cl$_2$ (10 mL) was added 4M HCl in 1,4-dioxane (20 mL). The solution was stirred for 1 h, at which time the volatiles were removed in vacuo to yield the desired product-1(i) as a white solid (4.8 g, 91%). Mass Spectrum: Calcd for C$_{13}$H$_{21}$N$_4$O$_4$ (M+H): 297. Found: 297.

Intermediate F1(ii): Ethyl 3-[(ethoxycarbonyl)amino]-5-[(4-fluoro-1-methylpiperidin-4-yl)carbonyl]-6,6-dimethyl-5,6-dihydropyrrolo[3,4-c]pyrazole-1(4H)-carboxylate To a pressure vessel was added F1(i) 4.80 g, 16.2 mmol), 4-fluoro-1-methylpiperidine-4-carbonyl chloride (2.45 g, 13.6 mmol), diisopropylethylamine (9.06 mL, 52.0 mmol), and THF (300 mL). The suspension was heated at 80° C. for 15 h. The volatiles were removed in vacuo to yield the desired product F1(ii) as a brown foam (5.6 g, 98%). Mass Spectrum: Calcd for C$_{20}$H$_{31}$N$_5$O$_5$F (M+H): 440. Found: 440.

Intermediate F1 (iii): 5-[(4-fluoro-1-methylpiperidin-4-yl)carbonyl]-6,6-dimethyl-1,4,5,6-tetrahydropyrrolo[3,4-c]pyrazol-3-amine To a microwave vial was added F1(ii) (9.80 g, 22.0 mmol) in a solution of MeOH (35 mL) and LiGH (2.14 g, 89.2 mmol). The reaction was heated at 110° C. in the microwave for 2 h. The reaction mixture was concentrated in vacuo to give the desired product F1 (iii as a tan foam (4.4 g, 67%). Mass Spectrum: Calcd for $C_{14}H_{23}N_5OF$ (M+H): 296. Found: 296.

Intermediate F1(iv): N-(2-chloro-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine To a solution of F1(iii) (1.40 g, 4.74 mmol) and 2,4-dichloro-5-fluoro pyrimidine (0.791 g, 4.74 mmol) in DMSO (10 mL) was added potassium dihydrogenphosphate (0.645 g, 4.74 mmol) followed by $H_3PO_4$ (0.0929 g, 0.948 mmol). The reaction heat to 95° C. for 15 h. The crude reaction mixture was cooled to 22° C. then poured into ice cold $NaHCO_3$(sat., aq.) (100 mL). The aqueous layer was extracted with EtOAc (2×50 mL) and the combined organic layers washed with brine (2×50 mL), dried over magnesium sulfate, and concentrated to give the desired product F1(iv) as a brown solid (0.633 g, 31%). Mass Spectrum: Calcd for $C_{18}H_{23}N_7OF_2Cl$ (M+H): 426. Found: 426.

Example F1: 5-[(4-fluoro-1-methylpiperidin-4-yl) carbonyl]-N-(5-fluoro-2-methylpyrimidin-4-yl)-6,6-dimethyl-1,4,5,6-tetrahydropyrrolo[3,4-c]pyrazol-3-amine To a pressure vessel was added F1(iv) (0.225 g, 0.528 mmol), trimethylboroxine (1.47 mL, 10.6 mmol), cesium carbonate (3.44 g, 10.6 mmol), dichloro[1,1'-bis(diphenylphosphino)ferrocene]palladium(II) dichloromethane adduct (0.0647 g, 0.0792 mmol), $H_2O$ (0.8 mL), and THF (8.0 mL). The suspension was purged with argon for 2 min, then heat at 100° C. for 15 h. The cooled solution was filtered to remove undissolved solids, concentrated, and redissolved in MeOH. Preparative HPLC using 20-60% $ACN/H_2O$ (0.1% AcOH) provided the desired product F1 as a white solid (0.020 g, 9.3%). See Table 1 below for NMR data.

Example G1: N-(2-ethyl-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine

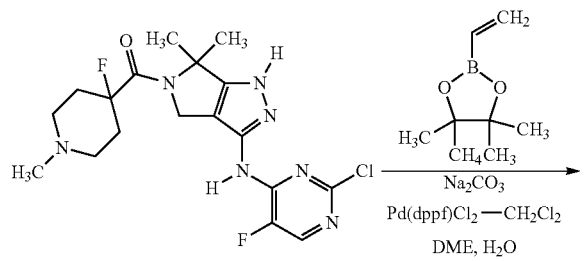

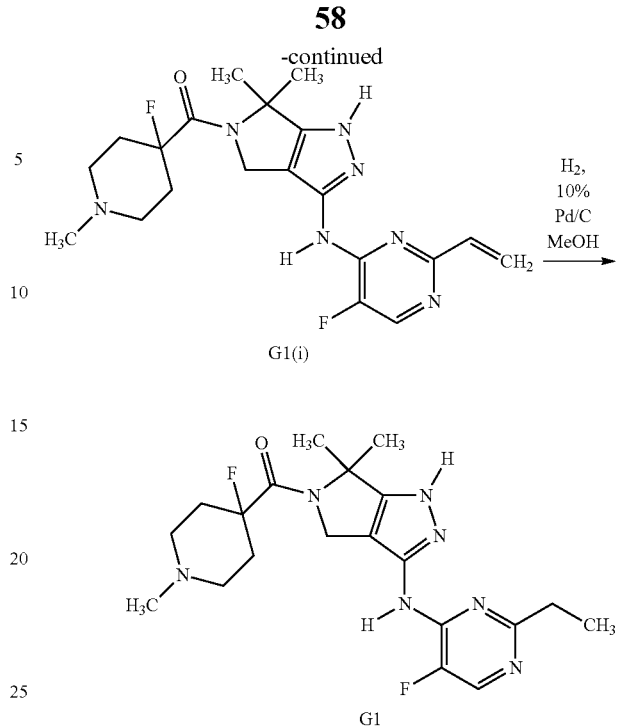

Intermediate G1(i): 5-[(4-fluoro-1-methylpiperidin-4-yl)carbonyl]-N-(5-fluoro-2-vinylpyrimidin-4-yl)-6,6-dimethyl-1,4,5,6-tetrahydropyrrolo[3,4-c]pyrazol-3-amine To a pressure vessel was added starting material [3-(2-Chloro-5-fluoro-pyrimidin-4-ylamino)-6,6-dimethyl-4,6-dihydro-1H-pyrrolo[3,4-c]pyrazol-5-yl]-(4-fluoro-1-methyl-piperidin-4-yl)-methanone (0.375 g, 0.881 mmol), 4,4,5,5-tetramethyl-2-vinyl-1,3,2 dioxaborolane (0.407 g, 2.64 mmol), $Na_2CO3$ (0.280 g, 2.64 mmol) and dichloro[1,1'-bis(diphenylphosphino)ferrocene]palladium(II) dichloromethane adduct (0.144 g, 0.176 mmol) followed by DME (10 mL) and water (2 mL). The reaction mixture was purged with argon for 2 min, then heat to 100° C. for 15 h. The volatiles were concentrated in vacuo and the residue redissolved in EtOAc (15 mL). The organic layer was washed with water (10 mL), dried over $MgSO_4$, filtered, and concentrated to give the desired product G1(i) as a brown foam (0.35 g, 95%). Mass Spectrum: Calcd for $C_{20}H_{26}N_7OF_2$ (M+H): 418. Found: 418.

Example G1: N-(2-ethyl-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine To a solution of starting material (0.413 g, 0.989 mmol) in MeOH (10 mL) was added 10% palladium on carbon (0.0400 g, 0.380 mmol). The suspension was evacuated/backfilled with hydrogen for 3 times and allowed to stir for 15 h under hydrogen. The suspension was filtered through Celite, the filter cake washed with $CH_2Cl_2$, and the filtrate concentrated. Preparative HPLC provided the desired product G1 as a white solid (0.018 g, 4.4%). See Table 1 below for NMR data.

Example H1: N-(5-fluoro-2-methylpyrimidin-4-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine

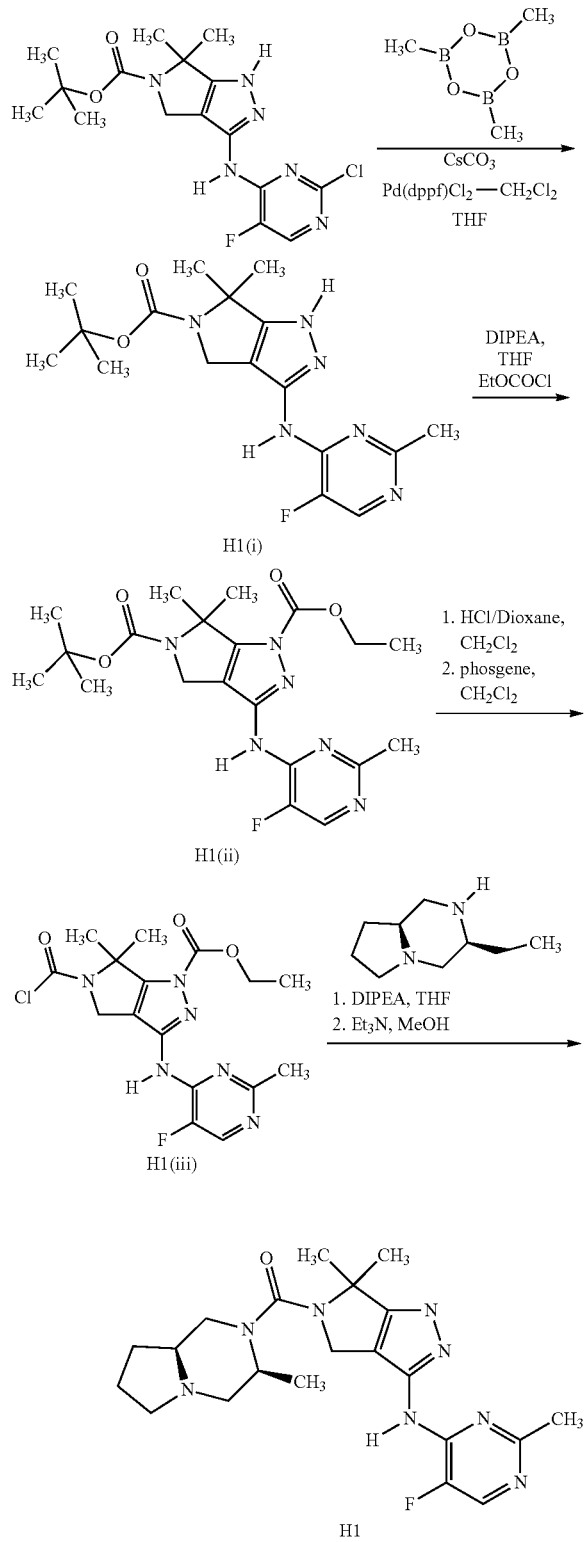

Intermediate H1(i): tert-butyl 3-[(5-fluoro-2-methylpyrimidin-4-yl)amino]-6,6-dimethyl-4,6-dihydropyrrolo[3,4-c]pyrazole-5(1H)-carboxylate To a pressure vessel was added 3-(2-Chloro-5-fluoro-pyrimidin-4-ylamino)-6,6-dimethyl-4,6-dihydro-1H-pyrrolo[3,4-c]pyrazole-5-carboxylic acid tert-butyl ester (1.50 g, 3.90 mmol), trimethylboroxine (10.9 mL, 78.4 mmol), cesium carbonate (25.5 g, 78.4 mmol), dichloro[1,1'-bis(diphenylphosphino)ferrocene]palladium(II) dichloromethane adduct (0.480 g, 0.588 mmol), H$_2$O (6 mL), and THF (60 mL). The suspension was purged with argon for 2 min, then heat at 100° C. for 15 h. The cooled solution was filtered to remove undissolved solids. Purification by silica gel column chromatography using 0-10% ammoniated methanol in CH$_2$Cl$_2$ provided the desired product H1(i) as a brown solid (0.80 g, 56%). $^1$H NMR (300 MHz, DMSO-d$_6$) δ ppm 1.41 (s, 9H) 1.57 (s, 6H) 2.38 (s, 3H) 4.43-4.58 (m, 2H) 8.12 (s, 1H) 10.02 (s, 1H) 12.34 (s, 1H). Mass Spectrum: Calcd for C$_{17}$H$_{24}$N$_6$O$_2$F (M+H): 363. Found: 363.

Intermediate H1(ii): 5-tert-butyl 1-ethyl 3-[(5-fluoro-2-methylpyrimidin-4-yl)amino]-6,6-dimethyl-4,6-dihydropyrrolo[3,4-c]pyrazole-1,5-dicarboxylate To a 0° C. solution of H1(i) (0.800 g, 2.21 mmol) in THF (10 mL) was added NaH (60% dispersion in mineral oil, 0.124 g, 3.09 mmol). The solution was stirred at 0° C. for 10 min, at which time ethylchloroformate (0.421 mL, 4.41 mmol) was added. The solution was warmed to 22° C. and stirred for 15 h. The reaction was quenched with NH$_4$Cl (sat., aq.) (10 mL) and the aqueous layer extracted with EtOAc (3×30 mL). The combined organic layers were washed with brine (1×20 mL), dried over MgSO$_4$ and concentrated to give the desired product H1(ii) as a brown solid (0.92 g, 96%). Mass Spectrum: Calcd for C$_{20}$H$_{28}$N$_6$O$_4$F (M+H): 435. Found: 435.

Intermediate H1(iii): Ethyl 5-(chlorocarbonyl)-3-[(5-fluoro-2-methylpyrimidin-4-yl)amino]-6,6-dimethyl-5,6-dihydropyrrolo[3,4-c]pyrazole-1(4H)-carboxylate To a solution of H1(ii) (0.919 g, 2.12 mmol) in CH$_2$Cl$_2$ (5 mL) was added 4M HCl in dioxane (10 mL). The solution was stirred for 1 h, concentrated in vacuo, and redissolved in CH$_2$Cl$_2$ (40 mL) and diisopropylethylamine (1.67 mL, 9.58 mmol). The solution was cooled to −78° C. and triphosgene (0.569 g, 1.92 mmol) in CH$_2$Cl$_2$ (10 mL) was added dropwise over 30 min. The reaction was quenched with H$_2$O (10 mL), warmed to 22° C., and made pH 8-9 with NaHCO$_3$. The aqueous layer was extracted with CH$_2$Cl$_2$ (2×30 mL) and the combined organic layers washed with brine (1×30 mL), dried over MgSO$_4$, and concentrated to give the desired product H1(iii) as a brown solid (0.49 g, 46%). Mass Spectrum: Calcd for C$_{16}$H$_{19}$ClN$_6$O$_4$F (M+H): 397. Found: 397.

Example H1: N-(5-fluoro-2-methylpyrimidin-4-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine To a pressure vessel was added H1(iii) (0.244 g, 0.615 mmol), (3S,8aS)-3-methyloctahydropyrrolo[1,2-a]pyrazine (0.0862 g, 0.615 mmol), diisopropylethylamine (0.428 mL, 2.46 mmol), and THF (5 mL). The suspension was stirred at 90° C. for 2 h. Volatiles were removed in vacuo and the residue redissolved in MeOH (10 mL). Triethylamine (5 mL) was added and the solution stirred for 15 h. Preparative HPLC using 20-60% ACN/H₂O (0.1% AcOH) provided the desired product H1 as a white solid (0.12 g, 38%).

Examples H2-H7

Examples H2 through H7 were prepared using methods analogous to Example H1 above. See Table 1 below for names and NMR data.

Example H8: 4-[((2R,5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol

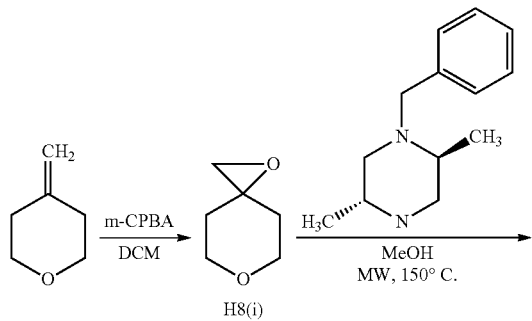

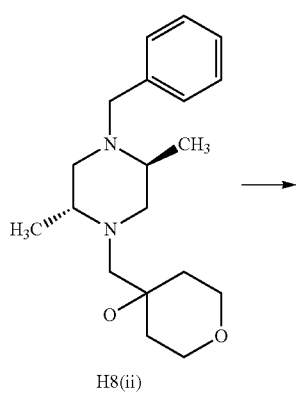

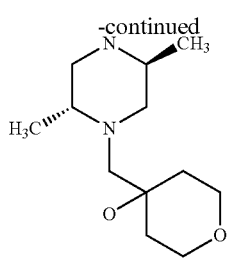

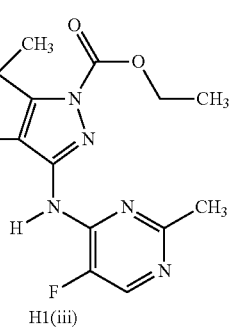

Intermediate H8(i): 1,6-dioxaspiro[2.5]octane

A solution of 4-methylenetetrahydro-2H-pyran (1.00 g, 10.2 mmol) in CH₂Cl₂ (30 mL) was placed in an ice bath then meta-chloroperoxybenzoic acid (2.46 g, 14.3 mmol) was added in three portions. The reaction was slowly warmed to RT and stirred for 3 h then quenched with 10% NaOH(aq) (10 mL) and extracted with CH₂Cl₂ (2×15 mL). The combined extracts were dried (MgSO₄), filtered and concentrated to provide intermediate H8(i) as a clear oil (607 mg, 52%).

Intermediate H8(ii) (4-(((2R,5S)-4-benzyl-2,5-dimethylpiperazin-1-yl)methyl)-tetrahydro-2H-pyran-4-ol)

To a microwave vial was added H8 (i) (259 mg, 2.3 mmol) and (2S,5R)-1-benzyl-2,5-dimethylpiperazine (464 mg, 2.3 mmol) and 5 mL of MeOH. The vial was heated to 150° C. for 2 h in the microwave. The crude reaction was concentrated to provide intermediate H8(ii) (723 mg, 100%)

Intermediate H8(iii) 4-{[(2R,5S)-2,5-dimethylpiperazin-1-yl]methyl}tetrahydro-2H-pyran-4-ol To a solution of H8(ii) (723 mg, 2.3 mmol) in MeOH (15 mL) was added Pd/C (72 mg, 0.07 mmol). The reaction was subject evacuation-backfill (3×) with H₂ gas then run under an H2 atmosphere overnight. The completed reaction mixture was filtered through a bed of Celite, rinsed with CH₂Cl₂ and MeOH then concentrated to give the title compound (500 mg, 97%) as a yellow-orange semi solid H8(iii).

Example H8: 4-[((2R,5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol The title compound was prepared using methods analogous to Example H1 above. See Table 1 below for NMR data.

Examples H9-H10

Examples H9 and H10 were prepared using methods analogous to Example H1 above, except E5(xi)-Isomers A and B, respectively, were substituted in place of (3S,8aS)-3-methyloctahydropyrrolo[1,2-a]pyrazine. See Table 1 below for names and NMR data.

Example 11: N-(5-fluoro-2-propylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine

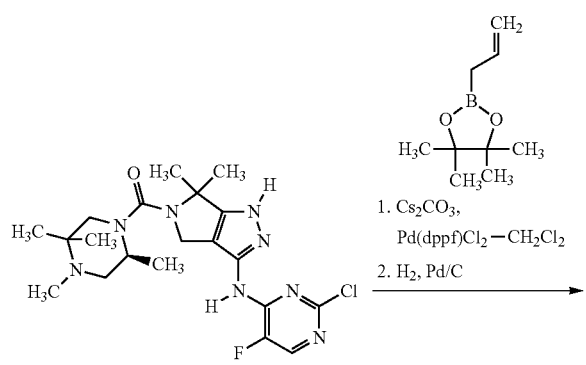

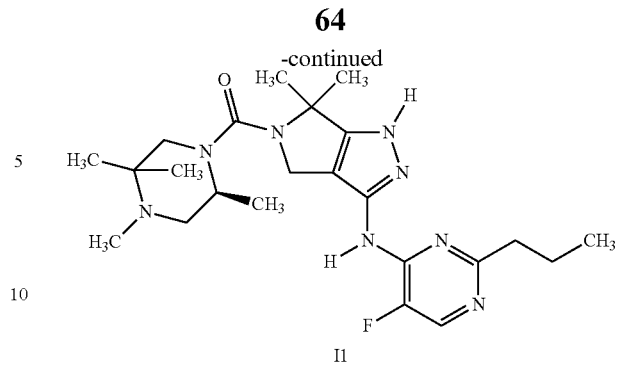

To a pressure vessel was added [3-(2-Chloro-5-fluoro-pyrimidin-4-ylamino)-6,6-dimethyl-4,6-dihydro-1H-pyrrolo[3,4-c]pyrazol-5-yl]-((S)-2,4,5,5-tetramethyl-piperazin-1-yl)-methanone (0.150 g, 0.330 mmol), 2-allyl-4,4,5,5-tetramethyl-1,3,2-dioxaborolane (1.12 g, 6.66 mmol), cesium carbonate (0.543 g, 1.66 mmol), dichloro[1,1'-bis(diphenylphosphino)ferrocene]palladium(II) dichloromethane adduct (0.0408 g, 0.0498 mmol), H₂O (0.3 mL), and THF (3 mL). The suspension was purged with argon for 2 min, then stirred at 100° C. for 15 h. The cooled solution was filtered to remove undissolved solids and the volatiles removed in vacuo. The residue was redissolved in MeOH (5 mL) and 10% palladium on carbon (0.0400 g, 0.380 mmol) was added. The suspension was evacuated and backfilled with hydrogen for 3 times and allowed to stir for 15 h under hydrogen. The suspension was filtered through Celite, the filter cake washed with CH₂Cl₂, and the filtrate concentrated. Preparative HPLC provided the desired product 11 as a white solid (0.025 g, 14%).

Example I2

Example I2 was prepared using methods analogous to Example I1 above. See Table 1 below for name and NMR data.

Examples J1-J8

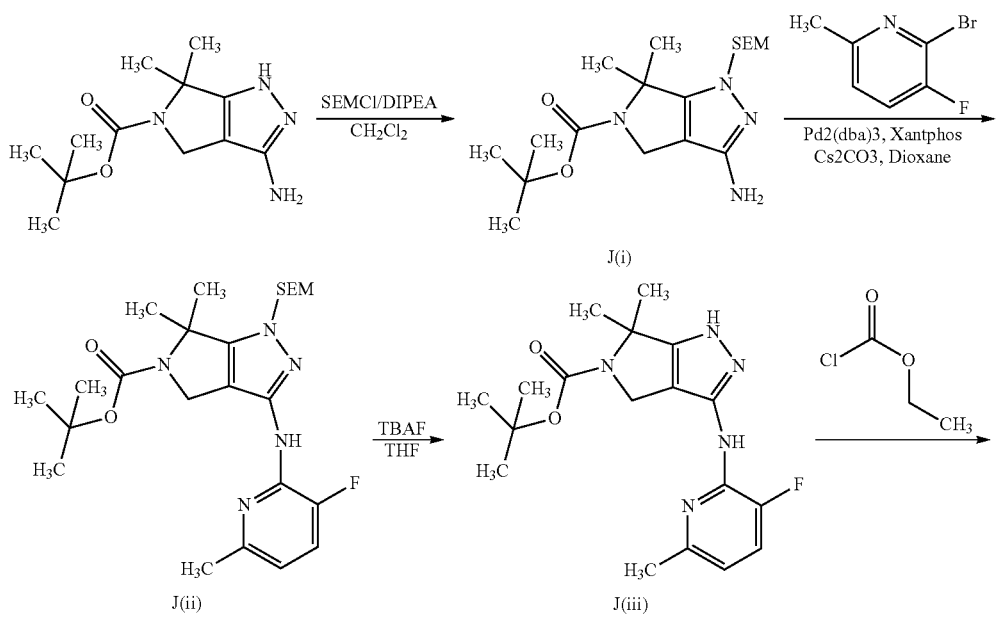

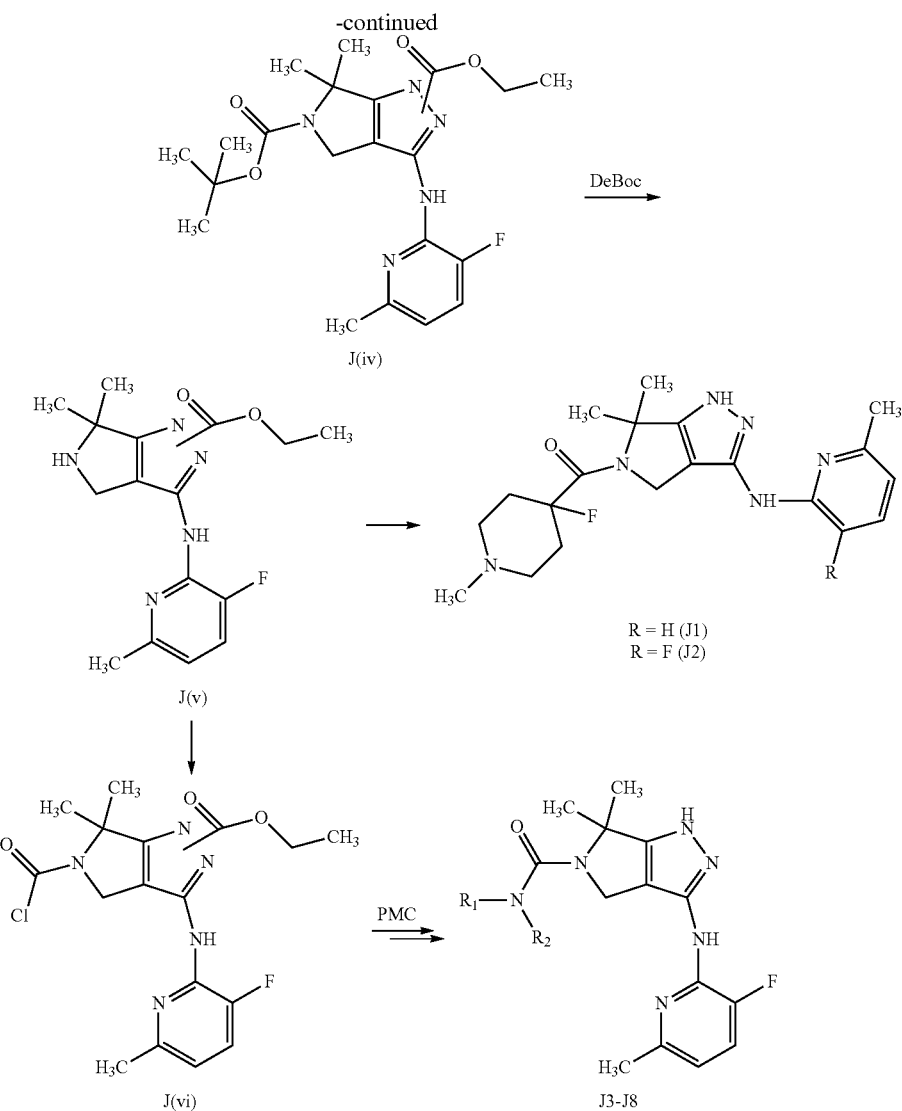

Intermediate J(i): Tert-Butyl 3-amino-6,6-dimethyl-1-{[2-(trimethylsilyl)ethoxy]methyl}-4,6-dihydropyrrolo[3,4-c]pyrazole-5(1H)-carboxylate To a suspension of tert-butyl 3-amino-6,6-dimethyl-4,6-dihydropyrrolo[3,4-c]pyrazole-5(1H)-carboxylate (8.5 g, 33.9 mmol) and diisopropyl ethylamine (18 mL, 3.0 equiv) in dichloromethene (200 mL) was added 2-(trimethylsilyl) ethoxymethyl chloride (6.0 mL, 1.0 equiv) dropwise at 0° C. under nitrogen. The mixture was been stirred at 0° C. under nitrogen for two hours then warmed to room temperature and stirred over night. The reaction mixture was concentrated and purified by column chromatography to give the title compound J(i) as a white solid (2.27 g, 18%). 1H NMR (400 MHz, METHANOL-$d_4$): δ ppm 0.81-0.97 (m, 2H) 1.45-1.59 (m, 9H) 1.72 (d, J=5.29 Hz, 13H) 3.53-3.67 (m, 2H) 4.26 (d, J=7.55 Hz, 2H) 5.17 (s, 2H). 2D-NOESY NMR showed proton at 5.17 ppm is correlated with proton at 1.72 ppm.

Intermediate J(ii): Tert-Butyl 3-[(3-fluoro-6-methylpyridin-2-yl)amino]-6,6-dimethyl-1-{[2-(trimethylsilyl)ethoxy]methyl}-4,6-dihydropyrrolo[3,4-c]pyrazole-5(1H)-carboxylate To a flask equipped with a condenser was added J(i) (4.7 g, 12.3 mmol), Cesium Carbonate (8.0 g, 25 mmol), 2-bromo-3-fluro-picoline (2.6 g, 14 mmol), Pd2(dba)$_3$ (600 mg, 0.6 mmol, 10 mol % Pd), Xantphos (700 mg, 1.2 mmol, 10 mol %) and 1,4 dioxane (150 mL). The reaction mixture was stirred for 15 min under nitrogen atmosphere. While the mixture was being stirred, degassed water (50) mL was added. The mixture was heated at 100° C. for 16 hours under nitrogen atmosphere and then evaporated 4/5 volumn solvent. Water was introduced and the mixture extracted with ethyl acetate (3×100 mL). The combined organics were washed with water and saturated aqueous sodium chloride, dried (anhydrous sodium sulfate), filtered, concentrated and purified by column chromatography to give the title compound A(i) as a white solid (2.9 g, 48%).

Intermediate J(iii): Tert-Butyl 3-[(3-fluoro-6-methylpyridin-2-yl)amino]-6,6-dimethyl-4,6 dihydropyrrolo[3,4-c]pyrazole-5(1H)-carboxylate To a solution of J(ii) (2.9 g, 5.9 mmol) in THF (100 mL) was added TBAF (7.7 g, 29.5 mmol, 5 equiv). The reaction mixture was heated at 70° C. for 16 hours and then evaporated 4/5 volume solvent. Water was introduced and the mixture extracted with ethyl acetate twice. The combined organics were washed with water and saturated aqueous sodium chloride, dried (anhydrous sodium sulfate), filtered, concentrated and purified by column chromatography to give the title compound J(iii) as a white solid (1.6 g, 76%). LCMS (API-ES, M+H$^+$): 362.

Intermediate J(iv): Ethyl Acetate-Tert-Butyl 3-[(3-fluoro-6-methylpyridin-2-yl)amino]-6,6-dimethyl-4,6-dihydropyrrolo[3,4-c]pyrazole-5(1H)-carboxylate A solution of carboethoxy chloride (0.58 g, 5.35 mmol, 1.2 equiv.) in THF (5 mL) was added slowly to a suspension mixture of J(iii) (1.6 g, 4.46 mmol) and DIPEA (3.9 mL, 5 equiv) in THF (80 mL) at 0° C. under nitrogen. The reaction was kept at 0° for two hours and then warmed to room temperature and stirred over night. The reaction mixture was concentrated and purified by column chromatography to give the title compound J(iv) as a white solid (627 mg, 35%).

Intermediate J(v): Ethyl Acetate-N-(3-fluoro-6-methylpyridin-2-yl)-6,6-dimethyl-1,4,5,6-tetrahydropyrrolo[3,4-c]pyrazol-3-amine To a clear solution of J(iv) (627 mg, 1.45 mmol) in Dioxane (10 mL), 4M HCl in dioxane (10.8 mL, 30 equiv) was added. The reaction mixture was stirred at room temperature for 6 hours. Evaporated solvent and volatile, dried in vacuum to give the title compound J(v) as HCl salt.

Intermediate J(vi) (Applicable to Examples J3-J6): Ethyl Acetate-3-[(3-fluoro-6-methylpyridin-2-yl)amino]-6,6-dimethyl-4,6-dihydropyrrolo[3,4-c]pyrazole-5(1H)-carbonyl Chloride To a clear solution of triphosgene (472 mg, 1.59 mmol) in DCM, DIPEA (1.26 mL, 7.23 mmol) was added dropwise (white smoke) under N2 at 0° C. The suspension of the crude product J(v) (489 mg, 1.27 mmol) in DCM (20 mL) was added dropwise. The reaction mixture was warmed to room temperature slowly and stirred at room temperature under nitrogen over night. Evaporated solvent and volatile, dried in vacuum to give the title compound J(vi) as HCl salt. See Table 1 below for NMR data.

Example J1: 5-[(4-fluoro-1-methylpiperidin-4-yl)carbonyl]-N-(3-fluoro-6-methylpyridin-2-yl)-6,6-dimethyl-1,4,5,6-tetrahydropyrrolo[3,4-c]pyrazol-3-amine

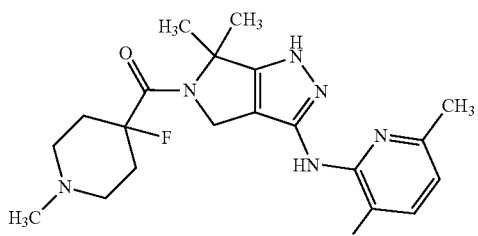

A solution of J(v) (68 mg, 0.17 mmol), 4-fluoro-1-methylpiperidine-4-carbonyl chloride (74.2 mg, 2 equiv), and DIPEA (0.18 mL) in THF (10 mL) was heated to 70° C. for 16 hrs. THF was concentrated. The reaction mixture was dissolved in CH$_3$OH (10 mL) and Et$_3$N (5 mL) then stirred at room temperature for 16 hrs. The residue was purified by HPLC (0.1% HOAc as a buffer) to give the title compound J1 as a solid (80 mg, 20% yield). See Table 1 below for NMR data.

Examples J2-J8

Examples J2 through J8 were prepared using methods analogous to Example J1 above, with Examples J3 through J8 being further derived from Intermediate J(vi) as described in the schematic above. See Table 1 below for names and NMR data.

Example J9: N-[5-fluoro-2-(methoxymethyl)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine

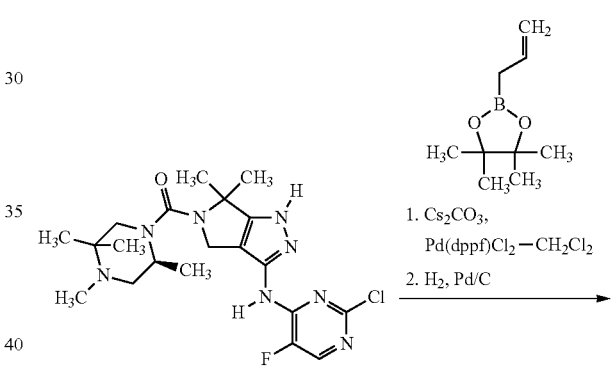

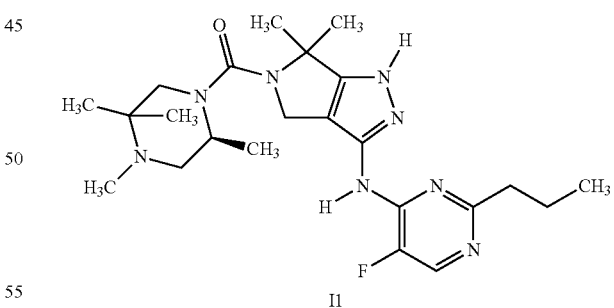

Example J9 was prepared using methods analogous to Examples J1 through J8, except substituting A1 (iv) in place of J(i) as shown above. See Table 1 below for NMR data.

Examples J10-J16

Examples J10 through J16 were prepared using methods analogous to Example J9 above. See Table 1 below for names and NMR data.

Example K1: N-(2-ethoxy-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine

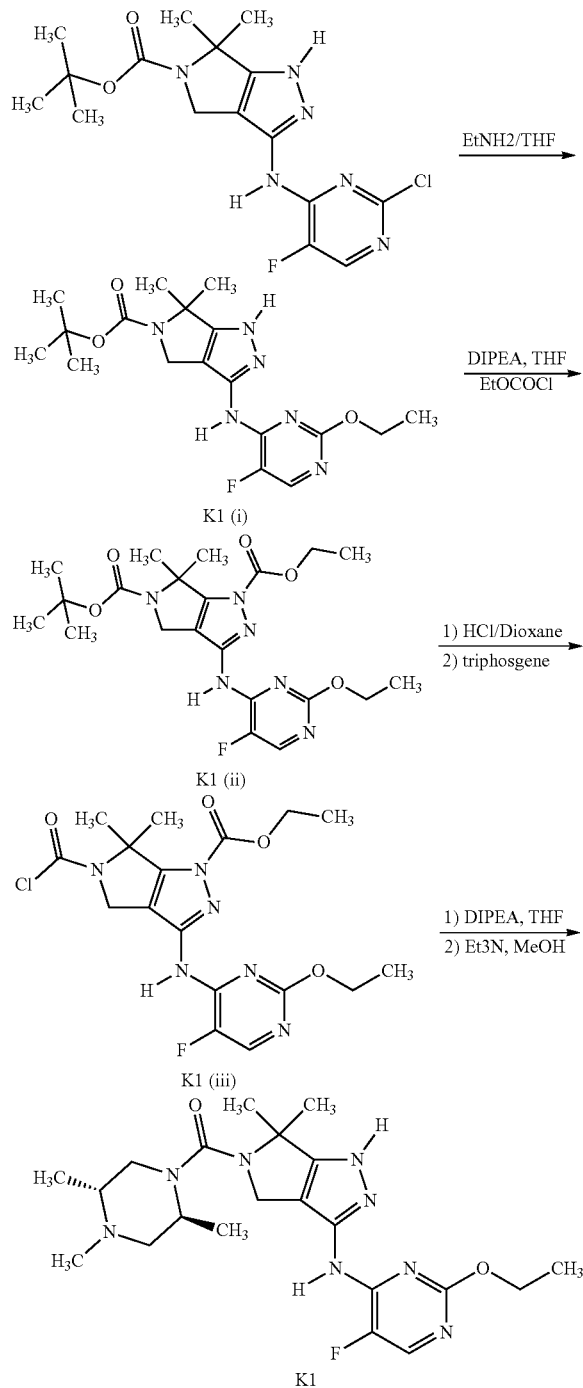

Intermediate K1(i): Tert-Butyl 3-[(2-ethoxy-5-fluoropyrimidin-4-yl)amino]-6,6-dimethyl-4,6-dihydropyrrolo[3,4-c]pyrazole-5(1H)-carboxylate A fresh solution of sodium ethoxide was prepared by dissolving 7 g of sodium metal in 140 ml of anhydrous ethanol. Twelve 20 ml Biotage microwave vials, equipped with magnetic stir bars, were charged with 1.2 g of the chloride (total 14.4 g, 38 mmol). To each vial was added 10 ml of the aforementioned sodium ethoxide solution followed by 5 ml of anhydrous ethanol. The vials were sealed, and processed in a batchwise fashion using a Biotage Initiator microwave. Each reaction was heated to 160° C. for 10 minutes. After being cooled, the reaction vials were opened (the reaction was shown to be complete by LC-MS), and the contents combined. Each vial was rinsed with 5 ml of ethanol, and 10 ml of water (a solid precipitate deposits at the bottom of the vial), and the washings combined with the original contents of the vial. The ethanol was removed in vacuo, and the aqueous extracted with ethyl acetate (3×150 ml). The organic extracts were dried over sodium sulfate, and the solvent removed in vacuo to afford the product as a slightly yellow solid (14.1 g, 96%). This was sufficiently pure to be used directly in the next step.

Note: Thermal heating to reflux for an extended period of time (18 hours) did not effect the transformation. Use of a sealed tube was not attempted. Microwave heating at 140° C. for 10 minutes lead to a 60% conversion by LC-MS.

Intermediate K1(ii): 5-Tert-Butyl 1-Ethyl 3-[(2-ethoxy-5-fluoropyrimidin-4-yl)amino]-6,6-dimethyl-4,6-dihydropyrrolo[3,4-c]pyrazole-1,5-dicarboxylate To a solution of K1(i)(175 mg, 0.44 mmol) in methylene chloride was added triethyl amine (0.07 mL, 1.2 eq) followed by ethyl chloroformate (0.04 mL, 1.0 eq). After stirring at room temperature for 12 hours, the solvent was removed in vacuo and the residue was partitioned between methylene chloride and water. The organic layer was separated then concentrated to a yellow solid K1 (ii which was carried on without further purification.

Intermediate K1(iii): Ethyl 5-(chlorocarbonyl)-3-[(2-ethoxy-5-fluoropyrimidin-4-yl)amino]-6,6-dimethyl-5,6-dihydropyrrolo[3,4-c]pyrazole-1(4H)-carboxylate To a solution of K1(ii) (170 mg, 0.36 mmol) in 6 mL of dry dioxane was added 1 mL of 4M HCl in dioxane. After stirring at room temperature for 48 hours, the solvent was removed in vacuo and the white solid residue was dried for several hours under high vacuum and carried on without further purification. The reaction with triphosgene was carried out using the same procedure as in the preparation of intermediate E1(iv) $^1$H NMR (400 MHz, CHLOROFORM-D) δ ppm 1.38-1.43 (3H, m), 1.49-1.54 (3H, m), 1.78-1.86 (6H, m), 4.32-4.42 (2H, m), 4.61 (2H, qd, J=7.13, 1.26 Hz), 5.17 (2H, d, J=59.42 Hz), 8.08 (1H, t, J=2.39 Hz), 10.27 (1H, d, J=9.57 Hz). LCMS (M+H)*427.1

Example K1: N-(2-ethoxy-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine To a solution of K1 (iii) (70 mg, 0.16 mmol) in tetrahydrofuran (4 mL) was added (2R,5S)-1,2,5-trimethylpiperazine hydrochloride (108 mg, 4 equiv) and diisopropylethyl amine (0.15 mL, 6.8 equiv). The resulting mixture was heated in a sealed tube at 80° C. for 16 hours and then allowed to cool to ambient temperature. To the crude reaction mixture was added one sodium hydroxide pellet dissolved in 2 mL methanol and stirring was continued at room temperature for one hour. The solvent was removed in vacuo and the residue was purified by reverse-phase HPLC using a gradient of 15% to 35% acetonitrile in water (0.1% acetic acid modifier) ramped over 25 minutes. Overnight lyophilization afforded the title compound K1 as a white powder (37 mg, 44%). See Table 1 below for NMR data.

Examples K2-K19

Examples K2 through K19 were prepared using methods analogous to Example K1 above. See Table 1 below for names and NMR data.

Example K20: N-(2-ethoxy-5-fluoropyrimidin-4-yl)-5-{[(3S,8aS)-3-isopropylhexahydropyrrolo[1,2-a]pyrazin-2(1H)-yl]carbonyl}-6,6-dimethyl-1,4,5,6-tetrahydropyrrolo[3,4-c]pyrazol-3-amine Example K20 was prepared using methods analogous to Example K1 above, except that E4(ii) was substituted in place of (2R, 5S)-1,2,5-trimethylpiperazine hydrochloride. See Table 1 below for NMR data.

Example K21: 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine

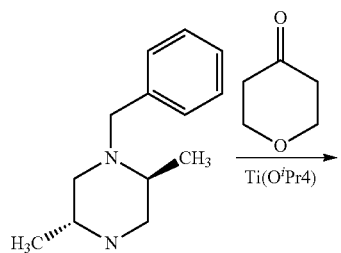

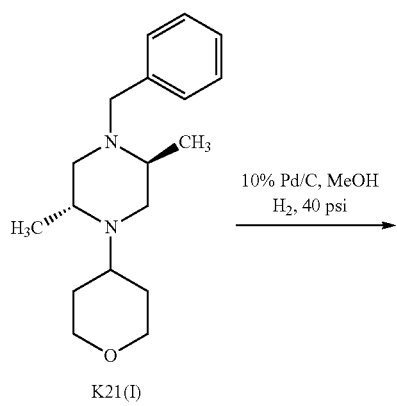

K21(I)

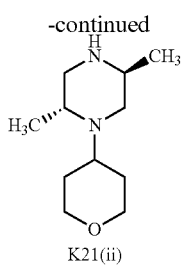

K21(ii)

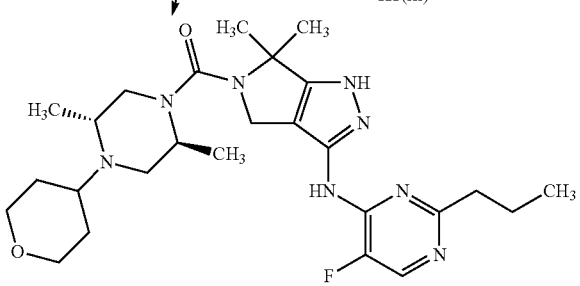

K1(iii)

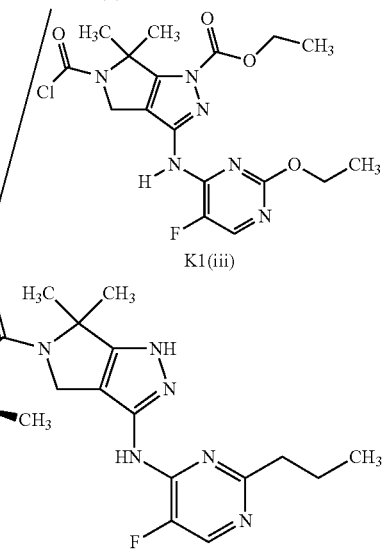

K21

Intermediate K21(i): (2S,5R)-1-benzyl-2,5-dimethyl-4-(tetrahydro-2H-pyran-4-yl)piperazine To a mixture of (2S,5R)-1-benzyl-2,5-dimethylpiperazine (11.0 g, 53.8 mmol) and of tetrahydro-4H-pyran-4-one (5.39 g, 53.8 mmol) at 0° C. was added Ti(IV) isopropoxide (19.2 mL, 67.3 mmol). The resulting mixture was stirred at rt overnight and an orange suspension was obtained. To the suspension was added EtOH (25 mL) and NaCNBH3 (4.27 g, 64.6 mmol, 1.20 eq). The resulting mixture was stirred at rt for 24 h. The reaction mixture was then quenched with water (5.0 mL) and a yellow solid was generated. The suspension was diluted with EtOAc (400 mL) and filtered. The filtrate was concentrated under reduced pressure. The residue was again diluted with EtOAc (500 mL), dried over Na2SO4, and filtered. The filtrate was collected and concentrated under reduced pressure to afford a yellow oil. The oil was diluted in THF (400 mL) and PS-isocyanate was added to remove secondary amine. The suspension was filtered and the filtrate concentrated. The residue was purified by column chromatography using 50:5:1 CHCl3/MeOH/Et3N to afford the desired compound as yellow oil (13.0 g, 84%)

Intermediate K21 (ii): (2R,5S)-2,5-dimethyl-1-(tetrahydro-2H-pyran-4-yl)piperazine. (2S,5R)-1-benzyl-2,5-dimethyl-4-(tetrahydro-2H-pyran-4-yl)piperazine (13.0 g, 45.1 mmol) was dissolved in MeOH (500 mL)

The solution was added into a Shaker container, which was previously charged with wet 10% Pd/C. Hydrogenation was carried out in shaker under 40 psi Hydrogen pressure.

The reaction was complete after 12 h. The reaction mixture was filtered through celite and the filtrate was concentrated to afford the desired compound (9.0 g, 100%). 1H NMR (300 MHz, CHLOROFORM-d) δ ppm 1.02 (d, J=3.58 Hz, 3H), 1.04 (d, J=3.39 Hz, 3H), 1.44-1.54 (m, 2H), 1.58 (dd, J=8.57, 3.67 Hz, 2H), 1.78-1.98 (m, 2H), 2.44-2.67 (m, 2H), 2.73-2.85 (m, 2H), 2.85-2.94 (m, 1H), 3.00-3.15 (m, 1H), 3.25-3.37 (m, 1H), 3.37-3.49 (m, 1H), 4.03 (dd, J=6.97, 5.46 Hz, 2H).

Example K21: 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine The title compound was prepared using methods analogous to Example K1 above. See Table 1 below for NMR data.

Example K22: 4-[((2R,5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol Example K22 was prepared using methods analagous to Example K1 above, except H8(iii) was substituted in place of (2R, 5S)-1,2,5-trimethylpiperazine. See Table 1 below for NMR data.

Examples K23-K26

Examples K23 and K24 were prepared using the method described in Example K1 above, except that E5(xi)-Isomers A and B, respectively, were substituted in place of (2R,5S)-1,2,5-trimethylpiperazine. Examples K25 and K26 were also prepared using methods analogous to Example K1 above, except that E5(xi)-Isomers A and B, respectively, were substituted in place of (2R,5S)-1,2,5-trimethylpiperazine and sodium methoxide was substituted in place of sodium ethoxide. See Table 1 below for names and NMR data.

Example L1: N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine To a solution of ethyl 3-[(2-ethoxy-5-fluoropyrimidin-4-yl)amino]-6,6-dimethyl-5,6-dihydropyrrolo[3,4-c]pyrazole-1(4H)-carboxylate dihydrochloride (120 mg, 0.27 mmol) in 15 mL THF containing diisopropylethyl amine (0.23 mL, 4 eq) was added a 5 mL THF suspension of 4-fluoro-1-methylpiperidine-4-carbonyl chloride (128 mg, 2.6 eq). After heating for 5 hours at 65° C., the reaction was concentrated to dryness and carried on without further purification. To a solution of ethyl 3-[(2-ethoxy-5-fluoropyrimidin-4-yl)amino]-5-[(4-fluoro-1-methylpiperidin-4-yl)carbonyl]-6,6-dimethyl-5,6-dihydropyrrolo[3,4-c]pyrazole-1(4H)-carboxylate in methanol was added 2 mL of a 10% sodium hydroxide solution in methanol. After removing the solvent in vacuo, the residue was purified as in Example K1 above. See Table 1 below for NMR data.

Examples L2-L4

Examples L2 through L4 were prepared using methods analogous to Example L1 above. See Table 1 below for names and NMR data.

Example L5: N-(2-ethoxy-5-fluoropyrimidin-4-yl)-6,6-dimethyl-5-{[1-(3,3,3-trifluoropropyl)piperidin-4-yl]carbonyl}-1,4,5,6-tetrahydropyrrolo[3,4-c]pyrazol-3-amine

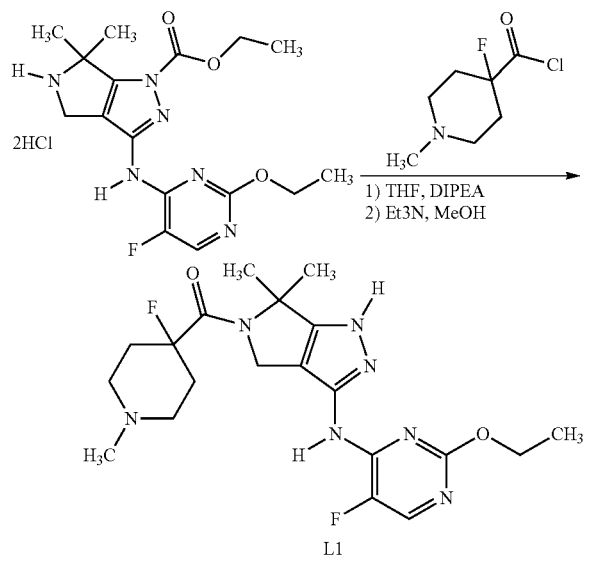

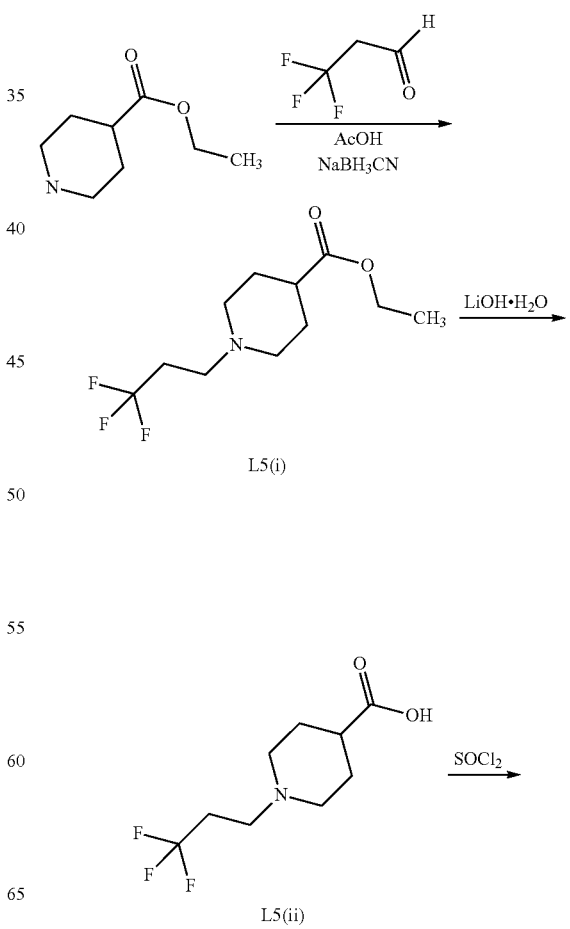

Intermediate L5(i): Ethyl 1-(3,3,3-trifluoropropyl)piperidine-4-carboxylate

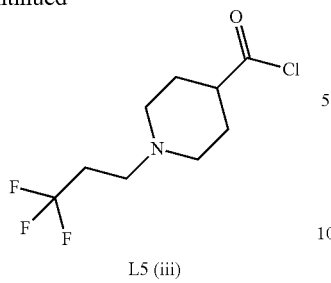

L5 (iii)

To a solution of ethyl isonipecotate (3.00 g, 19.1 mmol) in THF (20 mL) and MeOH (20 mL) was added 3,3,3-trifluoropropionaldehyde (2.14 g, 19.1 mmol) and AcOH (1.09 mL, 19.1 mmol) followed by sodium cyanoborohydride (1.20 g, 19.1 mmol). The reaction was allowed to stir for 10 min., at which time the reaction was quenched with water (15 mL) then made basic with NaHCO$_3$ and extracted with EtOAc. The organic layer was washed with brine, dried and concentrated in vacuo to yield a white powder (3.3 g, 68%). Mass Spectrum: Calcd for $C_{11}H_{19}NF_3O_2$ (M+H): 254. Found: 254.

Intermediate L5(ii): 1-(3,3,3-trifluoropropyl)piperidine-4-carboxylic Acid

To a solution of ethyl 1-(3,3,3-trifluoropropyl)piperidine-4-carboxylate (3.30 g, 13.0 mmol) in THF (40 mL) and MeOH (40 mL) was added LiOH—H$_2$O (1.64 g, 39.1 mmol). The reaction was allowed to stir for 15 h at which time the solution was filtered to remove undissolved solids and the filtrate concentrated. The resulting material was diluted with water (10 mL), made to pH 5 with HCl (conc), then concentrated in vacuo to yield a white solid (2.9 g, 150%). Mass Spectrum: Calcd for $C_9H_{15}NF_3O_2$ (M+H): 226. Found: 226.

Intermediate L5(iii): 1-(3,3,3-trifluoropropyl)piperidine-4-carbonyl Chloride A suspension of 1-(3,3,3-trifluoropropyl)piperidine-4-carboxylic acid (4.40 g, 20.0 mmol) in thionyl chloride (20 mL) was heat to 80° C. for 15 h. The solution was cooled and concentrated in vacuo to yield a brown foam (3.0 g, 68%).

Example L5: N-(2-ethoxy-5-fluoropyrimidin-4-yl)-6,6-dimethyl-5-{[1-(3,3,3-trifluoropropyl)piperidin-4-yl]carbonyl}-1,4,5,6-tetrahydropyrrolo[3,4-c]pyrazol-3-amine The title compound L5 was prepared using methods analogous for the preparation of example L1 above, except 4-fluoro-1-methylpiperidine-4-carbonyl chloride was substituted with intermediate L5(iii). See Table 1 below for NMR data.

Example L6: N-(2-ethoxy-5-fluoropyrimidin-4-yl)-6,6-dimethyl-5-{[1-(tetrahydro-2H-pyran-4-yl)piperidin-4-yl]carbonyl}-1,4,5,6-tetrahydropyrrolo[3,4-c]pyrazol-3-amine

Intermediate L6(i): (1-(tetrahydro-2H-pyran-4-yl)piperidine-4-carbonyl Chloride

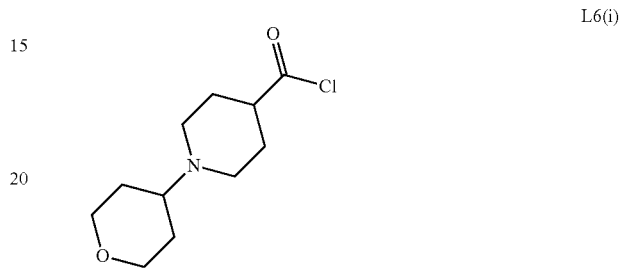

L6(i)

Intermediate L(i) was prepared using methods analogous to intermediate L5 above, except tetrahydro-2H-pyran-4-carbaldehyde was substituted in place of 3,3,3-trifluoropropionaldehyde.

Example L6: N-(2-ethoxy-5-fluoropyrimidin-4-yl)-6,6-dimethyl-5-{[1-(tetrahydro-2H-pyran-4-yl)piperidin-4-yl]carbonyl}-1,4,5,6-tetrahydropyrrolo[3,4-c]pyrazol-3-amine The title compound L6 was prepared using methods analogous to L1 above, except 4-fluoro-1-methylpiperidine-4-carbonyl chloride was substituted with intermediate L6(i). See Table 1 below for NMR data.

Example M1: N-(4-ethoxypyrimidin-2-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine

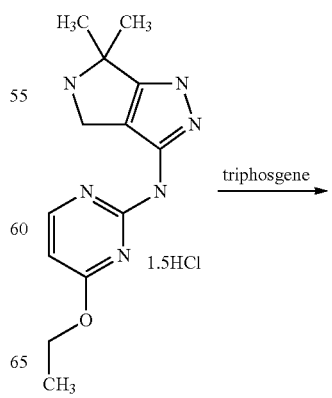

-continued

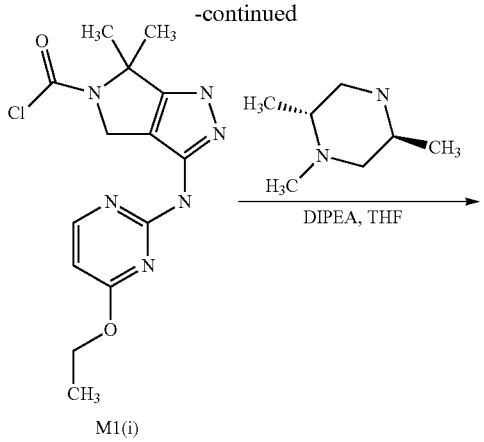

M1(i)

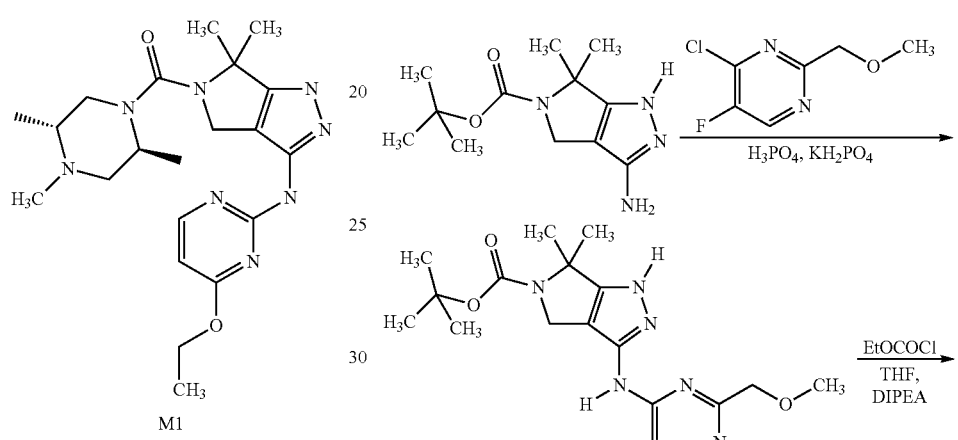

M1

Intermediate M1(i): 3-[(4-ethoxypyrimidin-2-yl) amino]-6,6-dimethyl-4,6-dihydropyrrolo[3,4-c]pyrazole-5(1H)-carbonyl Chloride To a −78° C. solution of N-(4-ethoxypyrimidin-2-yl)-6,6-dimethyl-1,4,5,6-tetrahydropyrrolo[3,4-c]pyrazol-3-amine hydrochloride (0.300 g, 1.09 mmol) in $CH_2Cl_2$ (15 mL) and diisopropylethylamine (0.952 mL, 5.47 mmol) was added triphosgene (0.227 g, 0.766 mmol) in $CH_2Cl_2$ (5 mL) dropwise over 10 min. The reaction was quenched with $H_2O$ (10 mL), warmed to 22° C., and made pH 8-9 with $NaHCO_3$. The aqueous layer was extracted with $CH_2Cl_2$ (2×30 mL) and the combined organic layers washed with brine (1×30 mL), dried over $MgSO_4$, and concentrated to give the desired product M1(i) as a brown solid (0.35 g, 95%). Mass Spectrum: Calcd for $C_{14}H_{18}ClN_6O_2$ (M+H): 337. Found: 337.

Example M1: N-(4-ethoxypyrimidin-2-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine To a solution of M1(i) (0.350 g, 1.04 mmol) in THF (4 mL) was added (2R,5S)-1,2,5-trimethylpiperazine hydrochloride (0.133 g, 1.04 mmol) and DIPEA (0.905 mL, 5.20 mmol). Solution was heat to 90° C. in a sealed tube overnight. The cooled solution was filtered to remove undissolved solids, concentrated, and redissolved in DMSO. Preparative HPLC provided the desired product M1 as a white solid (0.030 g, 6.7%). See Table 1 below for NMR data.

Example M2: N-(4-ethoxypyrimidin-2-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine Example M2 was prepared using methods analogous to Example M1 above. See Table 1 below for NMR data.

Example N1: 5-{[(2S,5R)-2,5-dimethyl-4-(tetrahydro-2H-pyran-4-ylmethyl)piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine

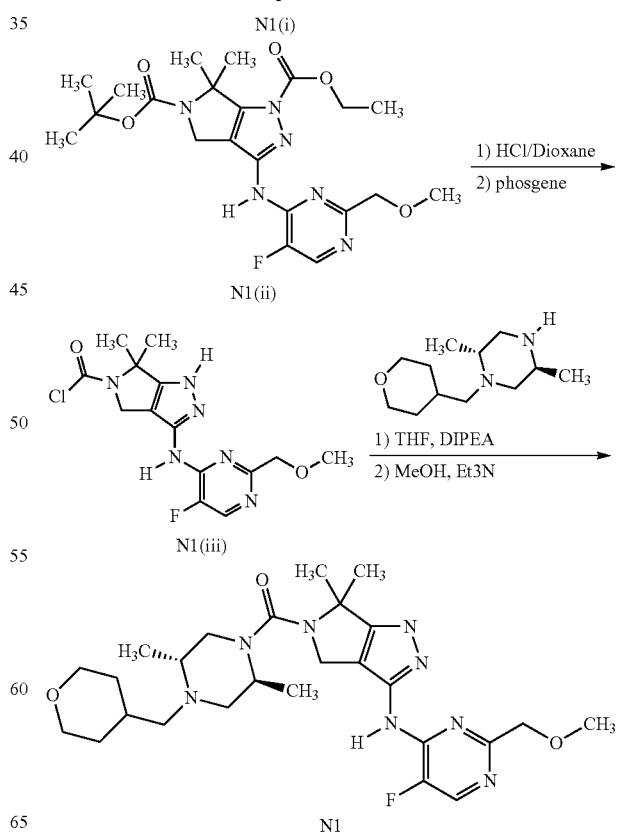

Intermediate N1(i): Tert-Butyl 3-{[5-fluoro-2-(methoxymethyl)pyrimidin-4-yl]amino}-6,6-dimethyl-4,6-dihydropyrrolo[3,4-c]pyrazole-5(1H)-carboxylate To a solution of tert-butyl 3-amino-6,6-dimethyl-4,6-dihydropyrrolo[3,4-c]pyrazole-5(1H)-carboxylate (3.00 g, 11.6 mmol) and 4-chloro-5-fluoro-2-(methoxymethyl)pyrimidine (2.06 g, 11.6 mmol) in DMSO (8 mL) was added potassium dihygrogenphosphate (1.58 g, 2.3 mmol) followed by $H_3PO_4$ (0.29 g, 2.3 mmol). The reaction was place in a 90° C. oil bath and heated for 20 h. The crude reaction was cooled to room temperature then poured into ice cold $NaHCO_3$ (60 mL) and extracted with EtOAc (2×30 mL). The combined organic extracts were washed with brine then dried ($MgSO_4$), filtered and concentrated. The crude solid was triturated with EtOAc to provide the title compound N1(i) as a white solid (3.2 g, 70%). $^1$H NMR (300 MHz, DMSO-$d_6$) δ ppm 1.44 (s, 9H), 1.59 (s, 3H), 1.61 (s, 3H), 3.34 (s, 3H), 4.29-4.44 (m, 2H), 4.45-4.64 (m, 2H), 8.32 (d, J=3.20 Hz, 1H), 10.25 (br. s., 1H), 12.24 (br. s., 1H). Mass Spectrum: Calcd for $C_{18}H_{25}FN_6O_3$ (M+H): 393. Found: 393.

Intermediate N1(ii): 5-Tert-Butyl 1-Ethyl 3-{[5-fluoro-2-(methoxymethyl)pyrimidin-4-yl]amino}-6,6-dimethyl-4,6-dihydropyrrolo[3,4-c]pyrazole-1,5-dicarboxylate A solution of N1(i) (2.90 g, 13.1 mmol) in THF (60 mL) and DIPEA (2.39 g, 18.0 mmol) was cooled in an ice bath then ethylchloroformate (0.89 g, 8.1 mmol) was added dropwise. The reaction mixture was slowly warmed to room temperature and stirred for 5 h, then quenched with water (50 mL) and extracted with EtOAc (2×100 mL). The combined extracts were washed with brine (50 mL) then dried ($MgSO_4$), filtered and concentrated to provide the title compound N1(ii) as a yellow foam (3.3 g, 96%). Mass Spectrum: Calcd for $C_{21}H_{29}FN_6O_5$ (M+H): 465. Found: 465.

Intermediate N1(iii): 3-{[5-fluoro-2-(methoxymethyl)pyrimidin-4-yl]amino}-6,6-dimethyl-4,6-dihydropyrrolo[3,4-c]pyrazole-5(1H)-carbonyl Chloride To a solution of N1(ii) (3.40 g, 7.3 mmol) in dioxane (10 mL) was added HCl (20 mL, 4M in dioxane). The reaction was stirred at room temperature for 3 h then concentrated and dried under vacuum. The HCl salt of ethyl 3-{[5-fluoro-2-(methoxymethyl)pyrimidin-4-yl]amino}-6,6-dimethyl-5,6-dihydropyrrolo[3,4-c]pyrazole-1(4H)-carboxylate was taken up in $CH_2Cl_2$ (150 mL). DIPEA (4.26 g, 5.1 mmol) was added and the reaction mixture was cooled in a dry ice/acetone bath. Triphosgene (1.52 g, 32.9 mmol) was added drop wise in a solution of $CH_2Cl_2$ (50 mL). The cold reaction was quenched with water (100 mL) and warmed to RT then extracted with $CH_2Cl_2$ (2×100 mL). The combined organic extracts were washed with brine, dried ($MgSO_4$), filtered and concentrated. The crude material was triturated with ether to give the title compound N1(iii) as a white solid (1.55 g, 50%). Mass spectrum: Calcd for $C_{17}H_{20}FClN_6O_4$ (M+H): 427. Found 427.

Example N1: 5-{[(2S,5R)-2,5-dimethyl-4-(tetrahydro-2H-pyran-4-ylmethyl)piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine To a sealed tube was added N1(iii) (420 mg, 0.98 mmol) in a solution of THF (10 mL) followed by DIPEA (445 mg, 3.4 mmol) and (2R,5S)-2,5-dimethyl-1-(tetrahydro-2H-pyran-4-ylmethyl)piperazine (209 mg, 0.98 mmol). The reaction was placed in an 85° C. oil bath and heated for 16 h. The crude reaction was concentrated then taken up in MeOH (5 mL) and $Et_3N$ (5 mL) then stirred for an addition 16 h. The crude reaction was concentrated then taken up in DCM (10 mL) and $NaHCO_3$(sat) (20 mL) and the solid was filtered, rinsed $CH_2Cl_2$ (10 mL) and water (10 mL) and dried to give the title compound N1 as a white solid (245 mg, 47%). See Table 1 below for NMR data.

Examples N2 and N3

Examples N2 and N3 were prepared using methods analogous to Example N1 above, except E5(xi)-Isomers A and B, respectively, were substituted in place of 2R,5S)-2,5-dimethyl-1-(tetrahydro-2H-pyran-4-ylmethyl)piperazine. See Table 1 below for names and NMR data.

The following Table 1 depicts further Ki app, structure, nomenclature, and NMR data of further embodiments of the invention. Unless otherwise mentioned, compounds in Table 1 were synthesized starting from commercially available materials or by known methods using routine modifications of the above described examples.

Table 1

While the invention has been illustrated by reference to specific embodiments, those skilled in the art will recognize that variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Ki app (nM) | Structure IUPAC Name | $^1$H NMR | MS (m/z) |
|---|---|---|---|---|
| A1 | 2.69 | | $^1$H NMR (300 MHz, DMSO-$d_6$ mixture of rotamers) δ ppm 0.93 (s, 3 H), 0.98-1.07 (m, 6 H), 1.08-1.20 (m, 3 H), 1.55 (s, 3 H), 1.64 (s, 3 H), 2.08 (s, 3 H), 2.14-2.29 (m, 1 H), 2.52- 2.64 (m, 2 H), 2.77- 2.94 (m, 1 H), 3.23 (s, 3 H), 4.32-4.53 (m, 2 H), 6.49 (br. s., 0.6 H), 7.09 (br. s., 0.4 H), 7.67- 8.11 (m, 1 H), 9.42 (br. s., 0.6 H), 10.14 (br. s., 0.4 H), 12.28 (br. s., 0.6 H), 12.44 (br. s., 0.4 H). | 442 |

-continued

| Ex. No. | Ki app (nM) | Structure IUPAC Name | $^1$H NMR | MS (m/z) |
|---|---|---|---|---|
| | | N4-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine | | |
| A2 | 8.75 | | $^1$H NMR (300 MHz, DMSO-d$_6$ mixture of rotamers) δ ppm 0.92 (s, 3 H), 0.96-1.08 (m, 6 H), 1.55 (s, 3 H), 1.65 (s, 3 H), 2.08 (s, 3 H), 2.11-2.24 (m, 1 H), 2.53-2.60 (m, 2 H), 2.71-2.84 (m, 1 H), 3.03 (s, 6 H), 3.16-3.28 (m, 1 H), 4.15-4.60 (m, 2 H), 7.84- 8.13 (m, 1 H), 9.40 (br. s., 0.4 H), 9.88 (br. s., 0.6 H), 12.11 (br. s., 0.6 H), 12.36 (br. s., 0.4 H). | 460 |
| | | N$^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-N$^2$,N$^2$-dimethylpyrimidine-2,4-diamine | | |
| A3 | 17.9 | | $^1$H NMR (300 MHz, DMSO-d$_6$) δ ppm 0.18 (m, 2 H), 0.35-0.51 (m, 2 H), 0.93 (s, 3 H), 0.96-1.08 (m, 7 H), 1.56 (s, 3 H), 1.65 (s, 3 H), 2.08 (s, 3 H), 2.13-2.25 (m, 1 H), 2.51-2.63 (m, 3 H), 2.84 (d, J = 11.9 Hz, 1 H), 3.00-3.19 (m, 2 H), 4.33-4.53 (m, 2 H), 6.35-7.53 (m, 1 H), 7.94 (s, 1 H), 12.51 (br. s., 1 H). | 486 |
| | | N$^2$-(cyclopropylmethyl)-N$^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine | | |
| A4 | 37.6 | | $^1$H NMR (300 MHz, DMSO-d$_6$) δ ppm 0.85-0.94 (m, 9 H), 1.02 (s, 3 H), 1.04 (d, J = 6.4 Hz, 3 H), 1.55 (s, 3 H), 1.62-1.69 (m, 3 H), 1.71-1.87 (m, 1 H), 1.90 (s, 3 H), 2.08 (s, 3 H), 2.13-2.24 (m, 1 H), 2.52-2.62 (m, 2 H), 2.83 (m, 1 H), 2.92-3.15 (m, 2 H), 4.27-4.59 (m, 2 H), 7.03 (br. s., 1 H), 7.83-8.01 (m, 1 H), 10.05 (br. s., 1 H). | 488 |
| | | N$^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-N$^2$-isobutylpyrimidine-2,4-diamine acetate salt | | |
| A5 | 3.95 | | $^1$H NMR (300 MHz, DMSO-d$_6$ mixture of rotamers) δ ppm 0.32-0.49 (m, 2 H), 0.54-0.75 (m, 2 H), 0.93 (s, 3 H), 0.97-1.12 (m, 6 H), 1.54 (s, 3 H), 1.63 (s, 3 H), 2.08 (s, 3 H), 2.12-2.25 (m, 1 H), 2.53-2.68 (m, 3 H), 2.76-2.90 (m, 1 H), 3.20-3.32 (m, 1 H), 4.15-4.63 (m, 2 H), 6.81 (br. s., 0.3 H), 7.37 (br. s., 0.7 H), 7.82-8.11 (m, 1 H), 9.47 (br. s., 0.3 H), 10.26 (br. s., 0.7 H), 12.29 (br. s., 0.3 H), 12.45 (br. s., 0.7 H). | 472 |

| Ex. No. | Ki app (nM) | Structure IUPAC Name | ¹H NMR | MS (m/z) |
|---|---|---|---|---|
| | | N2-cyclopropyl-N4-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine | | |
| A6 | 10.8 | 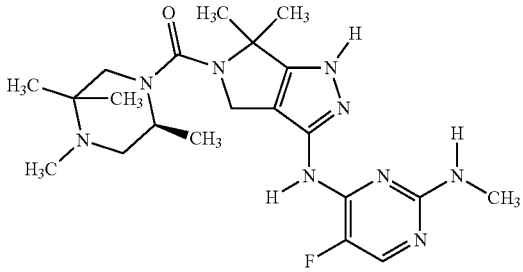<br>N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-N²-methylpyrimidine-2,4-diamine | ¹H NMR (300 MHz, DMSO-$d_6$ mixture of rotamers) δ ppm 0.93 (s, 3 H), 0.97-1.10 (m, 6 H), 1.54 (s, 3 H), 1.64 (s, 3 H), 2.08 (s, 3 H), 2.13-2.26 (m, 1 H), 2.51-2.61 (m, 2 H), 2.64-2.93 (m, 4 H), 3.16-3.32 (m, 1 H), 4.29-4.60 (m, 2 H), 6.55 (br. s., 0.3 H), 7.07 (br. s., 0.7 H), 7.76-8.12 (m, 1 H), 9.46 (br. s., 0.3 H), 10.15 (br. s.,0.7 H), 12.29 (br. s., 0.3 H), 12.43 (br. s., 0.7 H). | 446 |
| A7 | 3.81 | 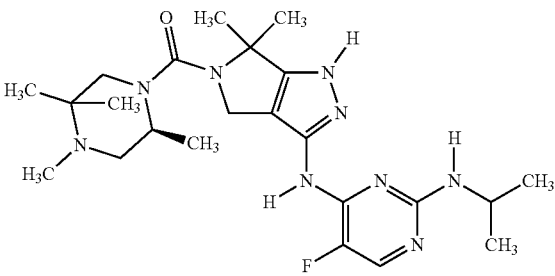<br>N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-N²-isopropylpyrimidine-2,4-diamine | ¹H NMR (300 MHz, DMSO-$d_6$ mixture of rotamers) δ ppm 0.93 (s, 3 H) 1.00-1.08 (m, 6 H) 1.10-1.16 (m, 6 H) 1.54 (s, 3 H) 1.64 (s, 3 H) 2.09 (s, 3 H) 2.14-2.26 (m, 1 H) 2.51-2.62 (m, 2 H) 2.78-2.95 (m, 1 H) 3.36-3.45 (m, 1 H) 3.90 (s, 1 H) 4.28-4.60 (m, 2 H) 6.26 (br. s., 0.3 H), 7.05 (br. s., 0.7 H), 7.76-8.11 (m, 1 H), 9.42 (br. s., 0.3 H), 10.19 (br. s., 0.7 H), 12.29 (br. s., 0.3 H), 12.50 (br. s., 0.7 H). | 474 |
| A8 | 3.39 | 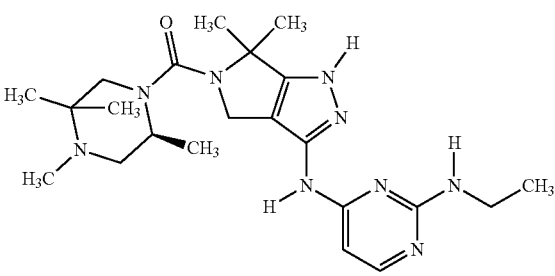<br>N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N²-ethylpyrimidine-2,4-diamine | ¹H NMR (300 MHz, DMSO-$d_6$ mixture of rotamers) δ ppm 0.93 (s, 3 H), 0.99-1.06 (m, 6 H), 1.08-1.18 (m, 3 H), 1.55 (s, 3H), 1.64 (s, 3 H), 2.09 (s, 3 H), 2.13-2.24 (m, 1 H), 2.52-2.58 (m, 2 H), 2.84 (m, 1 H), 3.22-3.30 (m, 2 H), 3.37-3.41 (m, 1 H), 4.30-4.55 (m, 2 H), 5.97 (s, 1 H), 6.31 (br. s., 0.4 H), 7.10 (br. s., 0.6 H), 7.67-7.98 (m, 1 H), 9.29 (br. s., 0.4 H), 9.84 (br. s., 0.6 H), 12.13 (br. s., 0.4 H), 12.47 (br. s., 0.6 H). | 442 |
| A9 | 9.73 | 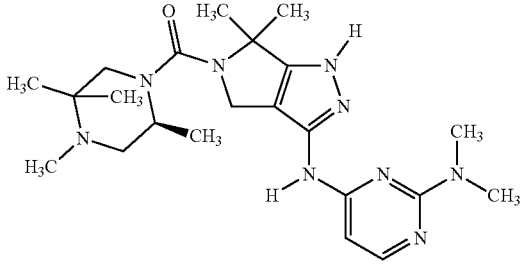 | ¹H NMR (300 MHz, DMSO-$d_6$ mixture of rotamers) δ ppm 0.93 (s, 3 H), 0.96-1.04 (m, 6 H), 1.56 (s, 3 H), 1.67 (s, 3 H), 2.08 (s, 3 H), 2.12-2.23 (m, 1 H), 2.52-2.59 (m, 2 H), 2.80 (m, 1 H), 3.06 (s, 6 H), 3.18-3.29 (m, 1 H), 4.30-4.53 (m, 2 H), 5.97 (s, 0.5 H), 6.38 (br. s., 0.5 H), 7.78-8.03 (m, 1 H), 9.24 (br. s., 0.5 H), 9.65 (br. s., 0.5 H), 12.03-12.26 (m, 1 H). | 442 |

| Ex. No. | Ki app (nM) | Structure IUPAC Name | ¹H NMR | MS (m/z) |
|---|---|---|---|---|
| A10 | 1.01 | N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N²,N²-dimethylpyrimidine-2,4-diamine | ¹H NMR (DMSO-d₆, 400 MHz) δ ppm 0.94-1.12 ( 5 H, m), 1.43 (3 H, m), 1.57 (3 H, s), 1.68 (3 H, s), 1.90 (3 H, s), 2.09 (3 H, s), 2.45 (3 H, s), 2.66 (1 H, m), 2.81 (1 H, m), 4.60 (2 H, m), 8.22 (1 H, s), 10.10 (1 H, s). | 457 |
| A11 | <10 | 5-{[(8S)-6,8-dimethyl-6,9-diazaspiro[4.5]dec-9-yl]carbonyl}-N-(5-fluoro-2-methylpyrimidin-4-yl)-6,6-dimethyl-1,4,5,6-tetrahydropyrrolo+3,4-c]pyrazol-3-amine | 1H NMR (300 MHz, DMSO-d₆) δ 0.91-1.05 (m, 6 H) 1.05-1.28 (m, 6 H) 1.47-1.61 (m, 4 H) 1.61-1.78 (m, 5 H) 1.90 (s, 3 H) 2.43 (br. s., 2 H) 2.69-2.94 (m, 2 H) 3.01-3.16 (m, 2 H) 3.17-3.29 (m, 3 H) 3.74-3.93 (m, 2 H) 4.39-4.58 (m, 2 H) 7.95 (br. s., 1 H) 10.06 (br. s., 1 H) 12.29 (br. s., 1 H) | 530 |
| A12 | <10 | N⁴-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-N²-ethyl-5-fluoropyrimidine-2,4-diamine | 1H NMR (300 MHz, DMSO-d₆) δ 0.92-1.06 (m, 6 H) 1.06-1.17 (m, 3 H) 1.37-1.50 (m, 1 H) 1.53 (br. s., 1 H) 1.56 (s, 3 H) 1.61 (br. s., 1 H) 1.65 (s, 3 H) 2.03-2.23 (m, 1 H) 2.68-2.80 (m, 2 H) 2.80-2.99 (m, 2 H) 3.02-3.16 (m, 2 H) 3.16-3.31 (m, 6 H) 3.81-3.97 (m, 2 H) 4.38-4.55 (m, 1 H) 7.95 (d, J = 3.01 Hz, 1 H) | 516 |
| AA1 | 22.9 | N⁴-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo+3,4-c]pyrazol-3-yl)-N²-ethyl-5-fluoropyrimidine-2,4-diamine | ¹H NMR (400 MHz, DMSO-d₆) δ ppm 0.98 (6 H, s), 1.58 (3 H, s), 1.67 (3 H, s), 1.90 (3 H, s), 2.77 (2 H, bm), 3.05 (2 H, bm), 3.32 (8 H, s), 3.82 (3 H, s), 4.59-4.73 (2 H, m), 8.13 (1 H, s), 10.19 (1 H, s), 11.95 (1 H, s). | 447 |

| Ex. No. | Ki app (nM) | Structure IUPAC Name | ¹H NMR | MS (m/z) |
|---|---|---|---|---|
| AA2 | 18.9 | 5-{[(2S,5R)-4-ethyl-2,5-dimethylpiperazin-1-yl]carbonyl}-N-(5-fluoro-2-methoxypyrimidin-4-yl)-6,6-dimethyl-1,4,5,6-tetrahydropyrrolo[3,4-c]pyrazol-3-amine | ¹H NMR (400 MHz, DMSO-$d_6$) δ ppm 0.98 (8 H, d, J = 4.04 Hz), 1.59 (3 H, s), 1.68 (3 H, s), 1.91 (1 H, s), 2.38 (2 H, s), 2.47 (3 H, s), 2.74 (1 H, s), 3.05 (2 H, s), 3.32 (18 H, s), 4.70 (2 H, s), 8.21 (1 H, s). | 431 |
| AA3 | 14.8 | 5-{[(2S,5R)-4-ethyl-2,5-dimethylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine | ¹H NMR (400 MHz, DMSO-$d_6$) δ ppm 0.91-0.99 (10 H, m), 1.58 (3 H, s), 1.68 (3 H, s), 1.90 (3H, s), 1.93 (1 H, d, J = 10.86 Hz), 2.26-2.30 (3 H, m), 2.31-2.40 (3 H, m), 2.43 (3 H, s), 2.66-2.78 (2 H, m), 3.04 (2 H, d, J = 8.34 Hz), 4.63-4.74 (2 H, m). | 445 |
| AA4 | 147 | 5-{[(2S,5R)-4-ethyl-2,5-dimethylpiperazin-1-yl]carbonyl}-N-(5-fluoro-2,6-dimethylpyrimidin-4-yl)-6,6-dimethyl-1,4,5,6-tetrahydropyrrolo[3,4-c]pyrazol-3-amine | ¹H NMR (400 MHz, CDCl$_3$) δ ppm 1.09 (d, J = 8 Hz, 3 H), 1.33 (d, J = 8 Hz, 3 H), 1.72 (s, 3 H), 1.76 (s, 3 H), 2.21 (m, 1H), 2.27 (s, 3H), 2.45 (m, 1 H), 2.57 (s, 3H), 2.66-2.69 (m, 1 H), 2.92-2.98 (m, 1 H), 3.18-3.22 (m, 1H), 3.86 (m, 1H), 4.60 (d, J = 16 Hz, 1 H), 4.69 (d, J = 16 Hz, 1 H), 8.11 (s, 1H) | 417 |
| AA5 | 29.1 | 2(S),5(S)-{[dimethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine | ¹H NMR (400 MHz, CD$_3$OD) δ ppm 1.13 (d, J = 8 Hz, 3 H), 1.21 (d, J = 8 Hz, 3 H), 1.71 (s, 3 H), 1.79 (s, 3 H), 1.81 (m, 2H), 2.43 (m, 1H), 2.56 (s, 3H), 2.71 (m, 2 H), 2.76 (m, 1 H), 3.12 (m, 1 H), 3.19 (m, 1H), 3.26 (m, 2H), 3.65 (m, 2H), 4.81 (m, 2 H), 8.11 (s, 1H) | 461 |

| Ex. No. | Ki app (nM) | Structure / IUPAC Name | ¹H NMR | MS (m/z) |
|---|---|---|---|---|
| | | [3-(5-fluoro-2-methyl-pyrimidin-4-ylamino)-6,6-dimethyl-4,6-dihydro-1H-pyrrolo[3,4-c]pyrazol-5-yl]-[4-(3-hydroxy-propyl)-2,5-dimethyl-piperazin-1-yl]-methanone | | |
| B1 | 5.09 | N²-ethyl-5-fluoro-N⁴-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine acetate salt | ¹H NMR (300 MHz, DMSO-d₆) δ ppm 0.93-1.01 (m, 6 H), 1.11 (t, J = 7.2 Hz, 3 H), 1.56 (s, 3 H), 1.58-1.63 (m, 2 H), 1.65 (s, 3 H), 1.85-1.96 (m, 2 H), 2.13-2.26 (m, 1 H), 2.32-2.43 (m, 2 H), 2.60-2.72 (m, 1 H), 2.73-2.81 (m, 1 H), 2.98-3.14 (m, 2 H), 3.22-3.28 (m, 2 H), 3.29-3.37 (m, 4 H), 4.40-4.55 (m, 2 H), 6.94 (br. s., 1 H), 7.65-8.09 (m, 1 H), 10.09 (br. s., 1 H), 12.33 (br. s., 1 H). | 504 |
| B2 | 24.5 | N⁴-(6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-yl)-N²-ethyl-5-fluoropyrimidine-2,4-diamine | ¹H NMR (300 MHz, DMSO-d₆ mixture of rotamers) δ ppm 1.02-1.16 (m, 3 H), 1.21 (m, 3 H), 1.30 (m, 1 H), 1.58 (m, 6 H), 1.67-1.89 (m, 3 H), 1.87-2.03 (m, 1 H), 2.11-2.27 (m, 1 H), 2.63-2.85 (m, 2 H), 2.85-3.00 (m, 1 H), 3.23 (m, 2 H), 3.30-3.44 (m, 2 H), 3.74-3.98 (m, 1 H), 4.20-4.56 (m, 2 H), 6.46 (br. s., 0.3 H), 7.12 (br. s, 0.7 H), 7.77-8.11 (m, 1 H), 9.46 (br. s., 0.3 H), 10.18 (br. s., 0.7 H), 12.28 (br. s.,0.3 H), 12.42 (br. s., 0.7 H). | 458 |
| B3 | 2.03 | N⁴-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-N²-ethyl-5-fluoropyrimidine-2,4-diamine | ¹H NMR (300 MHz, DMSO-d₆) δ ppm 0.93 (d, J = 5.65 Hz, 3 H) 0.97 (d, J = 6.03 Hz, 3 H) 1.12 (t, J = 6.88 Hz, 3 H) 1.57 (s, 3 H) 1.66 (s, 3 H) 1.76-1.88 (m, 1 H) 2.00-2.10 (m, 1 H) 2.14 (s, 3 H) 2.24-2.38 (m, 1 H) 2.69 (d, J = 9.80 Hz, 1 H) 2.92-3.16 (m, 2 H) 3.18-3.31 (m, 2 H) 4.35-4.60 (m, 2 H) 7.09 (br. s., 1 H) 7.96 (s, 1 H) 10.24 (br. s., 1 H) 12.47 (br. s., 1 H). | 446.4 |

-continued

| Ex. No. | Ki app (nM) | Structure IUPAC Name | $^1$H NMR | MS (m/z) |
|---|---|---|---|---|
| B4 | 13.5 | 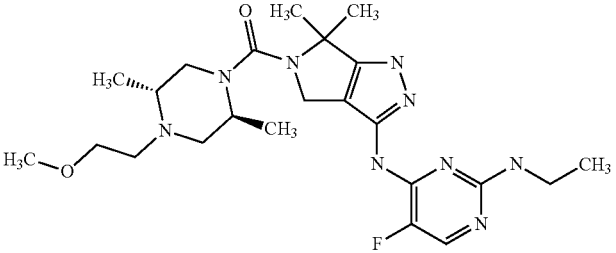 [SMILES: CCNc1ncc(F)c(Nc2n[nH]c3c2CN(C(=O)N2C[C@@H](C)N(CCOC)C[C@@H]2C)C3(C)C)n1]<br>N$^2$-ethyl-5-fluoro-N$^4$-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine | $^1$H NMR (300 MHz, DMSO-d$_6$) δ ppm 0.92-1.01 (m, 6 H), 1.11 (t, J = 7.2 Hz, 3 H), 1.56 (s, 3 H), 1.65 (s, 3 H), 1.98-2.09 (m, 1 H), 2.29-2.48 (m, 3 H), 2.73-2.87 (m, 2 H), 2.97-3.05 (m, 1 H), 3.09 (d, J = 9.8 Hz, 1 H), 3.17-3.29 (m, 5 H), 3.40 (t, J = 5.9 Hz, 2 H), 4.39-4.57 (m, 2 H), 6.93 (br. s., 1 H), 7.95-8.01 (m, 1 H), 10.08 (br. s., 1 H), 12.18 (br. s., 1 H). | 490.4 |
| B5 | 29.8 | 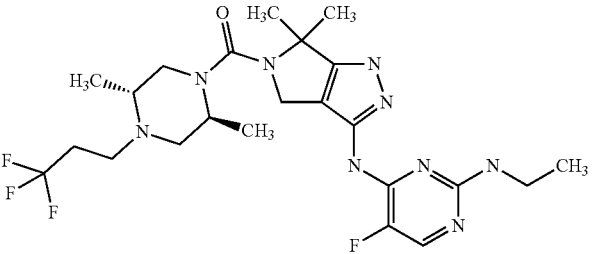 [SMILES: CCNc1ncc(F)c(Nc2n[nH]c3c2CN(C(=O)N2C[C@@H](C)N(CCC(F)(F)F)C[C@@H]2C)C3(C)C)n1]<br>N4-(5-{[(2S,5R)-2,5-dimethyl-4-(3,3,3-trifluoropropyl)piperazin-1-yl]carbonyl}-6,6-dimethyl-1,4,5,6-tetrahydropyrrolo[3,4-c]pyrazol-3-yl)-N2-ethyl-5-fluoropyrimidine-2,4-diamine | 1H NMR (300 MHz, DMSO-d6) 0.91-1.05 (m, 6 H) 1.06-1.18 (m, 3 H) 1.57 (s, 3 H) 1.65 (s, 3 H) 1.89-2.04 (m, 1 H) 2.32-2.48 (m, 6 H) 2.74-2.90 (m, 2 H) 3.02-3.15 (m, 2 H) 3.16-3.28 (m, 3 H) 4.47 (s, 2 H) 7.85-8.00 (m, 1 H) 10.26 (bs, 1H). | 528 |
| B6 | 2.43 | 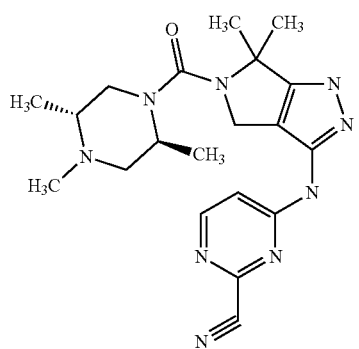 [SMILES: C[C@@H]1CN(C(=O)N2Cc3c(Nc4ccnc(C#N)n4)n[nH]c3C2(C)C)[C@@H](C)CN1C]<br>4-[(6,6-dimethyl-5-{[(2S,5R)-2,4,5-trimethylpiperazin-1-yl]carbonyl}-1,4,5,6-tetrahydropyrrolo[3,4-c]pyrazol-3-yl)amino]pyrimidine-2-carbonitrile | 1H NMR (300 MHz, DMSO-d$_6$) 0.91-1.05 (m, 3 H) 1.14-1.29 (m, 6 H) 1.60 (s, 3 H) 1.69 (s, 3 H) 2.18 (s, 3 H) 2.27-2.42 (m, 1 H) 2.64-2.78 (m, 1 H) 2.96-3.11 (m, 2 H) 3.16 (s, 1 H) 4.59-4.72 (m, 2 H) 6.96-7.00 (m, 1H) 8.30-8.40 (m, 1 H) | 410 |

-continued

| Ex. No. | Ki app (nM) | Structure IUPAC Name | $^1$H NMR | MS (m/z) |
|---|---|---|---|---|
| B7 | 20.1 | 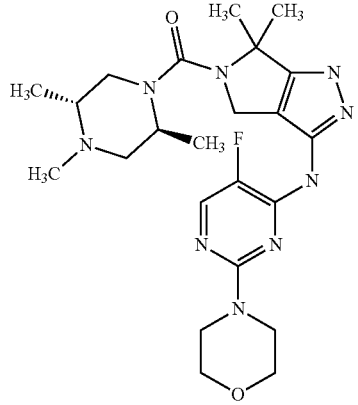 [SMILES: C[C@@H]1CN(C(=O)N2Cc3c(Nc4nc(N5CCOCC5)ncc4F)n[nH]c3C2(C)C)[C@@H](C)CN1C]<br>N-(5-fluoro-2-morpholin-4-ylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine | 1H NMR (300 MHz, DMSO-d$_6$) 0.89-1.02 (m, 6 H) 1.59 (s, 3 H) 1.66 (s, 3 H) 1.78-1.89 (m, 1 H) 1.95-2.08 (m, 1 H) 2.13 (s, 3 H) 2.23-2.36 (m, 1 H) 2.64-2.76 (m, 1 H) 2.90-3.05 (m, 2 H) 3.50-3.57 (m, 4 H) 3.57-3.68 (m, 4 H) 4.30-4.41 (m, 1 H) 4.42-4.52 (m, 1 H) 8.02 (s, 1 H) 9.76 (bs, 1H) 12.22 (bs, 1H). | 488 |
| C1 | 33.4 | 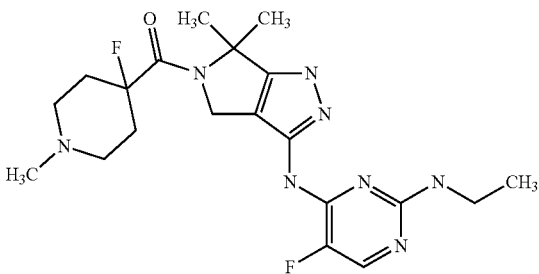 [SMILES: CCNc1ncc(F)c(Nc2n[nH]c3c2CN(C(=O)C2(F)CCN(C)CC2)C3(C)C)n1]<br>N$^2$-ethyl-5-fluoro-N$^4$-{5-[(4-fluoro-1-methylpiperidin-4-yl)carbonyl]-6,6-dimethyl-1,4,5,6-tetrahydropyrrolo[3,4-c]pyrazol-3-yl}pyrimidine-2,4-diamine | $^1$H NMR (300 MHz, DMSO-d$_6$) δ ppm 1.11 (m, 3 H), 1.66 (s, 6 H), 1.88-2.15 (m, 6 H), 2.17 (s, 3 H), 2.59-2.73 (m, 2 H), 3.12-3.29 (m, 2 H), 4.65-4.85 (m, 2 H), 6.22 (br. s., 0.2 H), 7.09 (br. s., 0.8 H), 7.97 (s, 1 H), 9.57 (br. s.,0.2 H), 10.34 (br. s., 0.8 H), 12.35 (br. s., 0.2 H), 12.54 (br. s., 0.8 H). | 435 |
| D1 | 5.43 | 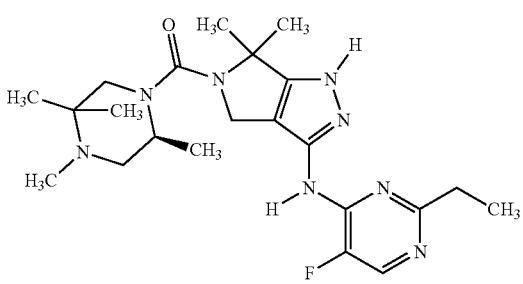<br>N-(2-ethyl-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine | $^1$H NMR (300 MHz, DMSO-d$_6$ mixture of isomers) δ ppm 0.90 (br. s., 3 H), 0.96 (br. s., 3 H), 1.06 (d, J = 6.2 Hz, 3 H), 1.22 (t, J = 7.5 Hz, 3 H), 1.57 (s, 3 H), 1.69 (s, 3 H), 2.08 (s, 3 H), 2.13-2.25 (m, 1 H), 2.53-2.66 (m, 2 H), 2.66-2.78 (m, 2 H), 2.77-2.91 (m, 1 H), 3.37-3.51 (m, 1 H), 4.37-4.86 (m, 2 H), 8.11-8.43 (m, 1 H), 9.99 (br. s., 0.6 H), 10.20 (br. s., 0.4 H), 11.96 (br. s., 0.4 H), 12.40 (br. s., 0.6 H). | 445 |
| E1 | 10.5 | 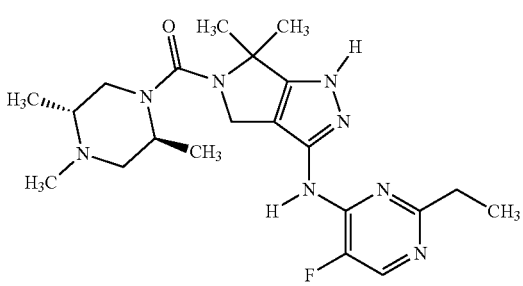 [SMILES: CCc1ncc(F)c(Nc2n[nH]c3c2CN(C(=O)N2C[C@@H](C)N(C)C[C@@H]2C)C3(C)C)n1] | $^1$H NMR (300 MHz, DMSO-d$_6$) δ ppm 0.85-0.99 (m, 6 H), 1.20-1.31 (m, 3 H), 1.59 (s, 3H), 1.68 (s, 3 H), 1.73-1.88 (m, 1 H), 1.90 (s, 3 H), 1.96-2.07 (m, 1 H), 2.10-2.18 (m, 3 H), 2.25-2.39 (m, 1 H), 2.64-2.82 (m, 3 H), 2.89-3.06 (m, 3 H), 4.53-4.91 (m, 2 H), 8.24 (s, 1 H), 10.15 (s, 1 H). | 431 |

-continued

| Ex. No. | Ki app (nM) | Structure IUPAC Name | ¹H NMR | MS (m/z) |
|---|---|---|---|---|
| | | N-(2-ethyl-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine acetate salt | | |
| E2 | 1.64 | N-(2-ethyl-5-fluoropyrimidin-4-yl)-5-{[(2S,5R)-4-(3-methoxpropyl)-2,5-dimethylpiperazin-1-yl]carbonyl}-6,6-dimethyl-1,4,5,6-tetrahydropyrrolo[3,4-c]pyrazol-3-amine | ¹H NMR (300 MHz, DMSO-d₆) δ ppm 0.86-0.92 (m, 1 H), 0.92-0.99 (m, 6 H), 1.18-1.30 (m, 3 H), 1.55-1.65 (m, 5 H), 1.68 (s, 3 H), 1.83-1.98 (m, 1 H), 2.10-2.26 (m, 1 H), 2.30-2.44 (m, 2 H), 2.62-2.83 (m, 4 H), 2.95-3.12 (m, 2 H), 3.19-3.25 (m, 3 H), 3.27-3.33 (m, 1 H), 4.47-4.98 (m, 2 H), 8.25 (s, 1 H), 10.06 (s, 1 H), 11.71-12.69 (m, 1 H). | 489 |
| E3 | 13.1 | N-(2-ethoxypyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine | ¹H NMR (400 MHz, DMSO-d₆) δ ppm 0.96 (dd, J = 11.75, 5.94 Hz, 6 H), 1.31 (q, J = 6.74 Hz, 3 H), 1.55-1.61 (m, 3 H), 1.67 (s, 3H), 1.88 (s, 3 H), 2.10-2.14 (m, 1 H), 2.16 (s, 3 H), 2.33 (t, J = 10.61 Hz, 1 H), 2.67-2.74 (m, 1 H), 2.95-3.04 (m, 2 H), 3.30 (s, 1 H), 3.35 (d, J = 5.05 Hz, 2 H), 4.25-4.36 (m, 2 H), 4.61-4.71 (m, 2 H), 8.03 (d, J = 5.56 Hz, 1 H). | 429 |
| E4 | 31.5 | 5-{[(2S,5R)-2,5-dimethyl-4-(3,3,3-trifluoropropyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine | 1H NMR (300 MHz, DMSO-d₆) 0.93-1.04 (m, 6 H) 1.20-1.29 (m, 3 H) 1.59 (s, 3 H) 1.69 (s, 3 H) 1.91-2.02 (m, 1 H) 2.35-2.48 (m, 1 H) 2.70-2.78 (m, 1 H) 2.78-2.91 (m, 2 H) 2.99-3.12 (m, 1 H) 3.15-3.23 (m, 4 H) 4.06-4.18 (m, 2 H) 4.64-4.79 (m, 2 H) 8.26 (s, 1 H). | 513 |
| E5 | <10 | | ¹H NMR (300 MHz, DMSO-d₆) δ ppm 0.93 (d, J = 6.03 Hz, 3 H), 1.25 (t, J = 7.63 Hz, 3 H), 1.37-1.53 (m, 1 H), 1.59 (s, 3 H), 1.64-1.77 (m, 4 H), 1.80-1.90 (m, 2 H), 2.16 (s, 3 H), 2.36-2.47 (m, 1 H), 2.66-2.86 (m, 3 H), 2.93-3.14 (m, 2 H), 3.37-3.51 (m, 2 H), 4.58-4.87 (m, 2 H), 8.26 (s, 1 H), 10.11 (s, 1 H), 12.41 (br. s., 1 H). | 461 |

| Ex. No. | Ki app (nM) | Structure IUPAC Name | ¹H NMR | MS (m/z) |
|---|---|---|---|---|
| | | 2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol | | |
| F1 | 39.9 | 5-[(4-fluoro-1-methylpiperidin-4-yl)carbonyl]-N-(5-fluoro-2-methylpyrimidin-4-yl)-6,6-dimethyl-1,4,5,6-tetrahydropyrrolo[3,4-c]pyrazol-3-amine | ¹H NMR (300 MHz, DMSO-$d_6$) δ 1.67 (s, 6 H) 1.88 (s, 3 H) 1.96-1.98 (m, 2 H) 2.06-2.18 (m, 2 H) 2.43 (s, 3 H) 2.62-2.73 (m, 2 H) 3.17-3.19 (m, 4 H) 4.98-4.99 (m, 2 H) 8.19-8.21 (m, 1 H). | 406 |
| G1 | 25.4 | N-(2-ethyl-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine | ¹H NMR (300 MHz, DMSO-$d_6$) δ 1.15-1.27 (m, 3 H) 1.68 (s, 6 H) 1.75 (s, 1 H) 1.87-2.01 (m, 2 H) 2.02-2.15 (m, 3 H) 2.18 (s, 3 H) 2.61-2.75 (m, 4 H) 3.16 (s, 2 H) 4.91-5.01 (m, 2 H) 8.22 (s, 1 H). | 420 |
| H1 | 39.8 | N-(5-fluoro-2-methylpyrimidin-4-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine | ¹H NMR (300 MHz, DMSO-$d_6$) δ 1.11-1.23 (m, 3 H) 1.24-1.38 (m, 1 H) 1.54 (s, 3 H) 1.61 (s, 3 H) 1.66-1.82 (m, 3 H) 1.90 (s, 3 H) 1.91-2.00 (m, 1 H) 2.14-2.24 (m, 1 H) 2.44 (s, 3 H) 2.70-2.84 (m, 2 H) 2.86-3.00 (m, 1 H) 3.78-3.93 (m, 1 H) 4.42-4.55 (m, 1 H) 4.58-4.72 (m, 1 H) 8.16-8.22 (m, 1 H), 10.1 (bs, 1H). | 429 |
| H2 | 18.1 | N-(5-fluoro-2-methylpyrimidin-4-yl)-6,6-dimethyl-5-{[(2S,5R)-2,4,5-trimethylpiperazin-1- | ¹H NMR (300 MHz, DMSO-$d_6$) δ 0.89-0.99 (m, 6 H) 1.55 (s, 3 H) 1.68 (s, 3 H) 1.73-1.85 (m, 1 H) 1.89 (s, 1 H) 1.97-2.09 (m, 1 H) 2.15 (s, 3 H) 2.25-2.39 (m, 1 H) 2.47 (s, 3 H) 2.63-2.76 (m, 1 H) 2.92-3.06 (m, 2 H) 4.63-4.78 (m, 2 H) 8.17-8.23 (m, 1 H) 10.21 (s, 1 H). | 417 |

-continued

| Ex. No. | Ki app (nM) | Structure IUPAC Name | ¹H NMR | MS (m/z) |
|---|---|---|---|---|
| | | yl]carbonyl}-1,4,5,6-tetrahydropyrrolo[3,4-c]pyrazol-3-amine | | |
| H3 | 7.21 | N-(5-fluoro-2-methylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine | ¹H NMR (400 MHz, DMSO-d₆) δ ppm 0.91 (3 H, s), 0.95-1.02 (3 H, m), 1.06 (3 H, d, J = 6.06 Hz), 1.57 (2 H, s), 1.68 (2 H, s), 1.91 (3 H, s), 2.09 (2 H, s), 2.20 (1 H, s), 2.45 (2 H, s), 2.61 (1 H, s), 2.81 (1 H, s), 3.33 (9 H, s), 4.60 (1 H, d, J = 7.58 Hz), 8.22 (1 H, s) | |
| H4 | 86 | 5-{[(3S)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine | ¹H NMR (400 MHz, DMSO-d₆) δ ppm 0.81 (t, J = 7.45 Hz, 3H), 1.37 (dt, J = 14.46, 7.29 Hz, 1 H), 1.55 (td, J = 7.14, 2.65 Hz, 1 H), 1.57-1.65 (m, 7 H), 1.86-1.94 (m, 1 H), 2.08-2.14 (m, 1 H), 2.16 (s, 4 H), 2.46 (s, 3 H), 2.66-2.74 (m, 1 H), 2.76-2.83 (m, 1 H), 3.21-3.28 (m, 2 H), 4.61 (s, 2 H), 8.20 (s, 1 H) | 417 |
| H5 | 50.8 | 5-{[(3R)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine | ¹H NMR (400 MHz, DMSO-d₆) δ ppm 0.80 (t, J = 7.45 Hz, 3H), 1.37 (dt, J = 14.40, 7.20 Hz, 1 H), 1.56 (dd, J = 14.15, 7.58 Hz, 1 H), 1.62 (s, 6 H), 1.87-1.93 (m, 4 H), 2.08-2.14 (m, 1 H), 2.16 (s, 3 H), 2.46 (s, 3 H), 2.54 (d, J = 10.36 Hz, 1 H), 2.71 (d, J = 11.37 Hz, 1 H), 3.25 (t, J = 14.02 Hz, 2 H), 3.33 (s, 4 H), 4.61 (s, 2 H), 8.21 (d, J = 3.28 Hz, 1 H) | 417 |

-continued

| Ex. No. | Ki app (nM) | Structure IUPAC Name | ¹H NMR | MS (m/z) |
|---|---|---|---|---|
| H6 | 14.9 | 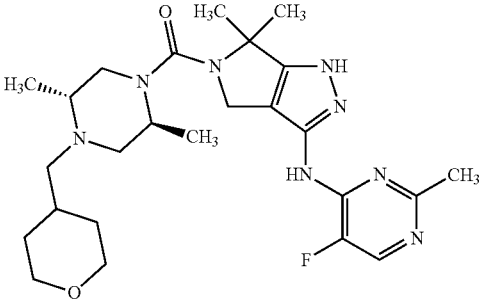 [SMILES: Cc1ncc(F)c(Nc2n[nH]c3c2CN(C(=O)N2C[C@@H](C)N(CC4CCOCC4)C[C@@H]2C)C3(C)C)n1]5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine | 1H NMR (300 MHz, DMSO-d₆) δ 0.91-1.01 (m, 6 H) 1.01-1.20 (m, 3 H) 1.50 (br. s., 1 H) 1.54-1.62 (m, 4 H) 1.68 (s, 6 H) 1.80-1.89 (m, 2 H) 2.46 (s, 4 H) 2.53-2.55 (m, 1 H) 2.76-2.90 (m, 1 H) 3.02-3.17 (m, 2 H) 3.20-3.30 (m, 2 H) 3.75-3.90 (m, 2 H) 4.62-4.78 (m, 2 H) 8.21 (d, J = 3.39 Hz, 1 H) 10.12 (br. s., 1 H) 12.19 (br. s., 1 H) | 501 |
| H7 | 22.0 | 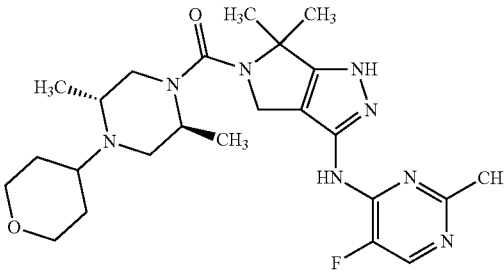5-{[(2S,5R)-2,5-dimethyl-4-(tetrahydro-2H-pyran-4-yl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine | 1H NMR (300 MHz, DMSO-d₆) δ 0.92-1.10 (m, 6 H) 1.13-1.25 (m, 1 H) 1.50-1.62 (m, 4 H) 1.68 (s, 3 H) 2.09 (br. s., 2 H) 2.47 (br. s., 3 H) 2.53-2.57 (m, 2 H) 2.65-2.95 (m, 4 H) 3.00-3.17 (m, 4 H) 3.80-3.96 (m, 2 H) 4.63-4.77 (m, 2 H) 8.20 (br. s., 1 H) 10.12 (br. s., 1 H) | 487 |
| H8 | 157 | 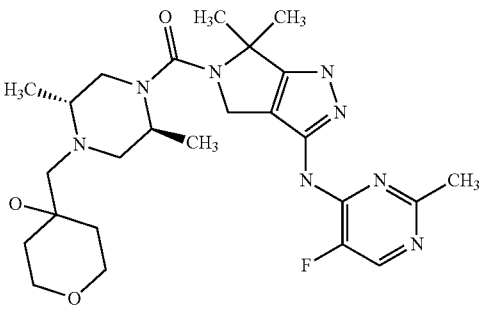 [SMILES: Cc1ncc(F)c(Nc2n[nH]c3c2CN(C(=O)N2C[C@@H](C)N(CC4(O)CCOCC4)C[C@@H]2C)C3(C)C)n1]4-[((2R,5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol | ¹H NMR (300 MHz, DMSO-d₆) δ ppm 0.95 (d, J = 5.27 Hz, 3 H), 1.00 (d, J = 6.03 Hz, 3 H), 1.23-1.45 (m, 2 H), 1.49-1.64 (m, 5 H), 1.68 (s, 3 H), 2.01-2.17 (m, 2 H), 2.32-2.61 (m, 6 H), 2.94-3.18 (m, 2 H), 3.19-3.28 (m, 1 H), 3.49-3.69 (m, 4 H), 4.09 (br. s., 1 H), 4.67 (s, 2 H), 8.21 (d, J = 3.58 Hz, 1 H), 10.15 (s, 1 H), 12.20 (br. s., 1 H). | 517 |
| H9 | 58.2 | 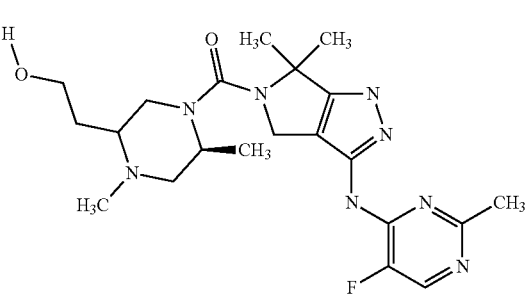 [SMILES: Cc1ncc(F)c(Nc2n[nH]c3c2CN(C(=O)N2CC(CCO)N(C)C[C@@H]2C)C3(C)C)n1] | ¹H NMR (300 MHz, DMSO-d₆) δ ppm 0.93 (d, J = 6.03 Hz, 3 H), 1.35-1.50 (m, 1 H), 1.59 (s, 3 H), 1.64-1.76 (m, 4 H), 1.78-1.96 (m, 2 H), 2.14 (s, 3 H), 2.35-2.47 (m, 1 H), 2.41-2.49 (m, 3 H), 2.71 (dd, J = 11.11, 2.26 Hz, 1 H), 2.92-3.02 (m, 1 H), 3.03-3.11 (m, 1 H), 3.36-3.49 (m, 2 H), 4.56-4.85 (m, 2 H), 8.21 (s, 1 H), 10.16 (br. s., 1 H). | 447 |

-continued

| Ex. No. | Ki app (nM) | Structure IUPAC Name | ¹H NMR | MS (m/z) |
|---|---|---|---|---|
| | | 2-((5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol | | |
| H10 | 180 | 2-((5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol | ¹H NMR (300 MHz, DMSO-$d_6$) δ ppm 1.16 (d, J = 6.40 Hz, 3 H), 1.38-1.53 (m, 1 H), 1.59 (s, 3 H), 1.64 (s, 3 H), 1.68-1.83 (m, 1 H), 1.93-2.04 (m, 1 H), 2.13 (s, 3 H), 2.18-2.29 (m, 1 H), 2.45 (s, 3 H), 2.53-2.62 (m, 1 H), 2.74-2.91 (m, 1 H), 2.99-3.14 (m, J = 12.53, 2.17 Hz, 1 H), 3.37-3.50 (m, 2 H), 3.61-3.81 (m, 1 H), 4.36-4.80 (m, 2 H), 8.21 (d, J = 3.77 Hz, 1 H), 10.09 (s, 1 H) | 447 |
| I1 | 1.73 | N-(5-fluoro-2-propylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine | ¹H NMR (300 MHz, DMSO-$d_6$) δ 0.90 (s, 3 H) 0.93-0.94 (m, 2H) 0.97 (s, 3 H) 1.05-1.07 (m, 3 H) 1.57 (s, 3 H) 1.63 (s, 3 H) 1.73-1.78 (m, 2H) 1.90 (s, 2 H) 2.08 (s, 3 H) 2.54-2.63 (m, 3 H) 2.65-2.72 (m, 2 H) 2.74-2.90 (m, 2 H) 4.53-4.66 (m, 2 H) 8.24 (s, 1 H) 10.06 (s, 1 H). | 459 |
| I2 | 3.67 | N-(5-fluoro-2-isopropylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine | ¹H NMR (300 MHz, DMSO-$d_6$) δ 1.03-1.05 (m, 3 H) 1.21-1.22 (m, 3 H) 1.23-1.24 (m, 6H) 1.27-1.28 (m, 3H), 1.32-1.34 (m, 3H) 1.58-1.62 (m, 3 H) 1.69-1.70 (m, 3 H) 2.63-2.75 (m, 4 H) 2.98-3.03 (m, 1 H) 3.17-3.18 (m, 2 H) 4.49-4.53 (m, 1 H) 4.69-4.81 (m, 1 H) 8.28-8.32 (m, 1 H) 10.10 (s, 1 H) | 459 |
| J1 | 21.2 | 5-[(4-fluoro-1-methylpiperidin-4-yl)carbonyl]-N-(3-fluoro-6-methylpyridin-2-yl)-6,6-dimethyl-1,4,5,6-tetrahydropyrrolo[3,4-c]pyrazol-3-amine | 1H NMR (400 MHz, DMSO-$d_6$): δ ppm 1.23 (s, 3 H) 1.66 (s, 6 H) 1.92-2.18 (m, 6 H) 2.20 (s, 3 H) 2.35 (s, 3 H) 2.64-2.76 (m, 2 H) 4.95 (d, J = 4.03 Hz, 2 H) 6.61 (d, J = 6.55 Hz, 1 H) 7.34-7.47 (m, 1 H) 9.31 (br, 1 H) 11.65 (br, 1 H) | 405 |

| Ex. No. | Ki app (nM) | Structure IUPAC Name | ¹H NMR | MS (m/z) |
|---|---|---|---|---|
| J2 | 59.9 | 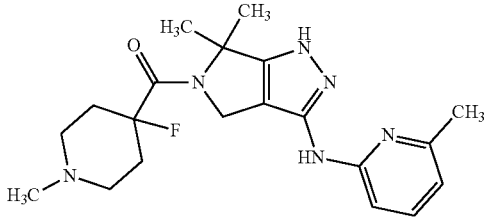<br>5-[(4-fluoro-1-methylpiperidin-4-yl)carbonyl]-6,6-dimethyl-N-(6-methylpyridin-2-yl)-1,4,5,6-tetrahydropyrrolo[3,4-c]pyrazol-3-amine | ¹H NMR (MEOD, 400 MHz): δ ppm 1.77 (6H, s), 2.11-2.21 (2H, m), 2.25-2.42 (2H, m), 2.44 (3H, s) 2.52 (3H, s) 2.62-2.73 (m, 2H) 3.03-3.08 (2H, m), 4.99 (2H, d, J = 4.5 Hz), 6.6 (1H, d, J = 8.3 Hz), 6.67 (1H, d, J = 7.3 Hz), 7.42-7.51 (1H, m). | 387 |
| J3 | 2.63 | 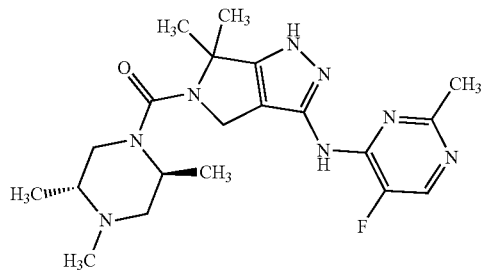<br>N-(3-fluoro-6-methylpyridin-2-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine | 1H NMR (400 MHz, DMSO-$d_6$): δ ppm 0.90-0.97 (m, 6 H) 1.57 (s, 3 H) 1.66 (s, 3 H) 1.80 (t, J = 10.70 Hz, 1 H) 1.96-2.08 (m, 1 H) 2.13 (s, 3 H) 2.28-2.36 (m, 1 H) 2.40 (s, 3H) 2.65-2.75 (m, 1 H) 2.92-3.06 (m, 2 H) 4.61-4.78 (m, 2 H) 6.58-6.70 (m, 1 H) 7.33-7.49 (m, 1 H) 9.36 (br, 1 H) 11.83 (br, 1 H) | 416 |
| J4 | 8.64 | 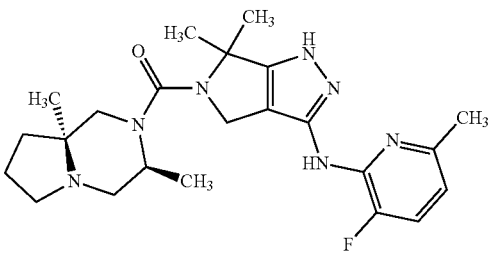<br>5-{[(3S,8aS)-3,8a-dimethylhexahydropyrrolo[1,2-a]pyrazin-2(1H)-yl]carbonyl}-N-(3-fluoro-6-methylpyridin-2-yl)-6,6-dimethyl-1,4,5,6-tetrahydropyrrolo[3,4-c]pyrazol-3-amine | 1H NMR (400 MHz, DMSO-$d_6$): δ ppm 0.86 (s, 3 H) 1.07 (d, J = 6.55 Hz, 3 H) 1.39-1.51 (m, 2 H) 1.53 (s, 3 H) 1.60-1.76 (m, 5 H) 2.33-2.45 (m, 4 H) 2.57-2.69 (m, 2 H) 2.71-2.78 (m, 1 H) 3.02-3.14 (m, 2 H) 3.80-3.90 (m, 1 H) 4.40 (d, J = 12.59 Hz, 1 H) 4.68 (d, J = 12.59 Hz, 1 H) 6.62 (dd, J = 8.06, 2.52 Hz, 1 H) 7.40 (dd, J = 11.33, 8.06 Hz, 1 H) 9.27 (br, 1 H) 11.85 (br, 1 H). | |
| J5 | 6.43 | 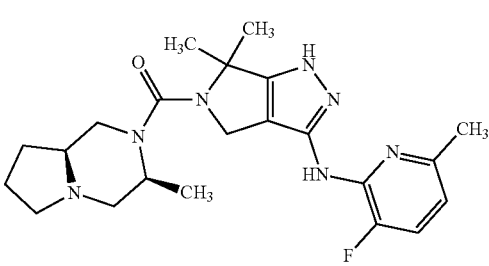 [SMILES: Cc1ccc(F)c(Nc2n[nH]c3c2CN(C(=O)N2C[C@@H]4CCCN4C[C@@H]2C)C3(C)C)n1]<br>N-(3-fluoro-6-methylpyridin-2-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine | 1H NMR (400 MHz, DMSO-$d_6$) δ ppm 1.19 (d, J = 6.80 Hz, 3 H) 1.22-1.35 (m, 1 H) 1.53-1.84 (m, 11 H) 2.19 (dd, J = 10.32, 3.53 Hz, 1 H) 2.57-2.82 (m, 3 H) 2.88-2.96 (m, 1 H) 3.79-3.90 (m, J = 6.55 Hz, 1 H) 4.46 (d, J = 12.84 Hz, 1 H) 4.63 (d, J = 12.84 Hz, 1 H) 6.61 (dd, J = 8.31, 2.64 Hz, 1 H) 7.40 (dd, J = 10.83, 8.31 Hz, 1 H) 9.25 (br, 1 H) 11.73 (br, 1 H) | 428 |

-continued

| Ex. No. | Ki app (nM) | Structure IUPAC Name | $^1$H NMR | MS (m/z) |
|---|---|---|---|---|
| J6 | 1.17 | 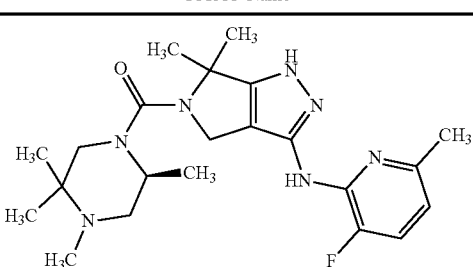<br>N-(3-fluoro-6-methylpyridin-2-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine | 1H NMR (400 MHz, DMSO-d$_6$) δ ppm 0.90 (s, 3 H) 0.98 (s, 3 H) 1.05 (d, J = 6.29 Hz, 3 H) 1.55 (s, 3 H) 1.66 (s, 3 H) 2.08 (s, 3 H) 2.15-2.25 (m, 1 H) 2.37 (s, 3 H) 2.53-2.62 (m, 2 H) 2.74-2.84 (m, 1 H) 3.36-3.45 (m, 1 H) 4.51-4.66 (m, 2 H) 6.62 (dd, J = 7.81, 2.27 Hz, 1 H) 7.41 (dd, J = 10.95, 7.81 Hz, 1 H) 9.30 (br, 1 H) 11.86 (br, 1 H). | 430 |
| J7 | 111 | 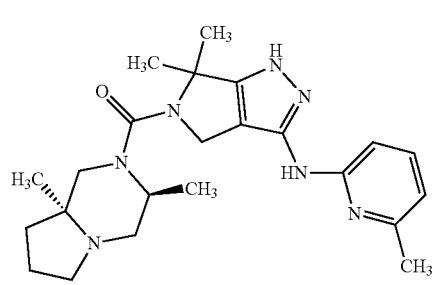 [SMILES: Cc1cccc(Nc2n[nH]c3c2CN(C(=O)N2C[C@]4(C)CCCN4C[C@@H]2C)C3(C)C)n1]<br>5-{[(3S,8aS)-3,8a-dimethylhexahydropyrrolo[1,2-a]pyrazin-2(1H)-yl]carbonyl}-6,6-dimethyl-N-(6-methylpyridin-2-yl)-1,4,5,6-tetrahydropyrrolo[3,4-c]pyrazol-3-amine | 1H NMR (400 MHz, CHLOROFORM-d) δ ppm 1.12-1.22 (m, 6 H) 1.62-1.85 (m, 8 H) 1.86-1.99 (m, 2 H) 2.48 (s, 3 H) 2.53-2.66 (m, 1 H) 2.70-2.82 (m, 1 H) 3.02-3.12 (m, 1 H) 3.13-3.31 (m, 3 H) 3.97-4.10 (m, 1 H) 4.37 (d, J = 12.09 Hz, 1 H) 4.53 (d, J = 12.09 Hz, 1 H) 6.58 (d, J = 8.31 Hz, 1 H) 6.67 (d, J = 7.30 Hz, 1 H) 7.44-7.48 (m, 1 H) | 424 |
| J8 | 32 | 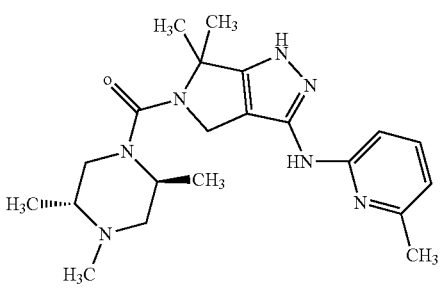<br>6,6-dimethyl-N-(6-methylpyridin-2-yl)-5-{[(2S,5R)-2,4,5-trimethylpiperazin-1-yl]carbonyl}-1,4,5,6-tetrahydropyrrolo[3,4-c]pyrazol-3-amine | 1H NMR (400 MHz, CHLOROFORM-d) δ ppm 1.04 (d, J = 6.04 Hz, 3 H) 1.08 (d, J = 6.29 Hz, 3 H) 1.73 (s, 3 H) 1.81 (s, 3 H) 2.19-2.34 (m, 4 H) 2.49 (s, 3 H) 2.60-2.71 (m, 1 H) 2.81 (dd, J = 11.46, 2.90 Hz, 1 H) 2.91-2.99 (m, 2 H) 3.22-3.31 (m, 1 H) 4.48 (d, J = 13.09 Hz, 1 H) 4.63 (d, J = 13.09 Hz, 1 H) 6.53 (d, J = 8.31 Hz, 1 H) 6.69 (d, J = 7.55 Hz, 1 H) 7.46 (t, J = 7.81 Hz, 1 H | 398 |
| J9 | 2.1 | 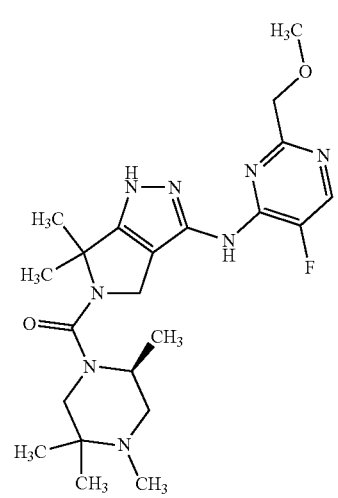 [SMILES: COCc1ncc(F)c(Nc2n[nH]c3c2CN(C(=O)N2CC(C)(C)N(C)C[C@@H]2C)C3(C)C)n1] | $^1$H NMR (400 MHz, DMSO-d$_6$) δ ppm 0.90 (s, 3 H), 0.93-1.00 (m, 3 H), 1.07 (d, J = 6.32 Hz, 3 H), 1.56 (s, 3 H), 1.68 (s, 3 H), 1.88 (s, 3 H), 2.05-2.10 (m, 3 H), 2.19 (dd, J = 11.62, 6.32 Hz, 1 H), 2.54-2.62 (m, 2 H), 2.83 (d, J = 12.13 Hz, 1 H), 3.41 (s, 2 H), 4.39 (s, 2 H), 4.53-4.65 (m, 2 H), 8.31 (s, 1 H) | 461 |

| Ex. No. | Ki app (nM) | Structure IUPAC Name | ¹H NMR | MS (m/z) |
|---|---|---|---|---|
| | | N-[5-fluoro-2-(methoxymethyl)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine | | |
| J10 | <10 | 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine | 1H NMR (300 MHz, DMSO-d₆) δ 0.89-1.02 (m, 6 H) 1.24 (t, J = 7.63 Hz, 3 H) 1.46-1.61 (m, 1 H) 1.57 (s, 3 H) 1.61-1.69 (m, 5 H) 1.71 (s, 3 H) 1.78-1.94 (m, 2 H) 1.86 (br. s., 1 H) 2.67-2.79 (m, 3 H) 2.79-2.89 (m, 1 H) 2.99-3.13 (m, 2 H) 3.05 (br. s., 1 H) 3.74-3.89 (m, 2 H) 3.82 (br. s., 1 H) 4.59-4.84 (m, 2 H) 8.20 (br. s., 1 H) | 515 |
| J11 | <10 | 5-{[(2S,5R)-2,5-dimethyl-4-(tetrahydro-2H-pyran-4-yl)piperazin-1-yl]carbonyl}-N-(4-methoxypyrimidin-2-yl)-6,6-dimethyl-1,4,5,6-tetrahydropyrrolo[3,4-c]pyrazol-3-amine | 1H NMR (400 MHz, DMSO-d₆) δ 0.92-1.04 (m, 6 H) 1.34-1.42 (m, 1 H) 1.45-1.53 (m, 2 H) 1.53-1.60 (m, 5 H) 1.64 (s, 3 H) 2.07-2.16 (m, 1 H) 2.70-2.78 (m, 2 H) 2.78-2.88 (m, 1 H) 3.04-3.13 (m, 2 H) 3.16 (s, 3 H) 3.83-3.93 (m, 5 H) 4.06-4.15 (m, 1 H) 4.43-4.60 (m, 2 H) 6.31 (br. s., 1 H) 8.16 (br. s., 1 H) | 485 |
| J12 | <10 | 5-{[(2S,5R)-2,5-dimethyl-4-(tetrahydro-2H-pyran-4-yl)piperazin-1-yl]carbonyl}-6,6-dimethyl-N-(4-methylpyrimidin-2-yl)-1,4,5,6-tetrahydropyrrolo[3,4-c]pyrazol-3-amine | 1H NMR (400 MHz, DMSO-d₆) δ 0.95-1.01 (m, 6 H) 1.32-1.43 (m, 1 H) 1.52-1.60 (m, 6 H) 1.65 (s, 3 H) 2.05-2.15 (m, 1 H) 2.37 (s, 3 H) 2.69-2.78 (m, 2 H) 2.80-2.90 (m, 1 H) 3.02-3.12 (m, 3 H) 3.14-3.19 (m, 4 H) 3.83-3.91 (m, 2 H) 4.04-4.15 (m, 1 H) 4.56-4.68 (m, 1 H) 6.72 (br. s., 1 H) 8.26 (br. s., 1 H) | 469 |
| J13 | <10 | | 1H NMR (400 MHz, DMSO-d₆) □ 0.91-1.14 (m, 7 H) 1.52-1.63 (m, 6 H) 1.64-1.75 (m, 5 H) 2.04-2.28 (m, 1 H) 2.70-2.90 (m, 2 H) 2.99-3.20 (m, 3 H) 3.81-3.97 (m, 3 H) 4.60 (br. s., 2 H) 7.24 (br. s., 1 H) 8.75 (br. s., 1 H) 10.49 (br. s., 1 H) 12.35 (br. s., 1 H) | 523 |

| Ex. No. | Ki app (nM) | Structure IUPAC Name | $^1$H NMR | MS (m/z) |
|---|---|---|---|---|
| | | 5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine | | |
| J14 | 19.2 | 5-{[(2S,5R)-2,5-dimethyl-4-(tetrahydro-2H-pyran-4-ylmethyl)piperazin-1-yl]carbonyl}-N-(4-methoxypyrimidin-2-yl)-6,6-dimethyl-1,4,5,6-tetrahydropyrrolo[3,4-c]pyrazol-3-amine | $^1$H NMR (300 MHz, DMSO-d$_6$) δ ppm 0.95 (d, J = 5.84 Hz, 3 H), 1.00 (d, J = 6.03 Hz, 3 H), 1.05-1.26 (m, 2 H), 1.49-1.73 (m, 10 H), 1.83-1.98 (m, 2 H), 2.31-2.45 (m, 2 H), 2.81 (d, J = 8.67 Hz, 1 H), 3.00-3.21 (m, 4 H), 3.82 (dd, J = 9.61, 1.70 Hz, 2 H), 3.88 (s, 3 H), 4.51 (s, 2 H), 6.30 (d, J = 5.46 Hz, 1 H), 8.15 (d, J = 5.65 Hz, 1 H), 9.86 (br. s., 1 H) | 499 |
| J15 | <10 | 5-{[(2S,5R)-2,5-dimethyl-4-(tetrahydro-2H-pyran-4-ylmethyl)piperazin-1-yl]carbonyl}-6,6-dimethyl-N-(4-methylpyrimidin-2-yl)-1,4,5,6-tetrahydropyrrolo[3,4-c]pyrazol-3-amine | 1H NMR (300 MHz, DMSO-d$_6$) δ ppm 0.95 (d, J = 5.46 Hz, 3 H), 0.99 (d, J = 5.84 Hz, 3 H), 1.04-1.19 (m, 2 H), 1.46-1.73 (m, 10 H), 1.80-1.95 (m, 2 H), 2.37 (s, 3 H), 2.39-2.47 (m, 2 H), 2.76-2.87 (m, 1 H), 3.00-3.14 (m, 2 H), 3.19-3.30 (m, 2 H), 3.82 (d, J = 8.67 Hz, 2 H), 4.61 (s, 2 H), 6.72 (s, 1 H), 8.27 (s, 1 H), 9.88 (br. s., 1 H), 11.90 (br. s., J = 1.51 Hz, 1 H). | 483 |
| J16 | 11.1 | N-(4,6-dimethylpyrimidin-2-yl)-5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-amine | $^1$H NMR (300 MHz, DMSO-d$_6$) δ ppm 0.94 (d, J = 5.84 Hz, 3 H), 0.98 (d, J = 6.03 Hz, 3 H), 1.01-1.22 (m, 2 H), 1.44-1.75 (m, 10 H), 1.78-1.90 (m, 2 H), 2.30 (s, 6 H), 2.37-2.46 (m, 2 H), 2.82 (d, J = 10.74 Hz, 1 H), 2.99-3.13 (m, 2 H), 3.18-3.30 (m, 2 H), 3.82 (d, J = 7.54 Hz, 2 H), 4.65 (s, 2 H), 6.61 (s, 1 H), 9.68 (br. s., 1 H), 11.90 (br. s., 1 H). Elemental Analysis: Calcd for C$_{26}$H$_{40}$N$_8$O$_2$•1.47 H$_2$O•0.66 CH$_3$COOH C 58.31, H 8.16, N 19.91 | 497 |

-continued

| Ex. No. | Ki app (nM) | Structure IUPAC Name | ¹H NMR | MS (m/z) |
|---|---|---|---|---|
| K1 | 1.12 | 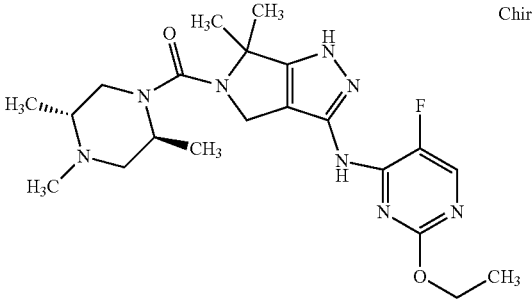Chiral<br>N-(2-ethoxy-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine | ¹H NMR (DMSO-d₆, 400 MHz): δ ppm 0.95 (5 H, dd, J = 11.49, 6.19 Hz), 1.31 (2 H, t, J = 7.07 Hz), 1.58 (2 H, s), 1.68 (2 H, s), 1.82-1.88 (1 H, m), 1.90 (2 H, s), 2.08-2.13 (1 H, m), 2.15 (2 H, s), 2.30-2.37 (1 H, m), 2.66-2.73 (1 H, m), 2.95-3.03 (2 H, m), 3.34 (7 H, s), 4.23-4.33 (2 H, m), 4.59-4.69 (1 H, m), 8.12 (1 H, d, J = 2.53 Hz). | 447 |
| K2 | 2.11 | 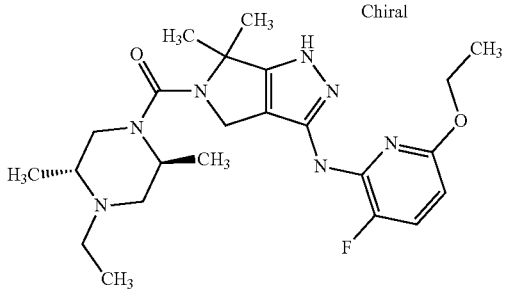 [SMILES: CCOc1ccc(F)c(Nc2n[nH]c3c2CN(C(=O)N2C[C@@H](C)N(CC)C[C@@H]2C)C3(C)C)n1]Chiral<br>N-(2-ethoxy-5-fluoropyrimidin-4-yl)-6,6-dimethyl-5-{[4-ethyl(2S,5R)-2,5-dimethylpiperazin-1-yl]carbonyl}-1,4,5,6-tetrahydropyrrolo[3,4-c]pyrazol-3-amine | 1H NMR (400 MHz, DMSO-d₆) δ ppm 0.94-0.98 (m, 9 H) 1.28 (t, J = 8 H) 1.57 (s, 3 H) 1.66 (s, 3 H) 1.95 (t, J = 8, 1 H) 2.28-2.32 (m, 1 H) 2.37-2.41 (m, 2 H) 2.67-2.77 (m, 2 H) 3.01-3.08 (m, 2 H) 4.21-4.29 (m, 2H) 4.61 (b, 2 H) 8.1 (m, 1 H) 10.1 (br, 1 H) 12.40 (br, 1 H). | 461 |
| K3 | 0.912 | 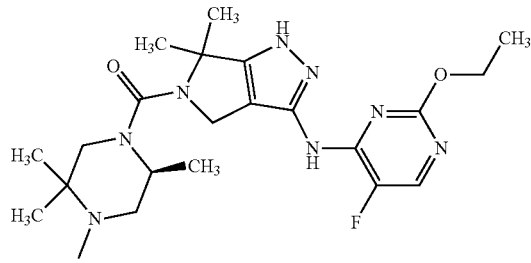 [SMILES: CCOc1ncc(F)c(Nc2n[nH]c3c2CN(C(=O)N2CC(C)(C)N(C)C[C@@H]2C)C3(C)C)n1]<br>N-(2-ethoxy-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine | ¹H NMR (400 MHz, DMSO-d₆) δ ppm 0.92 (3 H, s), 0.99 (3 H, s), 1.05 (3 H, d, J = 6.32 Hz), 1.30 (3 H, t, J = 7.07 Hz), 1.57 (3 H, s), 1.67 (3 H, s), 1.89 (1.4 H, s), 2.09 (3 H, s), 2.19 (1 H, dd, J = 11.49, 6.69 Hz), 2.57 (2 H, d, J = 12.13 Hz), 2.81 (1 H, d, J = 11.87 Hz), 3.31 (24 H, s), 4.24 (2 H, q, J = 6.99 Hz), 4.59 (2 H, m), 8.10 (1 H, s). | 461 |
| K4 | 3.33 | 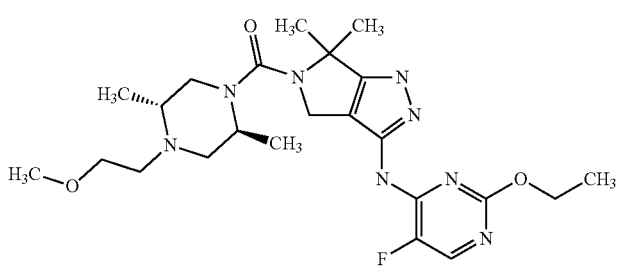<br>N-(2-ethoxy-5-fluoropyrimidin-4-yl)-5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-amine | | 491.4 |

-continued

| Ex. No. | Ki app (nM) | Structure IUPAC Name | $^1$H NMR | MS (m/z) |
|---|---|---|---|---|
| K5 | 0.683 | 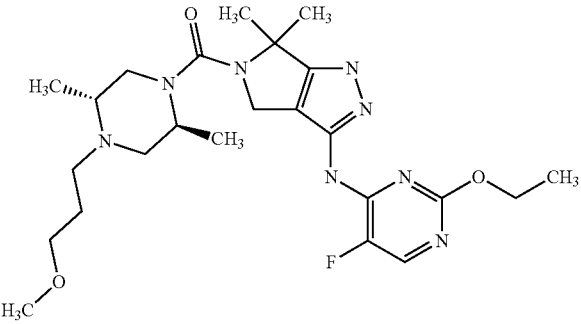 [SMILES: CCOc1ncc(F)c(Nc2n[nH]c3c2CN(C(=O)N2C[C@@H](C)N(CCCOC)C[C@@H]2C)C3(C)C)n1]<br>N-(2-ethoxy-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine | $^1$H NMR (300 MHz, DMSO-d6) δ ppm 0.95 (d, J = 5.09 Hz, 3 H) 0.98 (d, J = 6.22 Hz, 3 H) 1.29 (t, J = 6.97 Hz, 3 H) 1.58 (s, 3 H) 1.59-1.64 (m, 2 H) 1.67 (s, 3 H) 1.88-2.01 (m, 1 H) 2.11-2.26 (m, 1 H) 2.43 (d, J = 6.59 Hz, 2 H) 2.58-2.73 (m, 1 H) 2.73-2.84 (m, 1 H) 2.98-3.16 (m, 2 H) 3.21 (s, 3 H) 3.29-3.36 (m, 2 H) 4.16-4.35 (m, 2 H) 4.53-4.73 (m, 2 H) 8.11 (s, 1 H) 10.09 (br. s., 1 H) 12.36 (br. s., 1 H) | 505.4 |
| K6 | 0.376 | 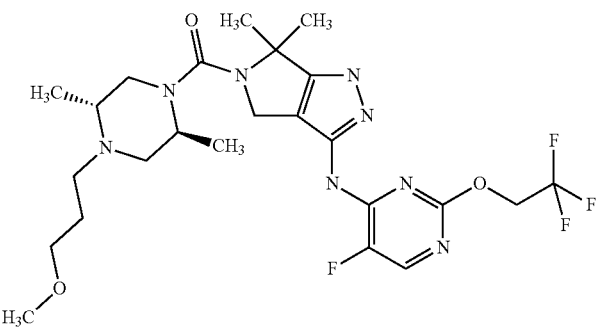 [SMILES: COCCCN1C[C@H](C)N(C(=O)N2Cc3c(Nc4nc(OCC(F)(F)F)ncc4F)n[nH]c3C2(C)C)C[C@H]1C]<br>N-[5-fluoro-2-(2,2,2-trifluoroethoxy)pyrimidin-4-yl]-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine | $^1$H NMR (300 MHz, DMSO-d$_6$) δ ppm 0.91 (d, J = 5.46 Hz, 3 H) 0.97 (d, J = 6.03 Hz, 3 H) 1.58 (s, 3 H) 1.60-1.65 (m, 2 H) 1.68 (s, 3 H) 1.88-2.02 (m, 1 H) 2.09-2.27 (m, 1 H) 2.32-2.46 (m, 2 H) 2.57-2.78 (m, 2 H) 2.96-3.16 (m, 2 H) 3.21 (s, 3 H) 3.29-3.39 (m, 2 H) 4.45-4.68 (m, 2 H) 4.78-5.06 (m, 2 H) 8.18 (s, 1 H) 10.32 (br. s., 1 H) 12.49 (br. s., 1 H) | 559.4 |
| K7 | 0.165 | 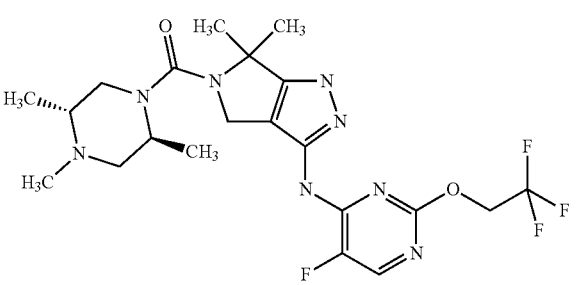 [SMILES: C[C@@H]1CN(C(=O)N2Cc3c(Nc4nc(OCC(F)(F)F)ncc4F)n[nH]c3C2(C)C)[C@@H](C)CN1C]<br>N-[5-fluoro-2-(2,2,2-trifluoroethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine | $^1$H NMR (300 MHz, DMSO-d$_6$) δ ppm 0.89-0.96 (m, 6 H), 1.58 (s, 3 H), 1.68 (s, 3 H), 1.79-1.92 (m, 1 H), 1.98-2.09 (m, 1 H), 2.12 (s, 3 H), 2.24-2.39 (m, 1 H), 2.60-2.70 (m, 1 H), 2.90-3.05 (m, 2 H), 4.49-4.74 (m, 2 H), 4.79-5.06 (m, 2 H), 8.18 (s, 1 H), 10.31 (br. s., 1 H), 12.47 (br. s., 1 H) | 501.4 |
| K8 | 0.181 | 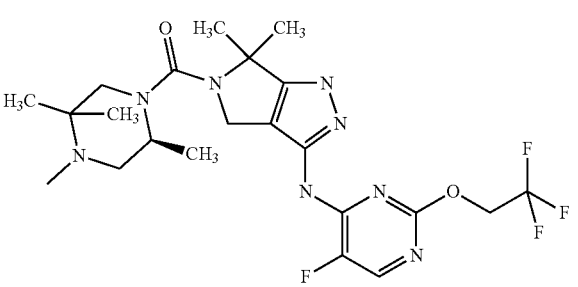 | $^1$H NMR (300 MHz, DMSO-d$_6$) δ ppm 0.88 (s, 3 H), 0.95 (s, 3 H), 1.03 (d, J = 6.2 Hz, 3 H), 1.57 (s, 3 H), 1.68 (s, 3 H), 2.06 (s, 3 H), 2.12-2.24 (m, 1 H), 2.50-2.62 (m, 2 H), 2.82 (d, J = 11.7 Hz, 1 H), 3.20-3.30 (m, 1 H), 4.47-4.66 (m, 2 H), 4.78-5.01 (m, 2 H), 8.16 (br. s., 1 H), 10.34 (br. s., 1 H), 12.49 (br. s., 1 H) | 515.4 |

-continued

| Ex. No. | Ki app (nM) | Structure IUPAC Name | ¹H NMR | MS (m/z) |
|---|---|---|---|---|
| | | N-[5-fluoro-2-(2,2,2-trifluoroethoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine | | |
| K9 | 12.8 | N-[5-fluoro-2-(3-methoxypropoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine | 1H NMR (300 MHz, DMSO-d₆) 0.91 (s, 3 H) 0.98 (s, 3 H) 1.01-1.11 (m, 3 H) 1.57 (s, 3 H) 1.67 (s, 3 H) 1.91-1.98 (m, 2 H) 2.08 (s, 3 H) 2.15-2.24 (m, 1 H) 2.53-2.61 (m, 3 H) 2.76-2.86 (m, 1 H) 3.16 (s, 1 H) 3.22 (s, 3 H) 3.40-3.49 (m, 3 H) 4.18-4.32 (m, 2 H) 4.52-4.66 (m, 2 H) 8.08-8.19 (m, 1 H). | 505 |
| K10 | 28.4 | 6,6-dimethyl-5-{[(2S,5R)-2,4,5-trimethylpiperazin-1-yl]carbonyl}-1,4,5,6-tetrahydropyrrolo[3,4-c]pyrazol-3-amine | 1H NMR (300 MHz, DMSO-d₆) 0.91-1.04 (m, 6 H) 1.58 (s, 3 H) 1.68 (s, 3 H) 1.92-1.99 (m, 2 H) 2.03-2.13 (m, 1 H) 2.15 (s, 3 H) 2.27-2.40 (m, 1 H) 2.65-2.76 (m, 1 H) 2.93-3.07 (m, 2 H) 3.22 (s, 3 H) 3.39-3.49 (m, 4 H) 4.18-4.34 (m, 2 H) 4.54-4.69 (m, 2 H) 8.12 (d, 1 H) 10.14 (s, 1 H). | 491 |
| K11 | 42.7 | N-[5-fluoro-2-(2-methoxyethoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine | 1H NMR (300 MHz, DMSO-d₆) 0.91 (s, 3 H) 0.98 (s, 3 H) 1.02-1.09 (m, 3 H) 1.57 (s, 3 H) 1.68 (s, 3 H) 2.08 (s, 3 H) 2.16-2.28 (m, 1 H) 2.53-2.60 (m, 2 H) 2.77-2.86 (m, 1 H) 3.16 (s, 2 H) 3.27 (s, 3 H) 3.57-3.70 (m, 2 H) 4.11 (s, 1 H) 4.27-4.38 (m, 2 H) 4.50-4.65 (m, 2 H) 8.12 (s, 1 H) | 491 |

| Ex. No. | Ki app (nM) | Structure IUPAC Name | ¹H NMR | MS (m/z) |
|---|---|---|---|---|
| K12 | 15.2 | 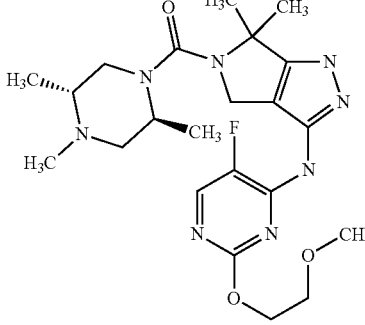<br>N-[5-fluoro-2-(2-methoxyethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine | 1H NMR (300 MHz, DMSO-$d_6$) 0.92-1.04 (m, 6 H) 1.58 (s, 3 H) 1.68 (s, 3 H) 1.82-1.90 (m, 2 H) 2.04-2.13 (m, 1 H) 2.15 (s, 3 H) 2.29-2.40 (m, 1 H) 2.65-2.75 (m, 1 H) 2.94-3.06 (m, 2 H) 3.27 (s, 3 H) 3.55-3.68 (m, 2 H) 4.27-4.41 (m, 2 H) 4.53-4.67 (m, 2 H) 8.13 (s, 1 H) 10.16 (s, 1 H) | 477 |
| K13 | 26.5 | 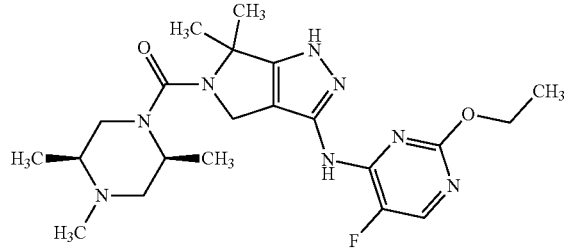 [SMILES: CCOc1ncc(F)c(Nc2n[nH]c3c2CN(C(=O)N2C[C@H](C)N(C)C[C@@H]2C)C3(C)C)n1]<br>2(S),5(S)-{[dimethyl-4-methylpiperazin-1-yl]carbonyl}-N-(5-fluoro-2-ethoxypyrimidin-4-yl)-6,6-dimethyl-1,4,5,6-tetrahydropyrrolo[3,4-c]pyrazol-3-amine | ¹H NMR (400 MHz, CDCl$_3$) δ ppm 1.18 (b, 3 H), 1.38 (t, J = 8 Hz, 3 H), 1.43 (b, 3 H), 1.73 (s, 3 H), 1.74 (s, 3 H), 2.36 (b, 3H), 2.57 (m, 1H), 2.75 (m, 1 H), 3.00 (m, 1 H), 3.29 (m, 1 H), 3.88 (m, 1H), 4.34 (q, J = 8 Hz, 2H), 4.63 (d, J = 16 Hz, 1 H), 4.69 (d, J = 16 Hz, 1 H), 7.96 (s, 1H), 8.41 (b, 1H). | 447 |
| K14 | 71.7 | 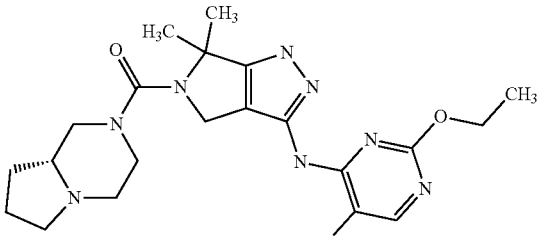<br>[3-(2-Ethoxy-5-fluoro-pyrimidin-4yl-amino)-6,6-dimethyl-4,6-dihydro-1H-pyrrolo[3,4-c]pyrazol-5-yl]-(R)-hexahydro-pyrrolo[1,2-a]pyrazin-2-yl-methanone | ¹H NMR (400 MHz, ACETONITRILE-$d_3$) δ ppm 1.28 (t, J = 8 Hz, 3 H), 1.60 (s, 3H), 1.61 (s, 3H), 1.65 (m, 3 H), 1.92 (m, 1 H), 2.03 (m, 1 H), 2.14 (m, 1 H), 2.43 (m, 1 H), 2.76 (m, 1 H), 2.90 (m, 1H), 2.96 (m, 1H), 3.40 (m, 2H), 3.52 (m, 1H), 4.23 (q, J = 8 Hz, 2 H), 4.51 (d, J = 12 Hz, 1 H), 4.61 (d, J = 12 Hz, 1 H), 8.10 (s, 1 H), 10.14 (s, 1H), 12.25 (b, 1 H) | 445 |
| K15 | 11.2 | 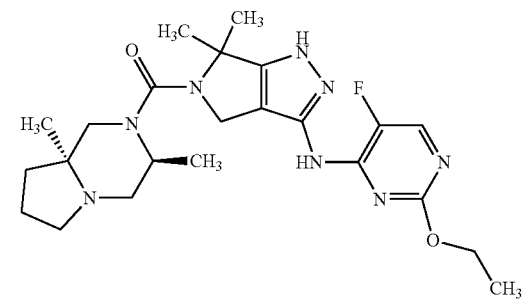 [SMILES: CCOc1ncc(F)c(Nc2n[nH]c3c2CN(C(=O)N2C[C@]4(C)CCCN4C[C@@H]2C)C3(C)C)n1]<br>5-{[(3S,8aS)-3,8a-dimethylhexahydropyrrolo[1,2-a]pyrazin-2(1H)-yl]carbonyl}-N-(2-ethoxy-5- | 1H NMR (400 MHz, CHLOROFORM-d) δ ppm 1.15-1.25 (m, 6 H) 1.42 (t, J = 7.05 Hz, 3 H) 1.63-1.87 (m, 8 H) 1.88-1.99 (m, 2 H) 2.55-2.66 (m, 1 H) 2.69-2.79 (m, 1 H) 3.08-3.39 (m, 4 H) 4.05-4.18 (m, 1 H) 4.37 (q, J = 7.05 Hz, 2 H) 4.53 (d, J = 12.84 Hz, 1 H) 4.78 (d, J = 12.84 Hz, 1 H) 8.00 (d, J = 2.77 Hz, 1 H) 8.66 (brs, 1 H) | 473 |

-continued

| Ex. No. | Ki app (nM) | Structure<br>IUPAC Name | $^1$H NMR | MS (m/z) |
|---|---|---|---|---|
| | | fluoropyrimidin-4-yl)-6,6-dimethyl-1,4,5,6-tetrahydropyrrolo[3,4-c]pyrazol-3-amine | | |
| K16 | 38.4 | 5-{[(3S)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine | $^1$H NMR (400 MHz, DMSO-d$_6$) δ ppm 0.97 (d, J = 6.06 Hz, 2 H), 1.30 (t, J = 7.07 Hz, 3 H), 1.61 (s, 5 H), 2.06 (td, J = 6.32, 3.28 Hz, 1 H), 2.12-2.17 (m, 1 H), 2.18 (s, 2 H), 2.43 (dd, J = 12.25, 9.98 Hz, 1 H), 2.69 (d, J = 11.12 Hz, 1 H), 2.76-2.85 (m, 1 H), 3.20-3.29 (m, 1 H), 3.32 (s, 7 H), 4.27 (q, J = 6.99 Hz, 2 H), 4.59 (s, 2 H), 8.10 (s, 1 H | 456 |
| K17 | 44.4 | 5-{[(3R)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine | $^1$H NMR (400 MHz, ACETONITRILE-d$_3$) δ ppm 1.17-1.26 (m, 3 H), 1.35 (t, J = 6.95 Hz, 3 H), 1.67 (d, J = 3.03 Hz, 6 H), 2.11 (dt, J = 4.99, 2.43 Hz, 5 H), 2.53 (s, 3 H), 2.71 (s, 1 H), 2.86 (s, 1 H), 3.43 (d, J = 11.12 Hz, 2 H), 4.32 (q, J = 7.07 Hz, 2 H), 4.64 (s, 2 H), 7.99 (d, J = 2.78 Hz, 1 H), 8.42 (s, 1 H). Calcd for C$_{20}$H$_{29}$FN$_8$O (M + H): 317. | 433 |
| K18 | 25.3 | 5-{[(2S,5R)-2,5-dimethyl-4-(3,3,3-trifluoropropyl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine | 1H NMR (300 MHz, DMSO-d$_6$) 0.94-1.07 (m, 6 H) 1.23-1.35 (m, 3 H) 1.58 (s, 3 H) 1.67 (s, 3 H) 1.95-2.08 (m, 1 H) 2.33-2.48 (m, 6 H) 2.76-2.91 (m, 2 H) 3.03-3.18 (m, 2 H) 4.18-4.32 (m, 2 H) 4.62 (s, 2 H) 8.09 (s, 1 H) 10.10 (s, 1 H) | 529 |

| Ex. No. | Ki app (nM) | Structure / IUPAC Name | ¹H NMR | MS (m/z) |
|---|---|---|---|---|
| K19 | <10 | 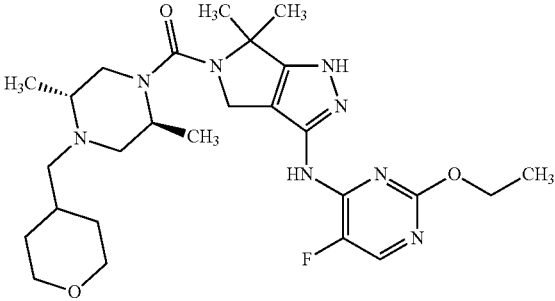 [SMILES: CCOc1ncc(F)c(Nc2n[nH]c3c2CN(C(=O)N2C[C@@H](C)N(CC4CCOCC4)C[C@@H]2C)C3(C)C)n1]<br>5-{[(2S,5R)-2,5-dimethyl-4-(tetrahydro-2H-pyran-4-ylmethyl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine | 1H NMR (300 MHz, DMSO-$d_6$) δ 0.89-0.97 (m, 3 H) 0.97-1.05 (m, 3 H) 1.05-1.20 (m, 3 H) 1.21-1.35 (m, 3 H) 1.51 (br. s., 1 H) 1.57 (s, 3 H) 1.67 (s, 5 H) 1.94 (br. s., 1 H) 2.37-2.47 (m, 3 H) 2.54 (d, J = 0.75 Hz, 1 H) 2.76-2.89 (m, 1 H) 3.03-3.12 (m, 1 H) 3.12-3.21 (m, 1 H) 3.21-3.29 (m, 2 H) 3.76-3.90 (m, 2 H) 4.18-4.36 (m, 2 H) 4.53-4.74 (m, 2 H) 8.08-8.22 (m, 1 H) 10.14 (br. s., 1 H) | 531 |
| K20 | 26 | 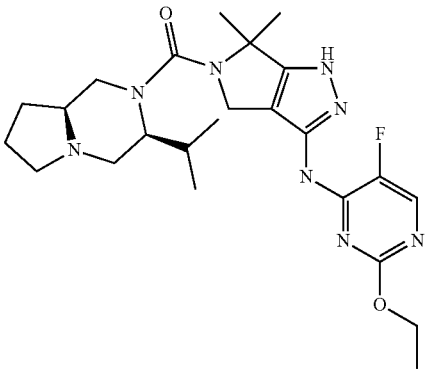 [SMILES: CCOc1ncc(F)c(Nc2n[nH]c3c2CN(C(=O)N2C[C@@H]4CCCN4C[C@@H]2C(C)C)C3(C)C)n1]<br>N-(2-ethoxy-5-fluoropyrimidin-4-yl)-5-{[(3S,8aS)-3-isopropylhexahydropyrrolo[1,2-a]pyrazin-2(1H)-yl]carbonyl}-6,6-dimethyl-1,4,5,6-tetrahydropyrrolo[3,4-c]pyrazol-3-amine | 1H NMR (400 MHz, CHLOROFORM-d) δ ppm 0.83-1.05 (m, 7 H) 1.30-1.51 (m, 4 H) 1.61-1.95 (m, 10 H) 2.21-2.46 (m, 2 H) 2.92-3.11 (m, 2 H) 3.14-3.32 (m, 1 H) 3.49-3.57 (m, 1 H) 3.59-3.76 (m, 1 H) 4.36 (q, J = 6.97 Hz, 2 H) 4.54-4.60 (m, 1 H) 4.75-4.92 (m, 1 H) 8.00 (d, J = 2.52 Hz, 1 H) | 487 |
| K21 | <10 | 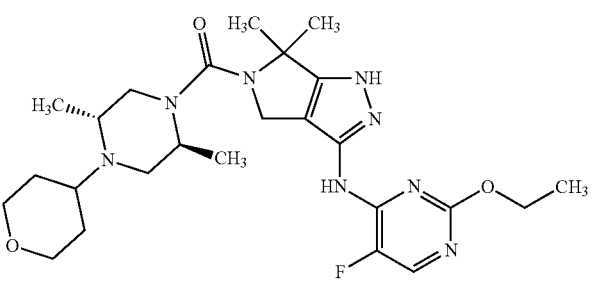 [SMILES: CCOc1ncc(F)c(Nc2n[nH]c3c2CN(C(=O)N2C[C@@H](C)N(C4CCOCC4)C[C@@H]2C)C3(C)C)n1]<br>5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine | 1H NMR (300 MHz, DMSO-$d_6$) δ 0.92-1.08 (m, 6 H) 1.28 (t, J = 6.97 Hz, 3 H) 1.32-1.44 (m, 1 H) 1.46-1.55 (m, 2 H) 1.57 (s, 3 H) 1.67 (s, 3 H) 2.08-2.21 (m, 1 H) 2.51-2.58 (m, 1 H) 2.53 (s, 1 H) 2.68-2.86 (m, 3 H) 3.04-3.15 (m, 1 H) 3.15-3.26 (m, 2 H) 3.26-3.48 (m, 3 H) 3.77-3.95 (m, 2 H) 4.16-4.34 (m, 2 H) 4.51-4.70 (m, 1 H) 8.10 (d, J = 3.01 Hz, 1 H) 10.15 (br. s., 1 H) | 517 |

| Ex. No. | Ki app (nM) | Structure IUPAC Name | ¹H NMR | MS (m/z) |
|---|---|---|---|---|
| K22 | 15.3 | 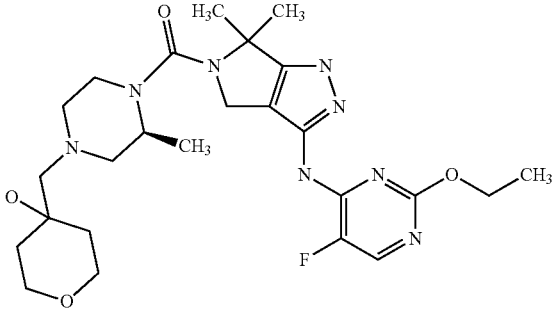 [SMILES: CCOc1ncc(F)c(Nc2n[nH]c3c2CN(C(=O)N2CCN(CC4(O)CCOCC4)C[C@@H]2C)C3(C)C)n1]<br>4-[((2R,5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol | ¹H NMR (300 MHz, DMSO-$d_6$) ppm 0.96 (d, J = 4.52 Hz, 3 H), 1.04 (d, J = 5.84 Hz, 3 H), 1.22-1.44 (m, 5 H), 1.51-1.74 (m, 8 H), 2.06-2.24 (m, 2 H), 2.36-2.47 (m, 1 H), 2.52-2.68 (m, 2 H), 2.99-3.09 (m, 1 H), 3.11-3.22 (m, 1 H), 3.52-3.70 (m, 4 H), 4.09 (br. s., 1 H), 4.19-4.35 (m, 2 H), 4.50-4.73 (m, 2 H), 8.12 (s, 1 H), 10.14 (s, 1 H), 12.17 (br. s., 1 H). | 547 |
| K23 | <10 | 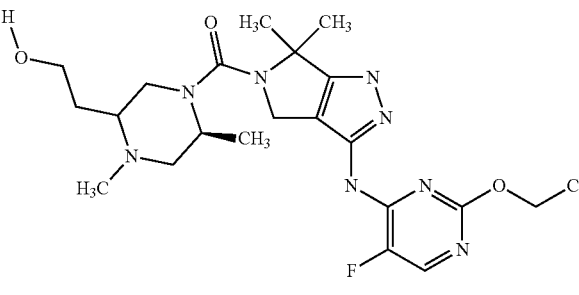<br>2-((5S)-4-{[3-](2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol | ¹H NMR (300 MHz, DMSO-$d_6$) δ ppm 0.95 (d, J = 6.03 Hz, 3 H), 1.30 (t, J = 6.97 Hz, 3 H), 1.42-1.54 (m, 1 H), 1.58 (s, 3 H), 1.64-1.77 (m, 4 H), 1.83-1.99 (m, 1 H), 2.09-2.27 (m, 4 H), 2.51-2.59 (m, 1 H), 2.66-2.79 (m 1 H), 2.94-3.13 (m, 2 H), 3.37-3.51 (m, 2 H), 4.27 (q, J = 6.84 Hz, 2 H), 4.52-4.72 (m, 2 H), 8.12 (s, 1 H), 10.13 (s, 1 H), 12.42 (br. s., 1 H). | 477 |
| K24 | <10 | 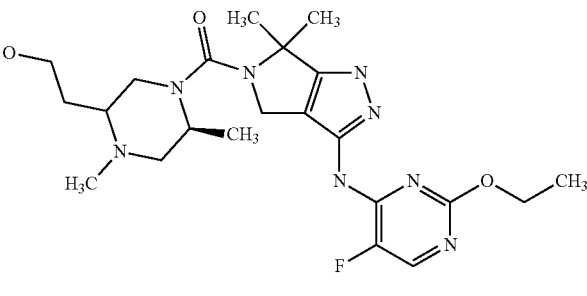 [SMILES: CCOc1ncc(F)c(Nc2n[nH]c3c2CN(C(=O)N2CC(CCO)N(C)C[C@@H]2C)C3(C)C)n1]<br>2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol | ¹H NMR (300 MHz, DMSO-$d_6$) δ ppm 1.19 (d, J = 6.59 Hz, 3 H), 1.29 (t, J = 7.06 Hz, 3 H), 1.39-1.55 (m, 1 H), 1.59 (s, 3 H), 1.63 (s, 3 H), 1.68-1.84 (m, 1 H), 1.97-2.10 (m, 1 H), 2.15 (s, 3 H), 2.23-2.36 (m, 1 H), 2.53-2.61 (m, 1 H), 2.70-2.89 (m, 1 H), 3.04-3.15 (m, 1 H), 3.39-3.48 (m, 2 H), 3.62-3.76 (m, 1 H), 4.26 (q, J = 6.97 Hz, 2 H), 4.45-4.67 (m, 2H), 8.11 (d, J = 2.83 Hz, 1 H), 10.12 (s, 1 H). | 477 |
| K25 | 36.5 | 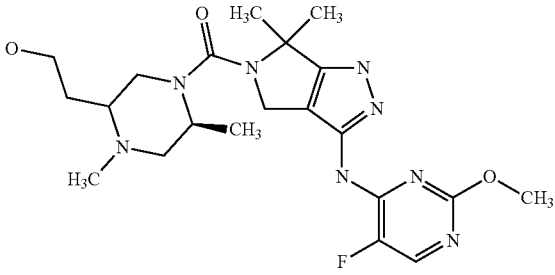 [SMILES: COc1ncc(F)c(Nc2n[nH]c3c2CN(C(=O)N2CC(CCO)N(C)C[C@@H]2C)C3(C)C)n1]<br>2-((5S)-4-{[3-[(5-fluoro-2-methoxypyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol | ¹H NMR (300 MHz, CHLOROFORM-d) δ ppm 1.10 (d, J = 6.03 Hz, 3 H), 1.74 (s, 3 H), 1.81 (s, 3 H), 1.88-2.03 (m, 1 H), 2.32 (t, J = 11.40 Hz, 1 H), 2.48 (s, 3 H), 2.76-2.89 (m, 1 H), 2.88-3.07 (m, 2 H), 3.08-3.23 (m, 1 H), 3.28-3.43 (m, 2 H), 3.66-3.78 (m, 2 H), 3.82-3.93 (m, 1 H), 3.97 (s, 3 H), 4.62-4.84 (m, 2 H), 7.99 (d, J = 2.64 Hz, 1 H), 8.92 (br. s., 1 H). | 463 |

| Ex. No. | Ki app (nM) | Structure IUPAC Name | ¹H NMR | MS (m/z) |
|---|---|---|---|---|
| K26 | 54.7 | 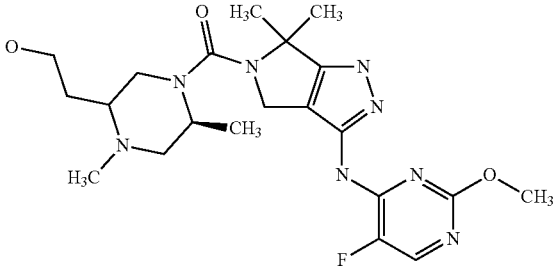 [SMILES: COc1ncc(F)c(Nc2n[nH]c3c2CN(C(=O)N2CC(CCO)N(C)C[C@@H]2C)C3(C)C)n1]<br>2-((5S)-4-{[3-[(5-fluoro-2-methoxypyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol | ¹H NMR (300 MHz, CHLOROFORM-d) δ ppm 1.22-1.33 (m, 1 H), 1.38 (d, J = 6.59 Hz, 3 H), 1.76 (d, J = 2.64 Hz, 7 H), 2.00-2.23 (m, 2 H), 2.45 (s, 3 H), 2.50-2.63 (m, 2 H), 2.73-2.87 (m, 1 H), 3.14-3.44 (m, 1 H), 3.68-3.88 (m, 2 H), 3.95 (s, 4 H), 4.74 (s, 2 H), 7.99 (d, J = 2.64 Hz, 1 H) | 463 |
| L1 | 16.8 | 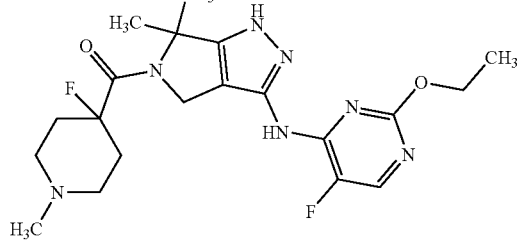<br>N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine | ¹H NMR (DMSO-$d_6$, 400 MHz) δ ppm 1.28 (2 H, t, J = 7.07 Hz), 1.68 (4 H, s), 1.91 (2 H, s), 1.91-1.95 (1 H, m), 2.13 (2 H, d, J = 9.09 Hz), 2.19 (2 H, s), 2.68 (1 H, d, J = 5.31 Hz), 3.32 (8 H, s), 4.22 (2 H, q, J = 7.07 Hz), 4.90 (1 H, d, J = 3.28 Hz), 8.12 (1 H, s), 10.18 (1 H, s). | 436 |
| L2 | 168 | 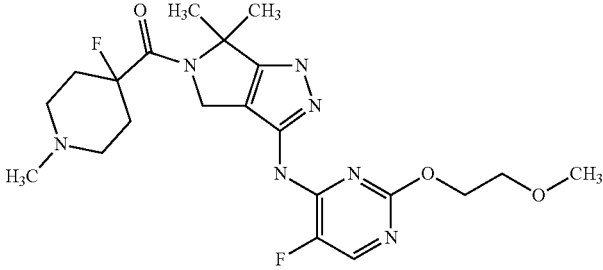<br>N-[5-fluoro-2-(2-methoxyethoxy)pyrimidin-4-yl]-5-[(4-fluoro-1-methylpiperidin-4-yl)carbonyl]-6,6-dimethyl-1,4,5,6-tetrahydropyrrolo[3,4-c]pyrazol-3-amine | ¹H NMR (300 MHz, DMSO-$d_6$) δ ppm 1.68 (s, 6 H), 1.84-2.09 (m, 4 H), 2.10-2.16 (m, 2 H), 2.18 (s, 3 H), 2.60-2.74 (m, 2 H), 3.28 (s, 3 H), 3.55-3.66 (m, 2 H), 4.22-4.38 (m, 2 H), 4.79-4.96 (m, 2 H), 8.12 (s, 1 H), 10.14 (br. s., 1 H), 12.46 (br. s., 1 H) | 466.4 |
| L3 | 58.6 | 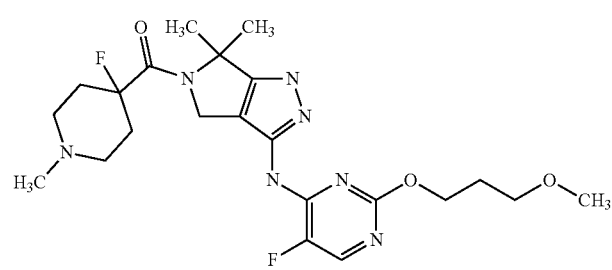<br>N-[5-fluoro-2-(3-methoxypropoxy)pyrimidin-4-yl]-5-[(4-fluoro-1-methylpiperidin-4-yl)carbonyl]-6,6-dimethyl-1,4,5,6-tetrahydropyrrolo[3,4-c]pyrazol-3-amine | ¹H NMR (300 MHz, DMSO-$d_6$) δ ppm 1.68 (s, 6 H), 1.83-1.97 (m, 4 H), 1.97-2.09 (m, 2 H), 2.09-2.15 (m, 2 H), 2.17 (s, 3 H), 2.59-2.71 (m, 2 H), 3.23 (s, 3 H), 3.45 (t, J = 6.3 Hz, 2 H), 4.21 (t, J = 6.3 Hz, 2 H), 4.83-4.98 (m, 2 H), 8.11 (s, 1 H), 10.15 (br. s., 1 H), 12.47 (br. s., 1 H). | 480.4 |

-continued

| Ex. No. | Ki app (nM) | Structure IUPAC Name | $^1$H NMR | MS (m/z) |
|---|---|---|---|---|
| L4 | 1.71 | 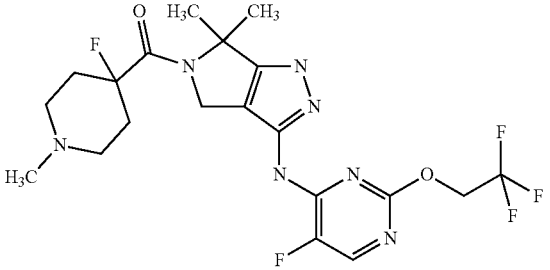 [SMILES: CN1CCC(F)(C(=O)N2Cc3c(Nc4nc(OCC(F)(F)F)ncc4F)n[nH]c3C2(C)C)CC1]  5-[(4-fluoro-1-methylpiperidin-4-yl)carbonyl]-N-[5-fluoro-2-(2,2,2-trifluoroethoxy)pyrimidin-4-yl]-6,6-dimethyl-1,4,5,6-tetrahydropyrrolo[3,4-c]pyrazol-3-amine | $^1$H NMR (300 MHz, DMSO-$d_6$) δ ppm 1.68 (s, 6 H) 1.80-1.90 (m, 2 H) 1.92-2.11 (m, 2 H) 2.10-2.16 (m, J = 8.48 Hz, 2 H) 2.18 (s, 3 H) 2.58-2.71 (m, 2 H) 4.78-5.00 (m, 4 H) 8.13-8.23 (m, J = 3.01 Hz, 1 H) 8.29 (br. s., 2 H) | 490.4 |
| L5 | 129 | 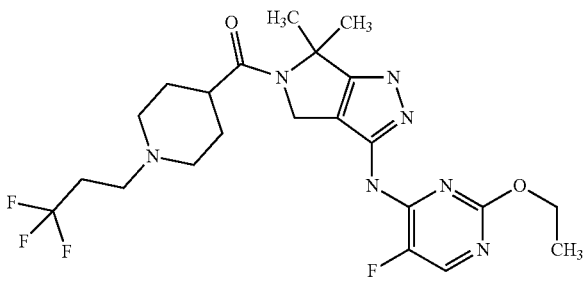 [SMILES: CCOc1ncc(F)c(Nc2n[nH]c3c2CN(C(=O)C2CCN(CCC(F)(F)F)CC2)C3(C)C)n1]  N-(2-ethoxy-5-fluoropyrimidin-4-yl)-6,6-dimethyl-5-{[1-(3,3,3-trifluoropropyl)piperidin-4-yl]carbonyl}-1,4,5,6-tetrahydropyrrolo[3,4-c]pyrazol-3-amine | 1H NMR (300 MHz, DMSO-$d_6$) 1.26-1.35 (m, 3 H) 1.56-1.71 (m, 12 H) 1.92-2.02 (m, 2 H) 2.32-2.46 (m, 3 H) 2.88-3.02 (m, 3 H) 4.20-4.30 (m, 2 H) 4.79 (s, 2 H) 8.04-8.17 (m, 1 H) 10.18 (s, 1 H) | 500 |
| L6 | 181 | 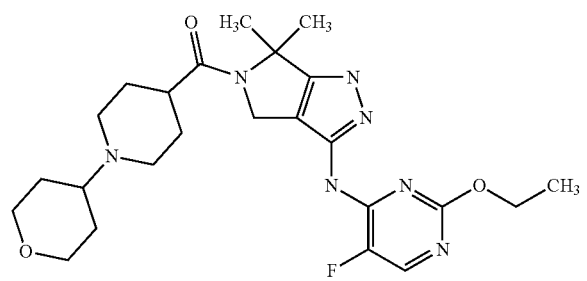 [SMILES: CCOc1ncc(F)c(Nc2n[nH]c3c2CN(C(=O)C2CCN(C4CCOCC4)CC2)C3(C)C)n1]  N-(2-ethoxy-5-fluoropyrimidin-4-yl)-6,6-dimethyl-5-{[1-(tetrahydro-2H-pyran-4-yl)piperidin-4-yl]carbonyl}-1,4,5,6-tetrahydropyrrolo[3,4-c]pyrazol-3-amine | $^1$H NMR (300 MHz, DMSO-$d_6$) δ ppm 1.24-1.36 (m, 3 H) 1.38-1.55 (m, 2 H) 1.57-1.69 (m, 10 H) 2.03-2.22 (m, 2 H) 2.26-2.45 (m, 2 H) 2.83-3.00 (m, 2 H) 3.12-3.27 (m, 4 H) 3.79-3.96 (m, 2 H) 4.25 (q, J = 6.8 Hz, 2 H) 4.68-4.89 (m, 2 H) 8.09 (s, 1 H) 10.17 (br. s., 1 H) 12.41 (br. s., 1 H) | 488.4 |
| M1 | 4.24 | 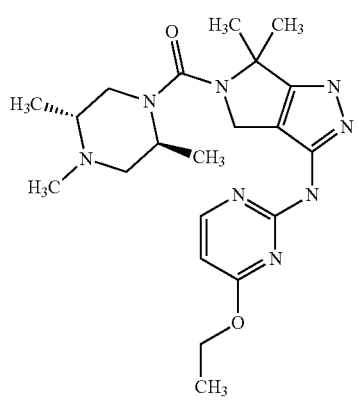 [SMILES: CCOc1ccnc(Nc2n[nH]c3c2CN(C(=O)N2C[C@@H](C)N(C)C[C@@H]2C)C3(C)C)n1] | 1H NMR (300 MHz, CDCl$_3$-d) δ ppm 1.09 (m, 6 H) 1.42 (m, 3 H) 1.73 (s, 3 H) 1.80 (s, 3 H) 2.34 (s, 3 H) 2.71 (m, 2 H) 2.83 (m, 2 H) 2.98 (m, 2 H) 3.30 (bs, 2 H) 4.38 (m, 2 H) 4.44-4.67 (m, 2 H) 6.27 (m, 1 H) 8.16 (m, 1 H) | 429 |

| Ex. No. | Ki app (nM) | Structure IUPAC Name | ¹H NMR | MS (m/z) |
|---|---|---|---|---|
| | | N-(4-ethoxypyrimidin-2-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine | | |
| M2 | 16.1 | 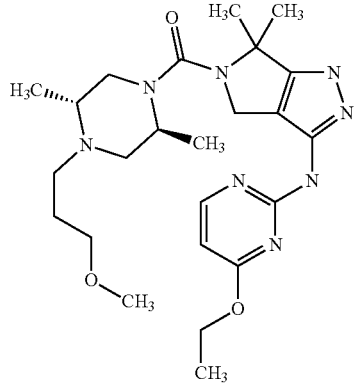 [SMILES: CCOc1ccnc(Nc2n[nH]c3c2CN(C(=O)N2C[C@@H](C)N(CCCOC)C[C@@H]2C)C3(C)C)n1] N-(4-ethoxypyrimidin-2-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine | 1H NMR (300 MHz, DMSO-d₆) δ ppm 0.97 (m, 6 H) 1.32 (m, 3 H) 1.56 (s, 3 H) 1.64 (s, 3 H) 1.85-2.00 (m, 2 H) 2.12-2.28 (m, 1 H) 2.31-2.45 (m, 2 H) 2.58-2.70 (m, 1 H) 2.70-2.86 (m, 2 H) 2.96-3.11 (m, 2 H) 3.21 (m, 5 H) 4.26-4.42 (m, 2 H) 4.42-4.58 (m, 2 H) 6.20-6.35 (m, 1 H) 8.14 (s, 1 H) 9.96 (bs, 1H) 11.96 (bs, 1H) | 487 |
| N1 | <10 | 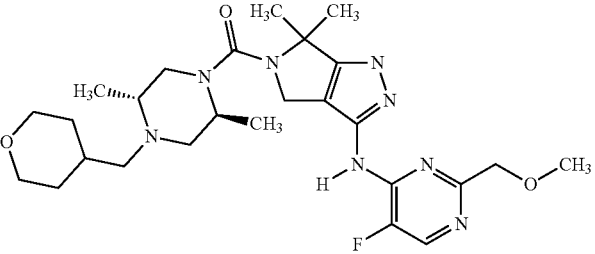 [SMILES: COCc1ncc(F)c(Nc2n[nH]c3c2CN(C(=O)N2C[C@@H](C)N(CC4CCOCC4)C[C@@H]2C)C3(C)C)n1] 5-{[(2S,5R)-2,5-dimethyl-4-(tetrahydro-2H-pyran-4-ylmethyl)piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine | ¹H NMR (300 MHz, DMSO-d₆) δ ppm 0.94 (d, J = 5.27 Hz, 3 H), 0.99 (d, J = 5.84 Hz, 3 H), 1.03-1.22 (m, 2 H), 1.45-1.78 (m, 10 H), 1.82-1.98 (m, 2 H), 2.33-2.47 (m, 2 H), 2.83 (d, J = 9.04 Hz, 1 H), 3.07 (d, J = 9.04 Hz, 2 H), 3.20-3.30 (m, 2 H), 3.82 (d, J = 10.17 Hz, 2 H), 4.42 (s, 2 H), 4.58-4.76 (m, 2 H), 8.33 (s, 1 H), 10.28 (br. s., 1 H), 12.36 (br. s., 1 H). | 531 |
| N2 | <10 | 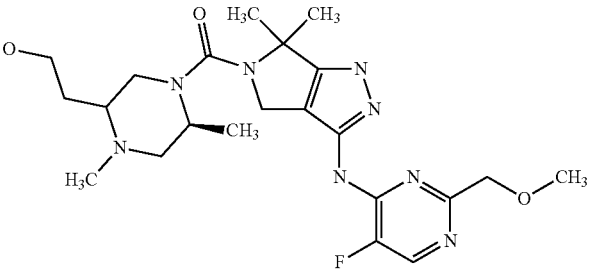 [SMILES: COCc1ncc(F)c(Nc2n[nH]c3c2CN(C(=O)N2CC(CCO)N(C)C[C@@H]2C)C3(C)C)n1] 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol | ¹H NMR (300 MHz, CHLOROFORM-d) δ ppm 1.11 (d, J = 5.84 Hz, 3 H), 1.74 (s, 3 H), 1.81 (s, 3 H), 1.85-1.99 (m, 2 H), 2.55 (s, 3 H), 2.92-3.09 (m, 3 H), 3.10-3.24 (m, 1 H), 3.32-3.46 (m, 1 H), 3.51 (s, 3 H), 3.68-3.80 (m, 1 H), 3.80-3.95 (m, 1 H), 4.56 (s, 2 H), 4.66-4.88 (m, 3 H), 8.19 (d, J = 2.83 Hz, 1 H), 9.24 (br. s., 1 H) | 477 |

-continued

| Ex. No. | Ki app (nM) | Structure IUPAC Name | $^1$H NMR | MS (m/z) |
|---|---|---|---|---|
| N3 | 15.6 | 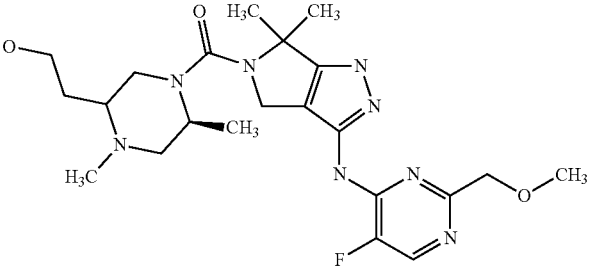 [SMILES: COCc1ncc(F)c(Nc2n[nH]c3c2CN(C(=O)N2CC(CCO)N(C)C[C@@H]2C)C3(C)C)n1]<br>((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol | $^1$H NMR (300 MHz, CHLOROFORM-d) δ ppm 1.30-1.38 (m, 3 H), 1.74 (s, 3 H), 1.77 (s, 3 H), 1.81-1.90 (m, 1 H), 1.94-2.03 (m, 1 H), 2.45 (s, 3 H), 2.49-2.63 (m, 2 H), 2.75-2.86 (m, 1 H), 3.14-3.29 (m, 1 H), 3.29-3.39 (m, 1 H), 3.51 (s, 3 H), 3.72-3.85 (m, 2 H), 3.86-4.00 (m, 1 H), 4.56 (s, 2 H), 4.59-4.73 (m, 2 H), 8.23 (d, J = 2.83 Hz, 1 H), 9.17 (br. s., 1 H) | 477 |

We claim:

1. A method for treating diabetic mellitus in a patient in need thereof, wherein the method comprises administering to the patient 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine having the following structure:

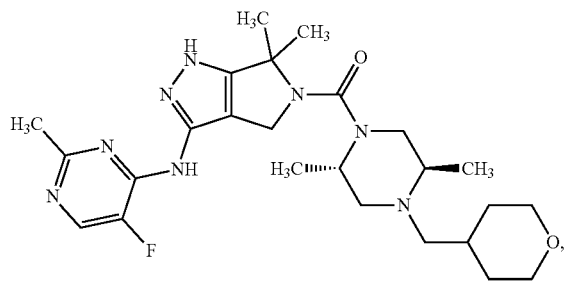 [SMILES: Cc1ncc(F)c(Nc2n[nH]c3c2CN(C(=O)N2C[C@@H](C)N(CC4CCOCC4)C[C@@H]2C)C3(C)C)n1]

or a pharmaceutically acceptable salt thereof.

2. A method for treating a complication arising from diabetic mellitus in a patient in need thereof, wherein the method comprises administering to the patient 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine having the following structure:

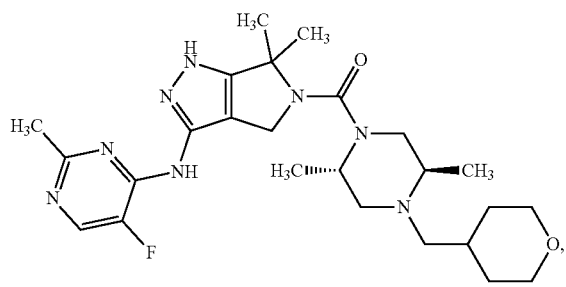 [SMILES: Cc1ncc(F)c(Nc2n[nH]c3c2CN(C(=O)N2C[C@@H](C)N(CC4CCOCC4)C[C@@H]2C)C3(C)C)n1]

or a pharmaceutically acceptable salt thereof.

3. The method of claim 2, wherein the complication arising from diabetes mellitus is diabetic macular edema.

4. The method of claim 2, wherein the complication arising from diabetes mellitus is diabetic nephropathy.

5. The method of claim 2, wherein the complication arising from diabetes mellitus is diabetic neuropathy.

6. The method of claim 2, wherein the complication arising from diabetes mellitus is diabetic retinopathy.

7. A method for treating diabetic mellitus in a patient in need thereof, wherein the method comprises administering to the patient a pharmaceutical composition comprising a pharmaceutically acceptable excipient and 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine having the following structure:

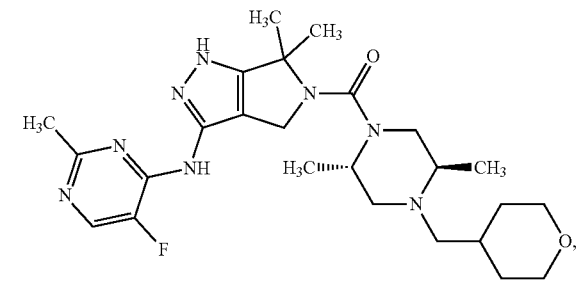 [SMILES: Cc1ncc(F)c(Nc2n[nH]c3c2CN(C(=O)N2C[C@@H](C)N(CC4CCOCC4)C[C@@H]2C)C3(C)C)n1]

or a pharmaceutically acceptable salt thereof.

8. A method for treating a complication arising from diabetic mellitus in a patient in need thereof, wherein the method comprises administering to the patient a pharmaceutical composition comprising a pharmaceutically acceptable excipient and 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine having the following structure:

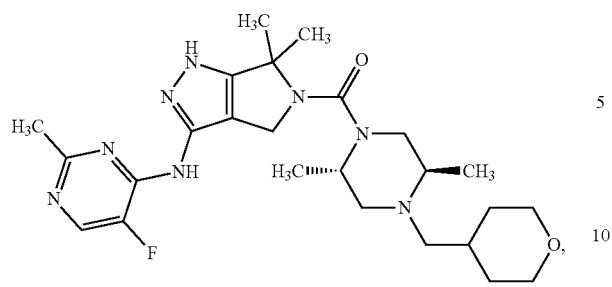

or a pharmaceutically acceptable salt thereof.

9. The method of claim 8, wherein the complication arising from diabetes mellitus is diabetic macular edema.

10. The method of claim 8, wherein the complication arising from diabetes mellitus is diabetic nephropathy.

11. The method of claim 8, wherein the complication arising from diabetes mellitus is diabetic neuropathy.

12. The method of claim 8, wherein the complication arising from diabetes mellitus is diabetic retinopathy.

13. The method of claim 8, wherein the pharmaceutical composition is administered orally to the patient.

14. The method of claim 8, wherein the pharmaceutical composition is administered topically to the patient.

15. The method of claim 8, wherein the pharmaceutical composition is administered topically to an eye of the patient.

* * * * *